US012714563B2

(12) United States Patent
Guidotti et al.

(10) Patent No.: US 12,714,563 B2
(45) Date of Patent: Aug. 25, 2026

(54) CARDIAC LEAFLET COAPTERS

(71) Applicant: MTEX CARDIO AG, Pfäffikon (CH)

(72) Inventors: Andrea Guidotti, Zollikon (CH); Monica Tocchi, Zurich (CH); Karl Heinz Kuck, Hamburg (DE); Michael Butscheid, Wilen bei Wollerau (CH); Yaniv Marmur, Yokneam Moshava (IL); Pietro Gozzoli, Zurich (CH)

(73) Assignee: MTEX CARDIO AG, Pfaffikon (CH)

( * ) Notice: Subject to any disclaimer, the term of this patent is extended or adjusted under 35 U.S.C. 154(b) by 701 days.

(21) Appl. No.: 18/006,254

(22) PCT Filed: Jul. 22, 2020

(86) PCT No.: PCT/IB2020/056926
§ 371 (c)(1),
(2) Date: Jan. 20, 2023

(87) PCT Pub. No.: WO2022/018494
PCT Pub. Date: Jan. 27, 2022

(65) Prior Publication Data
US 2023/0270549 A1 Aug. 31, 2023

(51) Int. Cl.
*A61F 2/24* (2006.01)

(52) U.S. Cl.
CPC .......... *A61F 2/2463* (2013.01); *A61F 2/2457* (2013.01); *A61F 2/2466* (2013.01); (Continued)

(58) Field of Classification Search
CPC ...... A61F 2/246; A61F 2/2463; A61F 2/2475; A61F 2/2476; A61F 2/2478; A61F 2/2457
See application file for complete search history.

(56) References Cited

U.S. PATENT DOCUMENTS

| | | | |
|---|---|---|---|
| 5,607,445 | A | 3/1997 | Summers |
| 5,810,882 | A | 9/1998 | Bolduc et al. |

(Continued)

FOREIGN PATENT DOCUMENTS

| | | | |
|---|---|---|---|
| CN | 104055600 | A | 9/2014 |
| CN | 106572910 | A | 4/2017 |

(Continued)

OTHER PUBLICATIONS

International Search Report and Written Opinion dated Feb. 5, 2015, issued in International Application No. PCT/IB2014/002155.

(Continued)

*Primary Examiner* — Alvin J Stewart
(74) *Attorney, Agent, or Firm* — Sughrue Mion, PLLC

(57) ABSTRACT

Coaptation-assist devices (20) are provided for treating a native atrioventricular valve. The coaptation-assist devices (20) include a ventricular anchor (30), which includes one or more wires (35), and which is configured to be positioned in a ventricle; and a neo-leaflet (32), which is supported by the ventricular anchor (30) and is configured to at least partially replace function of a target native leaflet of the native atrioventricular valve by providing a surface of coaptation (34) for one or more opposing native leaflets. In some configurations, the ventricular anchor (30) includes a proximal subannular anchor (54), which includes a digitate anchor (56) that is shaped so as to define a plurality of fingers (60) having a plurality of curved superior peaks (66) that point in a superior direction and engage a subannular surface of the target native leaflet. Other embodiments are also described.

20 Claims, 35 Drawing Sheets

(52) U.S. Cl.
CPC ................. *A61F 2220/0008* (2013.01); *A61F 2230/0056* (2013.01)

(56) References Cited

U.S. PATENT DOCUMENTS 6,419,695 B1 7/2002 Gabbay
6,478,776 B1 11/2002 Rosenman et al.
6,629,534 B1 10/2003 St. Goar et al.
6,663,633 B1 12/2003 Pierson, III
6,752,813 B2 6/2004 Goldfarb et al.
6,869,444 B2 3/2005 Gabbay
6,986,775 B2 1/2006 Morales et al.
7,070,618 B2 7/2006 Streeter
7,160,322 B2 1/2007 Gabbay
7,374,572 B2 5/2008 Gabbay
7,381,220 B2* 6/2008 Macoviak ............. A61F 2/2454 623/2.12
7,527,646 B2 5/2009 Rahdert et al.
7,544,198 B2 6/2009 Parodi
7,635,329 B2 12/2009 Goldfarb et al.
7,988,725 B2 8/2011 Gross et al.
8,216,303 B2 7/2012 Navia
8,449,599 B2 5/2013 Chau et al.
8,870,936 B2 10/2014 Rowe
8,870,950 B2 10/2014 Hacohen
8,876,894 B2 11/2014 Tuval et al.
9,232,999 B2 1/2016 Maurer et al.
9,445,893 B2 9/2016 Vaturi
9,592,121 B1 3/2017 Khairkhahan
10,166,098 B2 1/2019 Khairkhahan et al.
10,226,341 B2 3/2019 Gross et al.
10,751,180 B2 8/2020 Schewel
2001/0021872 A1 9/2001 Bailey et al.
2003/0120340 A1 6/2003 Liska et al.
2003/0199975 A1 10/2003 Gabbay
2005/0004668 A1 1/2005 Aklog et al.
2005/0010287 A1 1/2005 Macoviak et al.
2005/0038509 A1 2/2005 Ashe
2005/0107871 A1 5/2005 Realyvasquez et al.
2005/0159810 A1 7/2005 Filsoufi
2005/0235511 A1 10/2005 Tkachyk
2006/0195183 A1 8/2006 Navia et al.
2006/0235511 A1 10/2006 Osborne
2006/0293698 A1 12/2006 Douk
2007/0185571 A1 8/2007 Kapadia et al.
2009/0048668 A1 2/2009 Wilson et al.
2009/0132036 A1 5/2009 Navia
2009/0138079 A1 5/2009 Tuval et al.
2010/0036479 A1 2/2010 Hill et al.
2010/0298929 A1 11/2010 Thornton et al.
2011/0166644 A1 7/2011 Keeble et al.
2011/0319990 A1 12/2011 Macoviak et al.
2012/0150290 A1 6/2012 Gabbay
2012/0179247 A1 7/2012 Navia
2012/0197388 A1 8/2012 Khairkhahan et al.
2012/0245678 A1 9/2012 Solem
2013/0023985 A1 1/2013 Khairkhahan et al.
2013/0103140 A1 4/2013 Subramanian et al.
2013/0261737 A1 10/2013 Costello
2014/0025163 A1 1/2014 Padala et al.
2014/0031928 A1 1/2014 Murphy et al.
2014/0067048 A1 3/2014 Chau et al.
2014/0067054 A1 3/2014 Chau et al.
2014/0121763 A1 5/2014 Duffy et al.
2014/0207231 A1 7/2014 Hacohen et al.
2014/0257467 A1 9/2014 Lane et al.
2014/0316516 A1 10/2014 Vidlund et al.
2014/0350662 A1 11/2014 Vaturi
2014/0358223 A1 12/2014 Rafiee et al.
2015/0119981 A1* 4/2015 Khairkhahan ........ A61F 2/2442
2015/0119982 A1 4/2015 Quill et al.
2015/0127097 A1 5/2015 Neumann et al.
2015/0142103 A1 5/2015 Vidlund
2015/0265404 A1 9/2015 Rankin
2016/0074164 A1* 3/2016 Naor ..................... A61F 2/2409 623/2.11
2016/0166382 A1 6/2016 Nguyen
2016/0184098 A1 6/2016 Vaturi
2016/0324639 A1* 11/2016 Nguyen ................ A61F 2/2409
2017/0065418 A1 3/2017 Skarsgard
2017/0112618 A1 4/2017 Li et al.
2017/0128203 A1 5/2017 Zhang et al.
2017/0209265 A1 7/2017 Karapetian et al.
2018/0289473 A1 10/2018 Rajagopal et al.
2019/0029826 A1* 1/2019 Zeitani .................. A61F 2/2445
2019/0060072 A1 2/2019 Zeng
2019/0201191 A1* 7/2019 McLean ................ A61F 2/0063
2019/0201192 A1 7/2019 Kruse et al.
2019/0254817 A1 8/2019 Centola et al.
2019/0282364 A1 9/2019 Khairkhahan et al.
2019/0290431 A1 9/2019 Genovese et al.
2019/0290432 A1 9/2019 Duffy et al.
2019/0298332 A1 10/2019 Khairkhahan et al.
2019/0350705 A1 11/2019 Schewel et al.
2020/0188109 A1 6/2020 Fatemi Far et al.
2020/0205969 A1 7/2020 Hacohen
2020/0222185 A1 7/2020 Kappetein et al.
2020/0275974 A1 9/2020 Gifford, III et al.
2020/0289265 A1* 9/2020 Gifford, III ........... A61F 2/2442
2020/0330229 A1* 10/2020 Serraf ................... A61F 2/2463
2020/0383776 A1* 12/2020 Schewel ............... A61F 2/2466
2021/0085462 A1 3/2021 Gifford, III et al.
2021/0196462 A1* 7/2021 Khairkhahan ........ A61F 2/2445
2022/0096236 A1* 3/2022 Guidotti ................ A61F 2/2463
2022/0273433 A1* 9/2022 Kuck .................... A61F 2/2454
2024/0225837 A1* 7/2024 Martin .................. A61F 2/2421
2024/0335288 A1* 10/2024 Ruban ................... A61F 2/2463
2024/0415641 A1* 12/2024 Mohl .................... A61F 2/2463
2025/0025300 A1* 1/2025 Chang ................... A61F 2/2466

FOREIGN PATENT DOCUMENTS

EP 3 620 133 A1 3/2020
EP 3708122 B1 * 2/2026 ............. A61F 2/246
RU 2853431 C1 * 12/2025
WO 2005/112827 A2 12/2005
WO 2006/097931 A2 9/2006
WO 2007/131513 A1 11/2007
WO 2008/035337 A2 3/2008
WO 2009/116041 A2 9/2009
WO 2012/102928 A1 8/2012
WO 2013/021375 A2 2/2013
WO 2013/150512 A1 10/2013
WO 2013/192107 A1 12/2013
WO 2014/114796 A1 7/2014
WO 2014/144937 A2 9/2014
WO 2014/188412 A2 11/2014
WO 2014/189974 A1 11/2014
WO 2014/207575 A2 12/2014
WO 2015/017689 A1 2/2015
WO 2015/057407 A1 4/2015
WO 2015/061533 A1 4/2015
WO 2015/195823 A1 12/2015
WO 2015/200497 A1 12/2015
WO 2016/098104 A2 6/2016
WO 2017/079279 A1 5/2017
WO 2017/115123 A1 7/2017
WO 2017/156133 A1 9/2017
WO 2018/142217 A2 8/2018
WO 2018/169878 A1 9/2018
WO 2019/045910 A1 3/2019
WO 2020/055433 A1 3/2020
WO 2020/101676 A1 5/2020
WO 2020/186106 A1 9/2020
WO 2020/236757 A1 11/2020
WO 2021/055983 A1 3/2021

OTHER PUBLICATIONS

International Search Report and Written Opinion dated Apr. 22, 2020, issued in International Application No. PCT/IL2020/050057.

(56) References Cited

OTHER PUBLICATIONS

International Search Report and Written Opinion dated Apr. 20, 2021, issued in International Application No. PCT/IB2020/056926.
International Search Report and Written Opinion dated Dec. 2, 2020, issued in International Application No. PCT/IB2020/057429.
International Search Report and Written Opinion dated Apr. 28, 2022, issued in International Application No. PCT/IB2022/050669.
Office Action dated Jan. 21, 2021 for U.S. Appl. No. 16/529,247.
Office Action dated Aug. 25, 2021 for U.S. Appl. No. 16/529,247.
Office Action dated Feb. 13, 2017 for U.S. Appl. No. 14/901,468.
Office Action dated Jun. 1, 2017 for U.S. Appl. No. 14/901,468.
Office Action dated Mar. 8, 2018 for U.S. Appl. No. 14/901,468.
Examiner Interview Summary dated Aug. 16, 2018 for U.S. Appl. No. 14/901,468.
Office Action dated Sep. 26, 2018 for U.S. Appl. No. 14/901,468.
Examiner Interview Summary dated Oct. 30, 2018 for U.S. Appl. No. 14/901,468.
Office Action dated Mar. 7, 2019 for U.S. Appl. No. 14/901,468.
Examiner Interview Summary dated Jul. 15, 2019 for U.S. Appl. No. 14/901,468.
Office Action dated Nov. 5, 2019 for U.S. Appl. No. 14/901,468.
Examiner Interview Summary dated Mar. 25, 2020 for U.S. Appl. No. 14/901,468.
Notice of Allowance dated May 13, 2020 for U.S. Appl. No. 14/901,468.
Office Action dated Jan. 20, 2023 for U.S. Appl. No. 16/921,687.
Translation of Office Action dated Jun. 28, 2024 for Chinese Application No. 202080021065.8.
Restriction Requirement issued in U.S. Appl. No. 17/422,900, dated Jun. 20, 2023.
Non-Final Office Action issued in U.S. Appl. No. 17/422,900, dated Mar. 27, 2024.
Final Office Action issued in U.S. Appl. No. 17/422,900, dated Apr. 17, 2025.

* cited by examiner

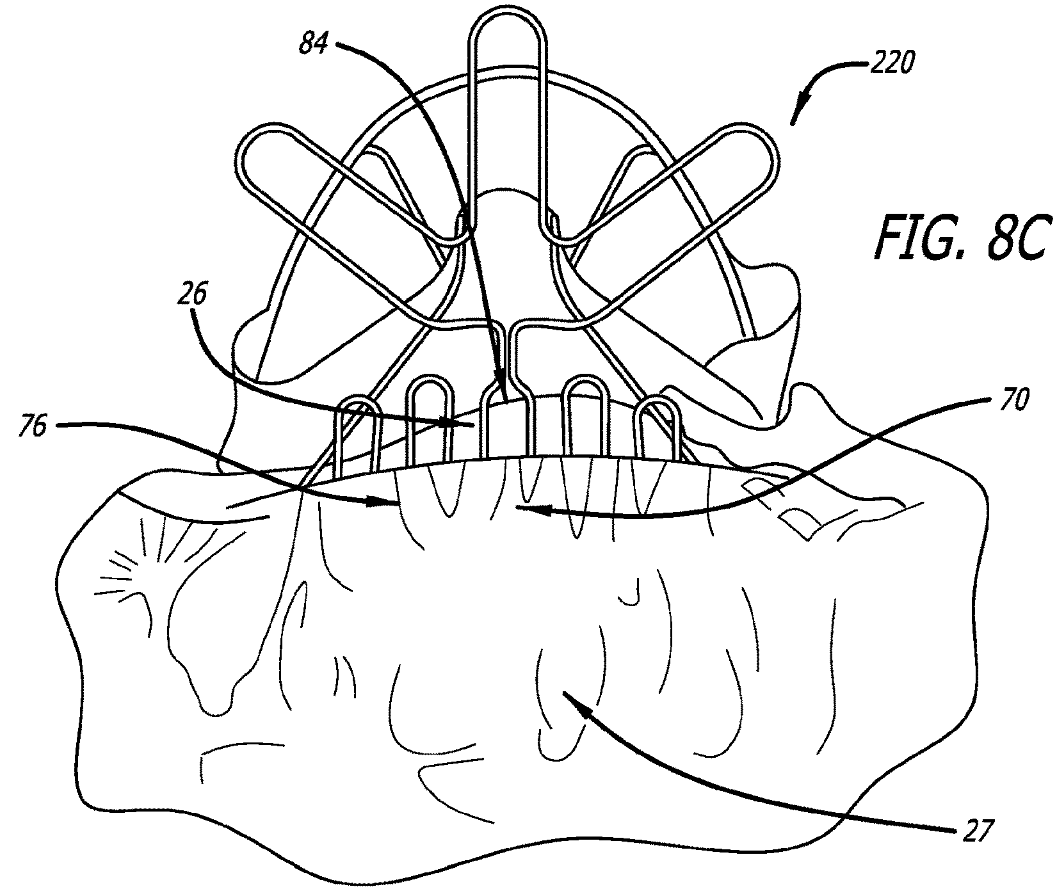
FIG. 8C
FIG. 8D
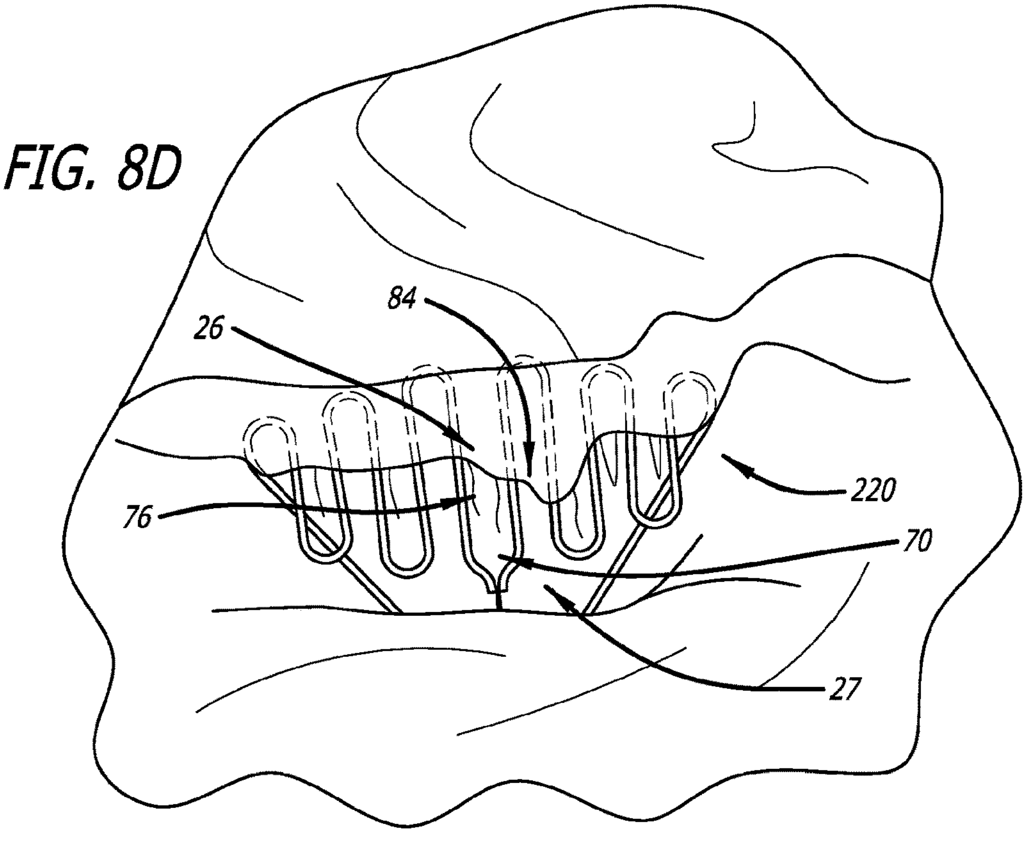

CARDIAC LEAFLET COAPTERS

CROSS-REFERENCE TO RELATED APPLICATIONS

The present application is the U.S. national stage of International Application PCT/IB2020/056926, filed Jul. 22, 2020, which published as PCT Publication WO 2022/018494 to Guidotti et al.

International Application PCT/IB2020/056926 is related to U.S. Provisional Application 62/792,092, filed Jan. 14, 2019, and International Application PCT/IL2020/050057, filed Jan. 14, 2020, which published as PCT Publication WO 2020/148755 to Guidotti et al., both of which are incorporated herein by reference.

FIELD OF THE INVENTION

The present invention relates generally to medical devices and methods. More particularly, this invention relates to prosthetic devices and methods for improving the function of regurgitating heart valves and other circulatory valves.

BACKGROUND OF THE APPLICATION

Valvular regurgitation (VR) is a disease in which the heart's native valve does not close properly, causing blood to flow backward into the atrium when the ventricle contracts, reducing its efficiency. Severe regurgitation affects more than 5 million patients in the U.S. today and is estimated to affect 8% of the world population.

SUMMARY OF THE APPLICATION

Embodiments of the present invention provide coaptation-assist devices for treating a native atrioventricular valve. The coaptation-assist devices comprise a ventricular anchor, which comprises one or more wires, and which is configured to be positioned in a ventricle; and a neo-leaflet, which is supported by the ventricular anchor and is configured to at least partially replace function of a target native leaflet of the native atrioventricular valve by providing a surface of coaptation for one or more opposing native leaflets. In some configurations, the ventricular anchor comprises a proximal subannular anchor, which includes a digitate anchor that is shaped so as to define a plurality of fingers having a plurality of curved superior peaks that point in a superior direction and engage a subannular surface of the target native leaflet.

There is therefore provided, in accordance with an application of the present invention, a coaptation-assist device for treating a native atrioventricular valve of a heart (or an aortic valve, or a pulmonary valve), the coaptation-assist device including:

a ventricular anchor, which includes one or more wires, and which is configured to be positioned in a ventricle of the heart; and a neo-leaflet, which is supported by the ventricular anchor and is configured to at least partially replace function of a target native leaflet of the native atrioventricular valve by providing a surface of coaptation for one or more opposing native leaflets that oppose the target native leaflet, when anchored in place by the ventricular anchor, the ventricular anchor including:

a proximal subannular anchor, which (a) includes a digitate anchor that (i) is defined at least in part by at least one of the one or more wires, and (ii) is shaped so as to define a plurality of fingers having a plurality of curved superior peaks, and (b) is configured to be positioned at least partially in a target subannular space defined by the target native leaflet and a superior portion of a ventricular wall of the ventricle, such that (i) the curved superior peaks point in a superior direction and engage a subannular surface of the target native leaflet, and (ii) one or more of the fingers engage chordae tendineae that extend between the target native leaflet and the superior portion of the ventricular wall, so as to stabilize the coaptation-assist device, and a distal anchor, which is configured to be positioned partially against the ventricular wall outside the target subannular space, so as to push on the proximal subannular anchor to help anchor the proximal subannular anchor in place within the target subannular space.

For some applications, the plurality of curved superior peaks includes between two and twelve curved superior peaks.

For some applications, the plurality of curved superior peaks includes between two and twelve curved superior peaks.

For some applications, the plurality of curved superior peaks includes between four and twelve curved superior peaks.

For some applications, the plurality of curved superior peaks includes between six and twelve curved superior peaks.

For some applications, the plurality of curved superior peaks includes between six and eight curved superior peaks.

For some applications, an average of respective greatest widths of the fingers, measured laterally, is between 2 and 10 mm when the fingers are unconstrained.

For some applications, a greatest width of a portion of the digitate anchor that defines the fingers is between 20 and 60 mm, when the fingers are unconstrained.

For some applications, an average of respective distances between midpoints of the curved superior peaks of adjacent pairs of the fingers is between 3 and 9 mm when the fingers are unconstrained.

For some applications, respective distances between midpoints of the curved superior peaks of adjacent pairs of the fingers vary along a width of the digitate anchor, when the fingers are unconstrained.

For some applications, all respective distances between midpoints of the curved superior peaks of adjacent pairs of the fingers equal one another, when the fingers are unconstrained.

For some applications, an average of respective heights of the fingers is between 4 and 30 mm, the respective heights measured in a superior-inferior direction, when the fingers are unconstrained.

For some applications, an average of respective radii of curvature of the curved superior peaks is between 1 and 10 mm when the fingers are unconstrained.

For some applications, for at least one of the fingers, a radius of curvature of the curved superior peak is greater than a smallest width of the finger, measured laterally when the fingers are unconstrained.

For some applications, when the fingers are unconstrained:

the fingers have respective greatest widths and respective heights, the greatest widths measured laterally, the respective heights measured in a superior-inferior direction, the fingers have respective ratios of the heights to the greatest widths, and an average of the respective ratios is between 2 and 5.

For some applications, the distal anchor is configured to contact the ventricular wall inferior to the target subannular space.

For some applications, the distal anchor is defined at least in part by at least one of the one or more wires.

For some applications, the ventricular anchor is configured to be atraumatic so as not to penetrate tissue of surrounding anatomy.

For some applications, the coaptation-assist device does not include any elements that are configured to penetrate tissue.

For some applications, the neo-leaflet is configured such that the coaptation surface is generally static throughout a cardiac cycle of the heart upon implantation of the coaptation-assist device in the heart.

For some applications, the neo-leaflet is configured such that the coaptation surface moves toward and away from the one or more opposing native leaflets during a cardiac cycle of the heart upon implantation of the coaptation-assist device in the heart.

For some applications, the coaptation surface has an area of between 2 and 20 cm2.

For some applications, at least half of the fingers terminate superiorly to an inferior edge of the surface of coaptation of the neo-leaflet.

For some applications, all of the fingers terminate superiorly to the inferior edge of the surface of coaptation of the neo-leaflet.

For some applications, the digitate anchor is serpentine, and is shaped so as to define a plurality of undulations having the plurality of curved superior peaks connected to a plurality of inferior troughs by respective segments.

For some applications, an average of respective greatest widths of the undulations, measured between adjacent pairs of the segments connected by respective curved superior peaks, is between 2 and 10 mm when the undulations are unconstrained.

For some applications, for at least one of the undulations, a radius of curvature of the curved superior peak is greater than a smallest width of the undulation, measured between adjacent pairs of the segments connected by the curved superior peaks, when the undulations are unconstrained.

For some applications, when the undulations are unconstrained:

the undulations have respective greatest widths and respective heights, the greatest widths measured between adjacent pairs of the segments connected by respective curved peaks, the respective heights measured in a superior-inferior direction, the undulations have respective ratios of the heights to the greatest widths, and an average of the respective ratios is between 2 and 5.

For some applications, at least half of the inferior troughs terminate superiorly to an inferior edge of the surface of coaptation of the neo-leaflet.

For some applications, all of the inferior troughs terminate superiorly to the inferior edge of the surface of coaptation of the neo-leaflet.

For some applications, the at least one of the one or more wires that defines the distal anchor is shaped as a distal wire loop.

For some applications, two longitudinal superior portions of the distal wire loop are fixed to each other.

For some applications, the distal wire loop is configured to be positioned in the ventricle, extending to a ventricular apical area.

For some applications, the distal wire loop is configured to remain anchored in position against the ventricular wall and one or more ventricular papillary muscles of the ventricular apical area, when the distal anchor is positioned partially against the ventricular wall outside the target subannular space.

For some applications, the distal wire loop is shaped so as to define three or more lobes.

For some applications, the distal wire loop is shaped so as to define exactly three lobes.

For some applications, respective lengths of the lobes are greater than respective widths of the lobes.

For some applications, the respective lengths of the lobes are greater than twice the respective widths of the lobes.

For some applications, when the lobes are unconstrained:

the lobes are shaped so as to define respective best-fit planes, and at least two of the best-fit-planes are not coplanar with one another.

For some applications, the distal wire loop is configured to remain anchored in position by force applied by the distal wire loop to surrounding anatomy.

For some applications, the distal wire loop is configured to remain anchored in position by radially-outwardly-directed force applied by the distal wire loop to the surrounding anatomy.

For some applications, the distal wire loop is configured to remain anchored in position by friction between the distal wire loop and surrounding anatomy.

For some applications:

the distal wire loop is a first distal wire loop, and the at least one of the one or more wires that defines the distal anchor are shaped so as to define a second distal wire loop that is configured to be positioned partially in at least one opposing-leaflet subannular space defined by at least one of the one or more opposing native leaflets, when the distal anchor is positioned partially against the ventricular wall outside the target subannular space.

For some applications, the second distal wire loop extends directly from the neo-leaflet.

For some applications, the distal wire loop is configured to be positioned partially in at least one opposing-leaflet subannular space defined by at least one of the one or more opposing native leaflets, when the distal anchor is positioned partially against the ventricular wall outside the target subannular space.

For some applications, the distal wire loop extends directly from the neo-leaflet.

For some applications, the distal wire loop is shaped so as to define at least two lobes, which are configured to be positioned partially in at two respective opposing-leaflet subannular spaces respectively defined by two of the one or more opposing native leaflets, when the distal anchor is positioned partially against the ventricular wall outside the target subannular space.

For some applications, a continuous portion of the one or more wires is shaped so as to define both the distal anchor and the proximal subannular anchor.

For some applications, the portion of the at least one of the one or more wires that defines the distal anchor is shaped as a distal wire loop.

For some applications, the proximal subannular anchor is configured such that, when the proximal subannular anchor is positioned at least partially in the target subannular space, the digitate anchor applies a force to a ventricular surface of the target native leaflet, so as to help anchor the ventricular anchor to the target native leaflet.

For some applications:

the coaptation-assist device further includes an atrial-surface support, which is configured to be disposed below an annulus of the native atrioventricular valve and against an atrial surface of the target native leaflet when the proximal subannular anchor is positioned at least partially in the target subannular space, the atrial-surface support and the digitate anchor are configured to grasp and sandwich at least a portion of the target native leaflet, in order to support the neo-leaflet, and to orient the neo-leaflet with respect to the native atrioventricular valve.

For some applications, a continuous portion of the one or more wires is shaped so as to define the proximal subannular anchor and at least partially define the atrial-surface support.

For some applications, the atrial-surface support includes a frame and an atrial-surface cover, which is coupled to the frame.

For some applications, the native atrioventricular valve is a tricuspid valve, and the neo-leaflet is configured to at least partially replace function of the target native leaflet by providing a surface of coaptation for the one or more opposing native leaflets of the tricuspid valve, when anchored in place by the ventricular anchor.

For some applications, the target native leaflet is a native septal leaflet of the tricuspid valve, the ventricular wall is a ventricular septal wall, and the neo-leaflet is configured to at least partially replace function of the septal leaflet by providing a surface of coaptation for one or more of the opposing native posterior and anterior leaflets of the tricuspid valve, when anchored in place by the ventricular anchor.

For some applications, the native atrioventricular valve is a mitral valve, and the neo-leaflet is configured to at least partially replace function of the target native leaflet by providing a surface of coaptation for the opposing native leaflet of the mitral valve, when anchored in place by the ventricular anchor.

For some applications, the target native leaflet is a native anterior leaflet of the mitral valve, the ventricular wall is a ventricular septal wall, and the neo-leaflet is configured to at least partially replace function of the native anterior leaflet by providing a surface of coaptation for an opposing native posterior leaflet of the mitral valve, when anchored in place by the ventricular anchor.

For some applications, the coaptation-assist device is configured such that the coaptation surface of the neo-leaflet crosses from an atrial side to a ventricular side of a native valvular plane, when anchored in place by the ventricular anchor.

For some applications, the neo-leaflet includes:

a neo-leaflet wire loop that defines at least a portion of a border of the neo-leaflet; and a neo-leaflet cover, which is attached to the neo-leaflet wire loop and provides the surface of coaptation.

For some applications, a portion of the neo-leaflet wire loop is recessed away from the border of the neo-leaflet along a central portion of an inferior edge of the neo-leaflet cover, such that the neo-leaflet cover defines a flap bordered by the recessed portion of the neo-leaflet wire loop and the central portion of the inferior edge of the neo-leaflet cover when the neo-leaflet is not constrained.

For some applications, the recessed portion of the neo-leaflet wire loop is curved when the neo-leaflet is not constrained.

For some applications, the central portion of the inferior edge of the neo-leaflet cover extends at least as inferiorly as a most-inferior portion of the neo-leaflet wire loop when the neo-leaflet is not constrained.

For some applications, the coaptation-assist device further includes a pouch, which is configured to inflate by blood flow during a cardiac cycle of the heart, so as to push the coaptation-assist device against one or more of: a ventricular surface of the target native leaflet and an annulus of the native atrioventricular valve, thereby stabilizing the coaptation-assist device with respect to the native atrioventricular valve.

For some applications, a system is provided that further includes a delivery tube in which the coaptation-assist device is removably disposed in a compressed configuration for minimally-invasive or percutaneous delivery to the heart.

There is further provided, in accordance with an application of the present invention, a coaptation-assist device for treating a native atrioventricular valve of a heart (or an aortic valve, or a pulmonary valve), the coaptation-assist device including:

a ventricular anchor, which includes one or more wires, and which is configured to be positioned in a ventricle of the heart; and a neo-leaflet, which is supported by the ventricular anchor and is configured to at least partially replace function of a target native leaflet of the native atrioventricular valve by providing a surface of coaptation for one or more opposing native leaflets that oppose the target native leaflet, when anchored in place by the ventricular anchor, wherein the ventricular anchor includes a distal anchor, which is shaped as a distal wire loop that (a) is defined at least in part by at least one of the one or more wires, and (b) is configured to be positioned partially in at least one opposing-leaflet subannular space defined by at least one of the one or more opposing native leaflets.

For some applications, the distal wire loop extends directly from the neo-leaflet when positioned partially in the at least one opposing-leaflet subannular space.

For some applications, the distal wire loop is shaped so as to define at least two lobes, which are configured to be positioned partially in at two respective opposing-leaflet subannular spaces respectively defined by two of the one or more opposing native leaflets.

For some applications, the distal wire loop is configured to remain anchored in position by radially-outwardly-directed force applied by the distal wire loop to surrounding anatomy.

For some applications, the distal wire loop is configured to remain anchored in position by friction between the distal wire loop and surrounding anatomy.

For some applications, the ventricular anchor is configured to be atraumatic so as not to penetrate tissue of surrounding anatomy.

For some applications, the coaptation-assist device does not include any elements that are configured to penetrate tissue.

For some applications, the neo-leaflet is configured such that the coaptation surface is generally static throughout a cardiac cycle of the subject upon implantation of the coaptation-assist device in the heart.

For some applications, the neo-leaflet is configured such that the coaptation surface moves toward and away from the one or more opposing native leaflets during a cardiac cycle of the subject upon implantation of the coaptation-assist device in the heart.

For some applications, the coaptation surface has an area of between 2 and 20 cm2.

For some applications, two longitudinal superior portions of the distal wire loop are fixed to each other.

For some applications:

the distal wire loop is a first distal wire loop, and the at least one of the one or more wires that defines the distal anchor is shaped so as to define a second distal wire loop that is configured to be positioned extending to a ventricular apical area when the first distal wire loop is positioned partially in the at least one opposing-leaflet subannular space.

For some applications, the second distal wire loop is configured to remain anchored in position against a ventricular wall and one or more ventricular papillary muscles of the ventricular apical area, when the first distal wire loop is positioned partially in the at least one opposing-leaflet subannular space.

For some applications, the second distal wire loop of the distal anchor is shaped so as to define three or more lobes.

For some applications, the second distal wire loop is shaped so as to define exactly three lobes.

For some applications, respective lengths of the lobes are greater than respective widths of the lobes.

For some applications, the respective lengths of the lobes are greater than twice the respective widths of the lobes.

For some applications, the ventricular anchor further includes a proximal subannular anchor, which is configured to be positioned at least partially in a target subannular space defined by the target native leaflet and a superior portion of a ventricular wall of the ventricle.

For some applications, the ventricular anchor is shaped as a distal wire loop that defines the proximal subannular anchor and the distal anchor.

For some applications, the native atrioventricular valve is a tricuspid valve, and the neo-leaflet is configured to at least partially replace function of the target native leaflet by providing a surface of coaptation for the one or more opposing native leaflets of the tricuspid valve, when anchored in place by the ventricular anchor.

For some applications, the target native leaflet is a native septal leaflet of the tricuspid valve, the ventricular wall is a ventricular septal wall, and the neo-leaflet is configured to at least partially replace function of the septal leaflet by providing a surface of coaptation for one or more of the opposing native posterior and anterior leaflets of the tricuspid valve, when anchored in place by the ventricular anchor.

For some applications, the native atrioventricular valve is a mitral valve, and the neo-leaflet is configured to at least partially replace function of the target native leaflet by providing a surface of coaptation for the opposing native leaflet of the mitral valve, when anchored in place by the ventricular anchor.

For some applications, the target native leaflet is a native anterior leaflet of the mitral valve, the ventricular wall is a ventricular septal wall, and the neo-leaflet is configured to at least partially replace function of the native anterior leaflet by providing a surface of coaptation for an opposing native posterior leaflet of the mitral valve, when anchored in place by the ventricular anchor.

For some applications, the coaptation-assist device is configured such that the coaptation surface of the neo-leaflet crosses from an atrial side to a ventricular side of a native valvular plane, when anchored in place by the ventricular anchor.

For some applications, a system is provided that further includes a delivery tube in which the coaptation-assist device is removably disposed in a compressed configuration for minimally-invasive or percutaneous delivery to the heart.

There is still further provided, in accordance with an application of the present invention, a coaptation-assist device for treating a native atrioventricular valve of a heart (or an aortic valve, or a pulmonary valve), the coaptation-assist device including:

a ventricular anchor, which is configured to be positioned in a ventricle of the heart; and a neo-leaflet, which (a) is supported by the ventricular anchor and is configured to at least partially replace function of a target native leaflet of the native atrioventricular valve by providing a surface of coaptation for one or more opposing native leaflets that oppose the target native leaflet, when anchored in place by the ventricular anchor, and (b) includes:

a neo-leaflet wire loop that defines at least a portion of a border of the neo-leaflet; and a neo-leaflet cover, which is attached to the neo-leaflet wire loop and provides the surface of coaptation, wherein a portion of the neo-leaflet wire loop is recessed away from the border of the neo-leaflet along a central portion of an inferior edge of the neo-leaflet cover, such that the neo-leaflet cover defines a flap bordered by the recessed portion of the neo-leaflet wire loop and the central portion of the inferior edge of the neo-leaflet cover when the neo-leaflet is not constrained.

For some applications, the recessed portion of the neo-leaflet wire loop is curved when the neo-leaflet is not constrained.

For some applications, the flap has an area of at least 10 mm2 when the neo-leaflet is not constrained.

For some applications, an area of the flap equals at least 15% of an area of the neo-leaflet cover when the neo-leaflet is not constrained.

For some applications, the central portion of the inferior edge of the neo-leaflet cover has a length, measured along the inferior edge, of between 5 and 40 mm when the neo-leaflet is not constrained.

For some applications, the central portion of the inferior edge of the neo-leaflet cover extends at least as inferiorly as a most-inferior portion of the neo-leaflet wire loop when the neo-leaflet is not constrained.

For some applications, when the neo-leaflet is not constrained, the central portion of the inferior edge of the neo-leaflet cover is curved and convex, and extends more inferiorly than the most-inferior portion of the neo-leaflet wire loop.

There is additionally provided, in accordance with an application of the present invention, a coaptation-assist device for treating a native aortic valve of a subject, the coaptation-assist device including:

a loop-shaped aortic anchor, which includes an anchor-loop wire loop, which (i) defines at least a portion of a border of the loop-shaped aortic anchor, and (ii) is configured (a) to be positioned in an ascending aorta and (b) to remain anchored in position against an aortic wall;

an aortic-sinus anchor, which is configured to be positioned at least partially in an aortic sinus of a target native aortic leaflet; and a neo-leaflet, which is supported by the loop-shaped aortic anchor and the aortic-sinus anchor and is configured to at least partially replace function of the target native aortic leaflet by providing a surface of coaptation for one or more opposing native leaflets that oppose the target native aortic leaflet, when anchored in place by the loop-shaped aortic anchor and the aortic-sinus anchor.

For some applications, the loop-shaped aortic anchor is configured to remain anchored in position by force applied by the anchor-loop wire loop to the aortic wall.

For some applications, the loop-shaped aortic anchor is configured to remain anchored in position by radially-outwardly-directed force applied by the anchor-loop wire loop to the aortic wall.

For some applications, the loop-shaped aortic anchor is configured to remain anchored in position by friction and radial force between the anchor-loop wire loop and the aortic wall.

For some applications, the loop-shaped aortic anchor is configured to be atraumatic so as not to penetrate tissue of the aortic wall.

For some applications, the coaptation-assist device does not include any elements that are configured to penetrate tissue.

For some applications, the coaptation-assist device includes one or more wires, and a continuous portion of the one or more wires is shaped so as to define both the loop-shaped aortic anchor and the aortic-sinus anchor.

For some applications, the aortic-sinus anchor is configured such that, when the aortic-sinus anchor is positioned at least partially in the aortic sinus, the aortic-sinus anchor applies a force to sinus-facing surface of the target native aortic leaflet, so as to help anchor the aortic-sinus anchor to the target native aortic leaflet.

For some applications, the aortic-sinus anchor includes a digitate anchor that is shaped so as to define a plurality of fingers having a plurality of curved inferior peaks that point in an inferior direction and engage one or more sinus surfaces selected from the group consisting of: an aortic wall, a sinus-facing surface of the target native aortic leaflet, and a floor of the aortic sinus.

For some applications:

the coaptation-assist device further includes a leaflet-surface support, which is configured to be disposed centrally to the target native aortic valve and against a coapting surface of the target native aortic leaflet when the aortic-sinus anchor is positioned at least partially in the aortic sinus, and the leaflet-surface support and the aortic-sinus anchor are configured to grasp and sandwich at least a portion of the target native aortic leaflet, in order to support the neo-leaflet.

For some applications, the leaflet-surface support includes a frame and a cover, which is coupled to the frame.

For some applications, a system is provided that further includes a delivery tube in which the coaptation-assist device is removably disposed in a compressed configuration for minimally-invasive or percutaneous delivery to the ascending aorta.

There is yet additionally provided, in accordance with an application of the present invention, a method for treating a native atrioventricular valve of a heart (or an aortic valve, or a pulmonary valve), the method including:

advancing, to within the heart, a coaptation-assist device that includes a ventricular anchor, which includes (a) one or more wires, (b) a proximal subannular anchor, which includes a digitate anchor that (i) is defined at least in part by at least one of the one or more wires, and (ii) is shaped so as to define a plurality of fingers having a plurality of curved superior peaks, and (c) a distal anchor;

positioning the ventricular anchor in a ventricle of the heart such that:

the proximal subannular anchor is positioned at least partially in a target subannular space defined by a target native leaflet of the native atrioventricular valve and a superior portion of a ventricular wall of the ventricle, such that (i) the curved superior peaks point in a superior direction and engage a subannular surface of the target native leaflet, and (ii) one or more of the fingers engage chordae tendineae that extend between the target native leaflet and the superior portion of the ventricular wall, so as to stabilize the coaptation-assist device, the distal anchor is positioned partially against the ventricular wall outside the target subannular space, so as to push on the proximal subannular anchor to help anchor the proximal subannular anchor in place within the target subannular space; and positioning a neo-leaflet of the coaptation-assist device such that the neo-leaflet at least partially replaces function of the target native leaflet by providing a surface of coaptation for one or more opposing native leaflets that oppose the target native leaflet, when supported and anchored in place by the ventricular anchor.

There is also provided, in accordance with an application of the present invention, a method for treating a native atrioventricular valve of a heart (or an aortic valve, or a pulmonary valve), the method including:

advancing, to within the heart, a coaptation-assist device that includes a ventricular anchor, which includes one or more wires, and a distal anchor, which is shaped as a distal wire loop that is defined at least in part by at least one of the one or more wires;

positioning a neo-leaflet of the coaptation-assist device such that the neo-leaflet at least partially replaces function of a target native leaflet by providing a surface of coaptation for one or more opposing native leaflets that oppose the target native leaflet, when anchored in place by the ventricular anchor; and positioning the ventricular anchor in a ventricle of the heart such that the distal anchor is positioned partially in at least one opposing-leaflet subannular space defined by at least one of the one or more opposing native leaflets.

For some applications, the distal wire loop is shaped so as to define at least two lobes, and positioning the ventricular anchor in the ventricle includes positioning the ventricular anchor in the ventricle such that the at least two lobes are positioned partially in at two respective opposing-leaflet subannular spaces respectively defined by two of the one or more opposing native leaflets.

For some applications, the ventricular anchor further includes a proximal subannular anchor, and positioning the ventricular anchor in the ventricle includes positioning the ventricular anchor in the ventricle such that the proximal subannular anchor is positioned at least partially in a target subannular space defined by the target native leaflet and a superior portion of a ventricular wall of the ventricle.

There is further provided, in accordance with an application of the present invention, a method for treating a native atrioventricular valve of a heart (or an aortic valve, or a pulmonary valve), the method including:

positioning a ventricular anchor of a coaptation-assist device in a ventricle of the heart; and positioning a neo-leaflet of the coaptation-assist device such that the neo-leaflet at least partially replaces function of a target native leaflet of the native atrioventricular valve by providing a surface of coaptation for one or more opposing native leaflets that oppose the target native leaflet, when supported by and anchored in place by the ventricular anchor, the neo-leaflet including:

a neo-leaflet wire loop that defines at least a portion of a border of the neo-leaflet; and a neo-leaflet cover, which is attached to the neo-leaflet wire loop and provides the surface of coaptation, wherein a portion of the neo-leaflet wire loop is recessed away from the border of the neo-leaflet along a central portion of an inferior edge of the neo-leaflet cover, such that the neo-leaflet cover defines a flap bordered by the recessed portion of the neo-leaflet wire loop and the central portion of the inferior edge of the neo-leaflet cover when the neo-leaflet is not constrained.

There is still further provided, in accordance with an application of the present invention, a method for treating a native aortic valve of a subject, the method including:

positioning a loop-shaped aortic anchor of a coaptation-assist device in an ascending aorta, such that an anchor-loop wire loop of the loop-shaped aortic anchor remains anchored in position against an aortic wall, wherein the anchor-loop wire loop defines at least a portion of a border of the loop-shaped aortic anchor;

positioning an aortic-sinus anchor of the coaptation-assist device at least partially in an aortic sinus of a target native aortic leaflet; and positioning a neo-leaflet of the coaptation-assist device such that the neo-leaflet at least partially replaces function of the target native leaflet by providing a surface of coaptation for one or more opposing native aortic leaflets that oppose the target native aortic leaflet, when anchored in place by the loop-shaped aortic anchor and the aortic-sinus anchor.

There is additionally provided, in accordance with an application of the present invention, a method for treating a native pulmonary valve of a subject, the method including:

positioning a loop-shaped pulmonary-artery anchor of a coaptation-assist device in an pulmonary artery, such that an anchor-loop wire loop of the loop-shaped pulmonary-artery remains anchored in position against a pulmonary wall, wherein the anchor-loop wire loop defines at least a portion of a border of the loop-shaped pulmonary-artery anchor;

positioning a pulmonary-sinus anchor of the coaptation-assist device at least partially in a pulmonary sinus of a target native pulmonary leaflet; and positioning a neo-leaflet of the coaptation-assist device such that the neo-leaflet at least partially replaces function of the target native leaflet by providing a surface of coaptation opposing one or more native pulmonary leaflets that oppose the target native pulmonary leaflet, when anchored in place by the loop-shaped pulmonary-artery anchor and the pulmonary-sinus anchor.

The present invention will be more fully understood from the following detailed description of embodiments thereof, taken together with the drawings, in which:

BRIEF DESCRIPTION OF THE DRAWINGS

FIGS. 8A-D are schematic illustrations of implantations of the coaptation-assist device of FIGS. 5A-E in a heart, in accordance with an application of the present invention;

DETAILED DESCRIPTION OF APPLICATIONS

Figure 1A:
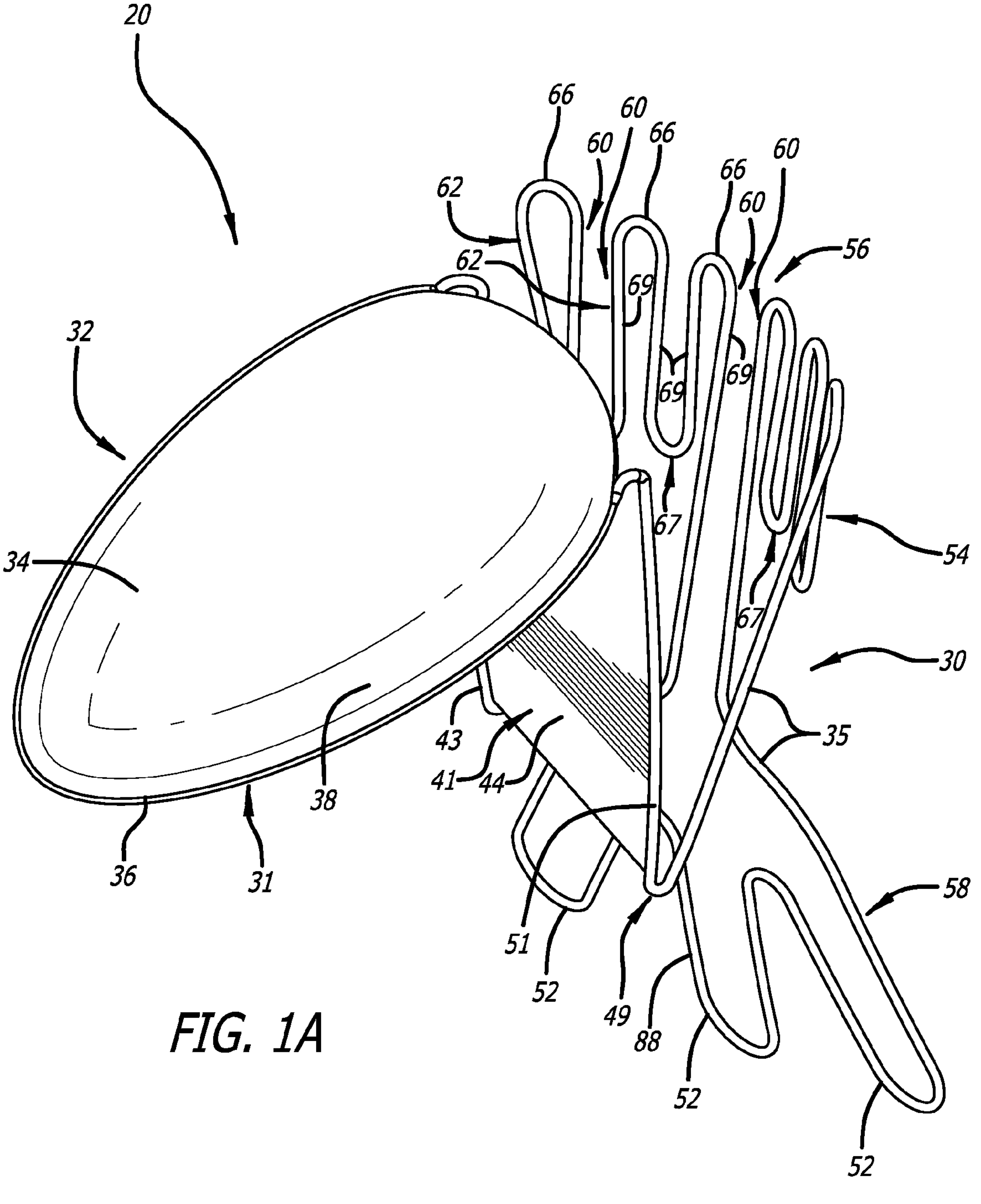
FIGS. 1A-C are schematic illustrations of a coaptation-assist device for treating a native atrioventricular valve of a subject, in accordance with an application of the present invention.
Figure 1B:
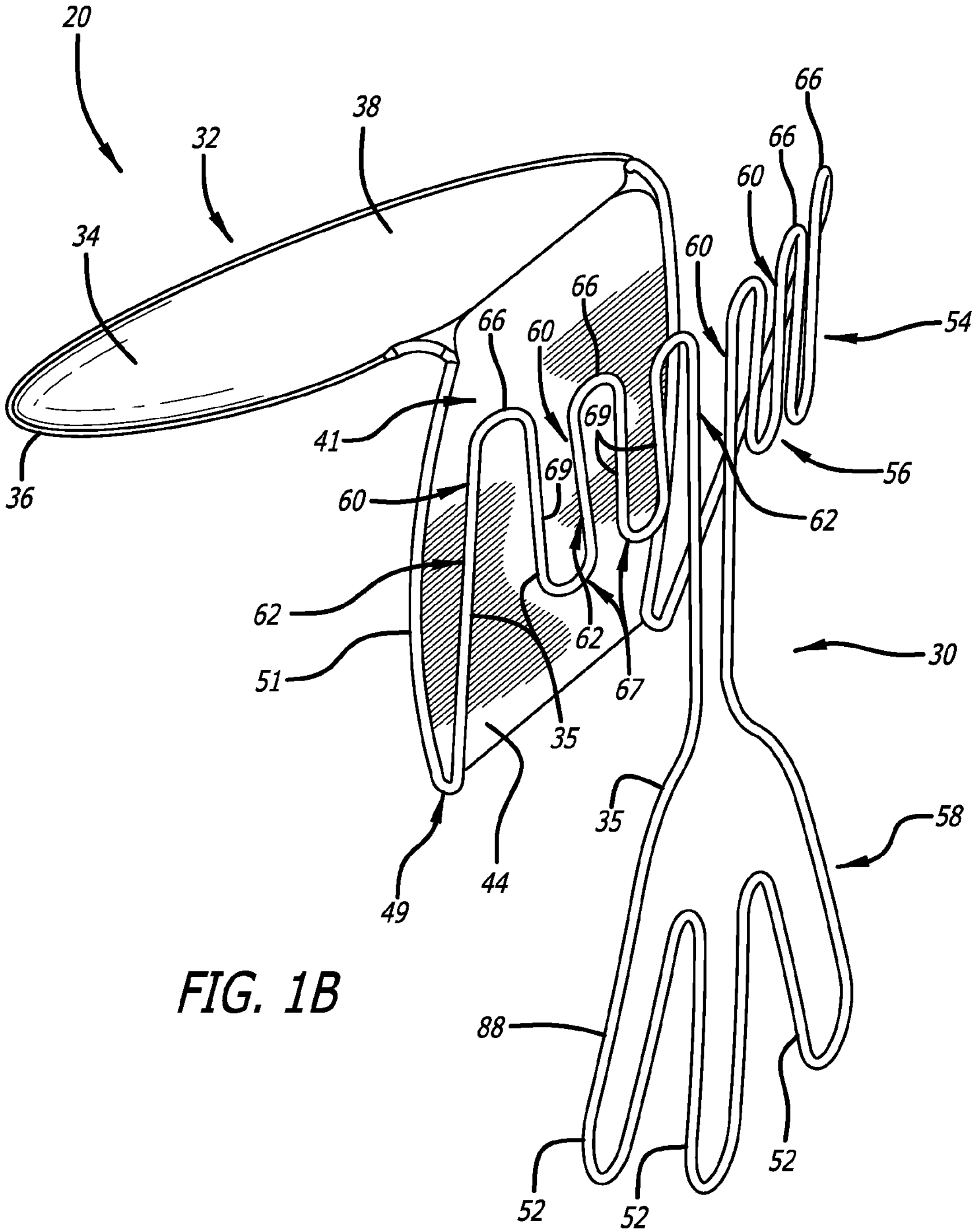
Figure 1C:
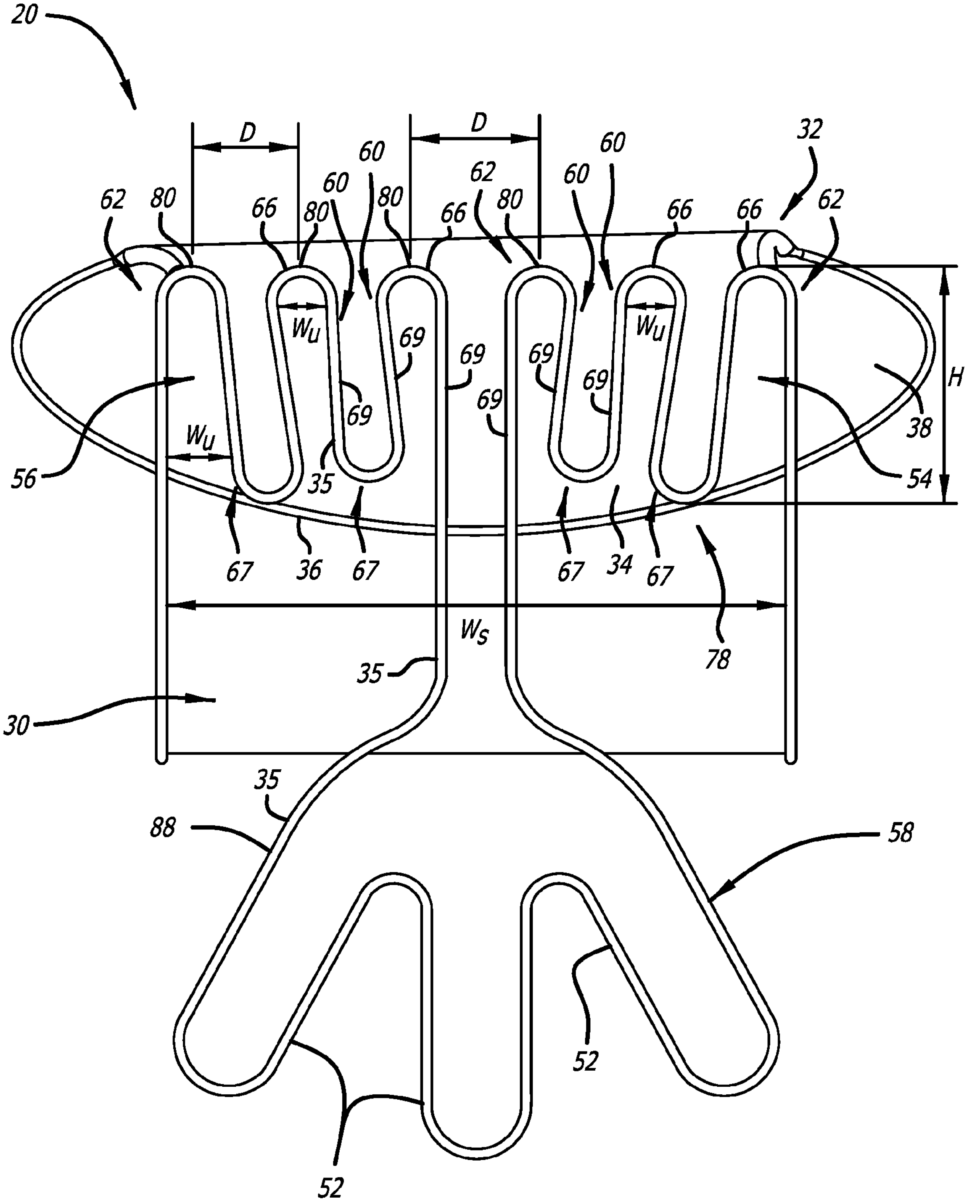

FIGS. 1A-C are schematic illustrations of a coaptation-assist device 20 for treating a native atrioventricular valve 22 of a subject, in accordance with an application of the present invention. Typically, the native atrioventricular valve suffers from a valvular pathology, such as functional mitral or tricuspid regurgitation, often characterized by lack of mobility of the leaflets in the valve.

Figure 2:
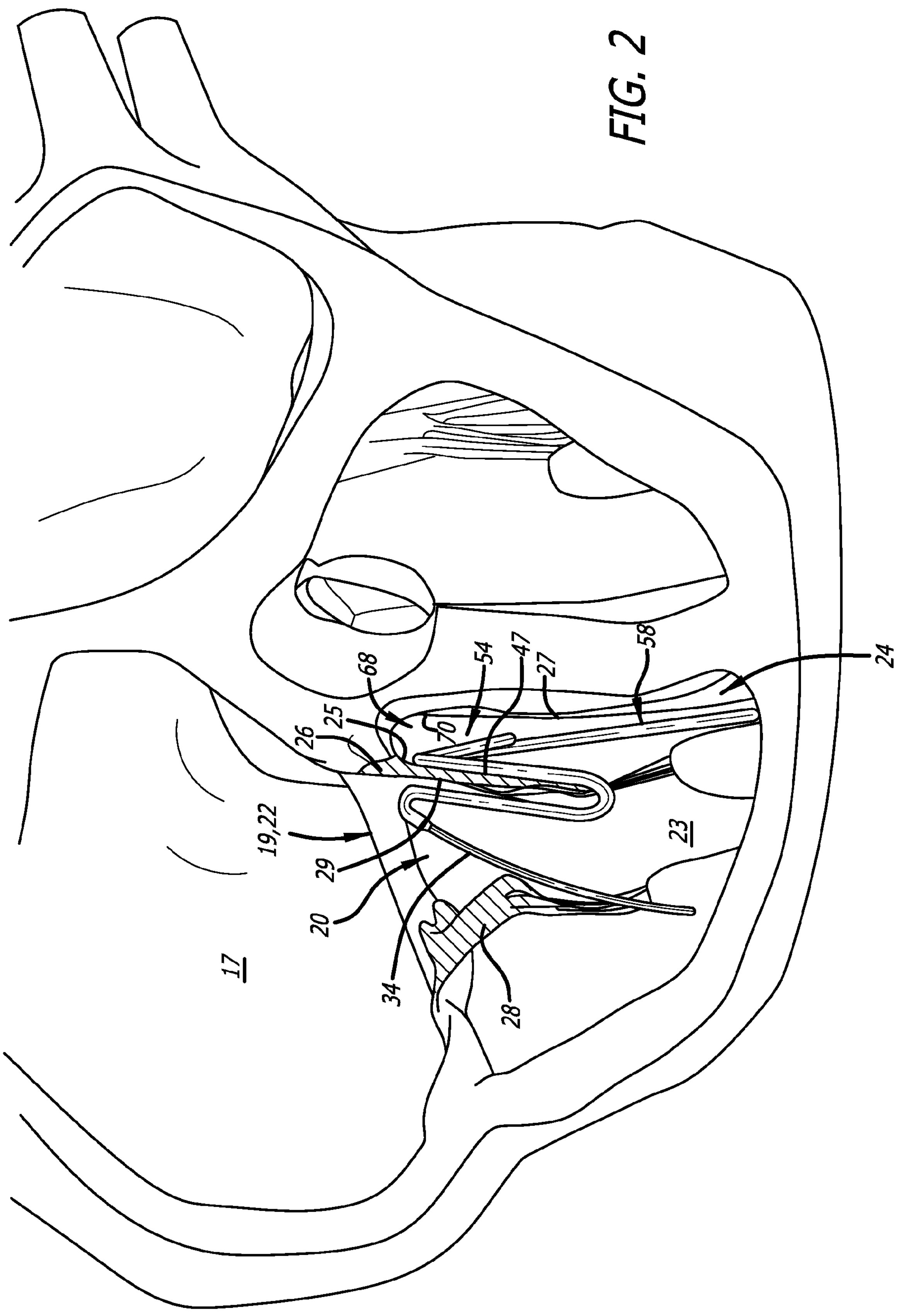
FIG. 2 is a schematic illustration of the coaptation-assist device of FIGS. 1A-C implanted in a native valve, in accordance with an application of the present invention.

Reference is additionally made to FIG. 2, which is a schematic illustration of coaptation-assist device 20 implanted in native valve 22, in accordance with an application of the present invention. In the particular implantation shown in FIG. 2, native valve 22 is a tricuspid valve 19. FIG. 2 is a cross-sectional view of the heart, with an anterior portion of the heart, including the native anterior leaflet of tricuspid valve 19, removed, such that only the septal and posterior leaflets are shown.

Coaptation-assist device 20 comprises a ventricular anchor 30 and a neo-leaflet 32. Ventricular anchor 30 is configured to be positioned in a ventricle 23 of the heart. Neo-leaflet 32 is supported by ventricular anchor 30. As used in the present application, including in the claims and Inventive concepts, the term "neo-leaflet" means "prosthetic leaflet."

For some applications, coaptation-assist device 20 does not comprise any elements that are configured to penetrate (e.g., pierce) tissue. For other applications, coaptation-assist device 20 comprises at least one element that is configured to penetrate tissue (configuration not shown).

Typically, ventricular anchor 30 is configured to be atraumatic so as not to penetrate (e.g., pierce) tissue of the surrounding anatomy. To this end, ventricular anchor 30 typically does not comprise any exposed sharp elements that might penetrate tissue.

Neo-leaflet 32 is configured to at least partially replace function of a target native leaflet 26 of native atrioventricular valve 22 by providing a surface of coaptation 34 for one or more opposing native leaflets 28 that oppose target native leaflet 26, when anchored in place by ventricular anchor 30, such as shown in FIG. 2. Neo-leaflet 32 is typically configured to cover at least a portion of target native leaflet 26.

For some applications, coaptation surface 34 has an area of at least 2 cm2 (e.g., at least 10 cm2), no more than 20 cm2 (e.g., no more than 15 cm2), and/or between 2 cm (e.g., 10 cm2) and 20 cm2 (e.g., 15 cm2). The other coaptation surfaces described hereinbelow may also have these areas.

For some applications, neo-leaflet 32 comprises a neo-leaflet wire loop 36 that defines at least a portion of a border 31 of the neo-leaflet (by running along or near border 31, e.g., within 2 mm of border 31). Neo-leaflet 32 further comprises a neo-leaflet cover 38 attached to neo-leaflet wire loop 36. Typically, neo-leaflet cover 38 provides the above-mentioned coaptation surface 34. For some applications, neo-leaflet cover 38 comprises one or more biocompatible thin sheets of material, which may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium). Neo-leaflet wire loop 36 may be shaped as a closed loop or an open loop, which is open on a proximal side in the direction of distal anchor 58 (e.g., distal wire loop 88), described hereinbelow. Neo-leaflet wire loop 36 comprises metal or another semi-rigid material. The material of neo-leaflet wire loop 36 is either self-expanding or mechanically expandable. For example, neo-leaflet wire loop 36 may comprise a shape-memory alloy, such as Nitinol. For some applications, neo-leaflet wire loop 36 is fabricated by shaping one or more wires. For other applications, neo-leaflet wire loop 36 is fabricated by wire coiling featuring fixed or variable characteristics along the loop length, including one or more of outside diameter, pitch spacing, and stiffness. For some applications, the wire of neo-leaflet wire loop 36 is circular in cross-section; alternatively, the wire has another cross-sectional shape, such as elliptical, rectangular, or generally flat. For still other applications, neo-leaflet wire loop 36 is fabricated by laser-cutting and shaping a tube or a flat shape sheet of metal, such as a shape memory alloy, e.g., Nitinol.

For some applications, neo-leaflet 32 has an intrinsic stiffness provided by the material of neo-leaflet wire loop 36 and/or neo-leaflet cover 38. Alternatively or additionally, neo-leaflet 32 comprises one or more stiffening elements within neo-leaflet cover 38 of the neo-leaflet to prevent the neo-leaflet from prolapsing in the atrial chamber as a result of an increase of backflow pressure over the neo-leaflet's ventricular surface during the cardiac cycle.

As mentioned above, for some applications, such as shown in FIG. 2, native valve 22 is tricuspid valve 19. For these applications, neo-leaflet 32 is configured to at least partially replace function of target native leaflet 26 by providing coaptation surface 34 for one or more opposing native leaflets 28 of tricuspid valve 19, when anchored in place by ventricular anchor 30. For some of these applications, target native leaflet 26 is a native septal leaflet of tricuspid valve 19, ventricular wall 27 (described hereinbelow) is a ventricular septal wall, and neo-leaflet 32 is configured to at least partially replace function of the septal leaflet by providing coaptation surface 34 for one or more of the opposing native posterior and anterior leaflets of tricuspid valve 19, when anchored in place by ventricular anchor 30. Although in the cross-sectional view of the heart in FIG. 2, the only opposing native leaflet 28 that is shown is the posterior native leaflet, the opposing anterior native leaflet also coapts with coaptation surface 34 when it partially replaces the septal leaflet.

For other applications (configuration not shown), native valve 22 is a mitral valve, and neo-leaflet 32 is configured to at least partially replace function of target native leaflet 26 (either a native posterior leaflet or a native anterior leaflet) by providing a coaptation surface 34 for the opposing native leaflet of the mitral valve, when anchored in place by ventricular anchor 30. For some of these applications, target native leaflet 26 is the native anterior leaflet of the mitral valve, ventricular wall 27 (described hereinbelow) is a ventricular septal wall, and neo-leaflet 32 is configured to at least partially replace function of the native anterior leaflet by providing coaptation surface 34 for the opposing native posterior leaflet of the mitral valve, when anchored in place by ventricular anchor 30.

Reference is still made to FIGS. 1A-C and 2. Ventricular anchor 30 comprises one or more wires 35. The one or more wires 35 comprise metal or another semi-rigid material. The wires may be conventional wires, or may be fabricated by laser-cutting and shaping a tube or a flat shape sheet of metal. The material of the one or more wires 35 is either self-expanding or mechanically expandable. For example, the one or more wires 35 may comprise a shape-memory alloy, such as Nitinol. For some applications, the one or more wires 35 are coated.

Ventricular anchor 30 comprises a proximal subannular anchor 54 and, typically, a distal anchor 58. Alternatively, for some applications, ventricular anchor 30 does not comprise distal anchor 58, and is instead anchored in place only by sandwiching at least a portion of atrial and ventricular surfaces of target native leaflet 26, such as described hereinbelow with reference to FIGS. 1A-C and 2.

Proximal subannular anchor 54 comprises a digitate anchor 56 that is defined at least in part by at least one of the one or more wires 35. Digitate anchor 56 is shaped so as to define a plurality of fingers 60 having a plurality of curved superior peaks 66. As used in the present application, including in the claims, a "finger" is an elongate, narrow projection, and "digitate" means having digits or fingerlike projections.

Alternatively, proximal subannular anchor 54 does not comprise digitate anchor 56.

For some applications, such as shown, digitate anchor 56 is serpentine, and is shaped so as to define a plurality of undulations 62 having the plurality of curved superior peaks 66 connected to a plurality of inferior troughs 67 by respective segments 69, which are generally aligned in a superior-anterior and/or diagonal direction. Inferior troughs 67 are typically curved. Undulations 62 define fingers 60, respectively. Alternatively, for some applications, digitate anchor 56 is not serpentine, i.e., does not define troughs; for example, inferior ends of fingers 60 may be connected to a horizontal (i.e., laterally-oriented) portion of wire 35 of digitate anchor 56 (configuration not shown).

For some applications, fingers 60 are covered partially or entirely with one or more biocompatible thin sheets of material. Typically, the one or more biocompatible thin sheets of material are soft and atraumatic. The one or more biocompatible thin sheets of material may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium), or an electospun material.

Proximal subannular anchor 54 is configured to be positioned at least partially in a target subannular space 68 defined by target native leaflet 26 and a superior portion 70 of a ventricular wall 27. In other words, proximal subannular anchor 54 is configured to be secured underneath and behind target native leaflet 26, in contact with a subannular surface 25 of target native leaflet 26.

In particular, proximal subannular anchor 54 is configured to be positioned at least partially in target subannular space 68 such that:

- curved superior peaks 66 point in a superior direction and engage a subannular surface 25 of target native leaflet 26; and
- one or more of fingers 60 engage chordae tendineae 76 that extend between target native leaflet 26 and superior portion 70 of ventricular wall 27, so as to stabilize coaptation-assist device 20, including, in particular, neo-leaflet 32.

Fingers 60 are sufficiently narrow such that they pass around and between chordae tendineae 76 during advancement of digitate anchor 56 from the ventricular area in a superior direction into and within target subannular space 68. Optionally, fingers 60 are also sufficiently flexible such that they reposition themselves as necessary around and between chordae tendineae 76 during advancement of digitate anchor 56 in the superior direction into and within target subannular space 68.

To this end, typically:

- digitate anchor 56 is shaped so as to define fingers 60 having at least two, no more than twenty, and/or between two and twenty curved superior peaks 66, such as between two and twelve curved superior peaks, e.g., between four and twelve curved superior peaks, such as between six and twelve curved superior peaks, e.g., between six and eight curved superior peaks, and/or
- an average of respective greatest widths $W_U$ of fingers 60, measured laterally, is at least 2 mm, no more than 10 mm, and/or between 2 and 10 mm when fingers 60 are unconstrained, such as at least 3 mm, no more than 6 mm, and/or between 3 and 6 mm, as labeled in FIG. 1C.

For some applications in which digitate anchor 56 is serpentine, an average of respective greatest widths $W_U$ of undulations 62, measured between adjacent pairs of segments 69 connected by respective curved superior peaks 66, is at least 2 mm, no more than 10 mm, and/or between 2 and 10 mm when undulations 62 are unconstrained, such as at least 3 mm, no more than 6 mm, and/or between 3 and 6 mm, as labeled in FIG. 1C.

Typically, a portion of chordae tendineae 76 extend between a ventricular surface 82 of target native leaflet 26 and superior portion 70 of ventricular wall 27 (known in the art as secondary and tertiary chordae tendineae), and a portion of chordae tendineae 76 extend between a free edge 84 of target native leaflet 26 and superior portion 70 of ventricular wall 27 (known in the art as primary chordae tendineae).

For some applications:

- a greatest width $W_S$ of a portion 78 of digitate anchor 56 that defines fingers 60 is between 20 and 60 mm, such as between 25 and 40 mm, when fingers 60 are unconstrained,
- an average of respective distances D between midpoints 80 of curved superior peaks 66 of adjacent pairs of fingers 60 is at least 3 mm, no more than 9 mm, and/or between 3 and 9 mm when fingers 60 are unconstrained,
- an average of respective heights H of fingers 60 is at least 4 mm, no more than 30 mm, and/or between 4 and 30 mm, such as at least 8 mm, no more than 12 mm, and/or between 8 and 12 mm, the respective heights measured in a superior-inferior direction, when fingers 60 are unconstrained, and/or
- fingers 60 have respective ratios of the heights H to the greatest widths $W_U$, and an average of the respective ratios is at least 2, no more than 5, and/or between 2 and 5, when fingers 60 are unconstrained.

(As labeled in FIG. 1C, for applications in which digitate anchor 56 is serpentine, the above-mentioned respective heights H are measured between curved superior peaks 66 and adjacent curved inferior troughs 79 of fingers 60 in a superior-inferior direction, rather than a slanted direction directly between midpoints 80 of curved superior peaks 66 and midpoints 80 of curved inferior troughs 79.)

For some applications, an average of respective radii of curvature $R_C$ of curved superior peaks 66 is at least 1 mm, no more than 10 mm, and/or between 1 and 10 mm, such as at least 3 mm, no more than 6 mm, and/or between 3 and 6 mm, when fingers 60 are unconstrained.

For some applications, for at least one of fingers 60 (such as two or more, or all, of fingers 60), a radius of curvature $R_C$ of curved superior peak 66 is greater than a smallest width $W_M$ of finger 60, when fingers 60 are unconstrained. These relative dimensions may provide vertical integrity to digitate anchor 56. For some applications in which digitate anchor 56 is serpentine, for at least one of undulations 62 (such as two or more, or all, of undulations 62), radius of curvature $R_C$ of curved peak 66 is greater than a smallest width $W_M$ of undulation 62, when undulations 62 are unconstrained.

For some applications, respective distances D between midpoints 80 of curved superior peaks 66 of adjacent pairs of fingers 60 vary along a width of digitate anchor 56, when fingers 60 are unconstrained. For example, fingers 60 may be more concentrated in a central portion of the width of digitate anchor 56 than in a peripheral (i.e., commissural)

portion of the width of digitate anchor 56, or vice versa. This concentration may accommodate different chordal distribution in the center of the native leaflet, and may provide more flexibility to the commissural sides while keeping stability in the center. For other applications, all respective distances D between midpoints 80 of curved superior peaks 66 of adjacent pairs of fingers 60 equal one another, when fingers 60 are unconstrained.

For some applications, at least half of the fingers 60 (such as all of fingers 60) terminate superiorly to an inferior edge 86 of surface of coaptation 34 of neo-leaflet 32. For some applications in which digitate anchor 56 is serpentine, at least half of inferior troughs 79 (such as all of inferior troughs 79) terminate superiorly to an inferior edge 86 of surface of coaptation 34 of neo-leaflet 32.

For some applications, foam is provided at one or more of curved superior peaks 66 and/or at one or more of inferior troughs 67, which may provide more atraumatic contact between digitate anchor 56 and the subannular apparatus.

Distal anchor 58 is configured to be positioned partially against ventricular wall 27 outside target subannular space 68, so as to push on proximal subannular anchor 54 to help proximal subannular anchor 54 in place within target subannular space 68. For some applications, such as shown in FIGS. 1A-C and 2, distal anchor 58 is configured to contact ventricular wall 27 inferior to target subannular space 68.

For some applications, such as shown in FIGS. 1A-C and 2, distal anchor 58 is defined at least in part by at least one of the one or more wires 35.

For some these applications, the at least one of the one or more wires 35 that defines distal anchor 58 is shaped as a distal wire loop 88, which provides distal anchor 58 with a loop-shaped border. For some applications, distal wire loop 88 is fabricated by shaping the at least one of the one or more wires 35. For other applications, distal wire loop 88 is fabricated by wire coiling featuring fixed or variable characteristics along the loop length; the variable characteristics may include one or more of outside diameter, pitch spacing, and stiffness. For other applications, distal wire loop 88 is fabricated by laser-cutting and shaping a tube or a flat shape sheet of metal, such as a shape memory alloy, e.g., Nitinol.

For some applications, distal wire loop 88 is configured to be positioned in ventricle 23, extending to a ventricular apical area 24 (at the bottom of ventricle 23). Distal wire loop 88 is configured to remain anchored in position against surrounding anatomy, including subannular surface 25, a ventricular wall 27, and ventricular apical area 24, such as shown in FIG. 2. In other words, distal wire loop 88 is configured to be seated apically, and to be stabilized by ventricular wall 27. Typically, distal wire loop 88 is configured to pass behind or across ventricular papillary muscles 46 of ventricular apical area 24. Optionally, the surrounding anatomy against which distal wire loop 88 is anchored further includes one or more of the following: a moderator band, one or more chordae tendineae, and one or more papillary muscles on the opposite side of ventricle 23.

Typically, distal wire loop 88 is configured to remain anchored in position by force (typically radially-outwardly-directed force) applied by distal wire loop 88 to the surrounding anatomy, and/or by friction between distal wire loop 88 and the surrounding anatomy. For some applications, distal wire loop 88 comprises a self-expandable material, such as a shape-memory alloy (e.g., Nitinol) that causes distal wire loop 88 to expand radially outwardly so as to apply the force. For these applications, distal wire loop 88 typically is configured to have a shape in its resting (relaxed) state that is larger than the surrounding anatomy, such that the surrounding anatomy limits expansion of distal wire loop 88 and distal wire loop 88 applies a force to the surrounding anatomy (and vice versa). In addition, the narrowing of ventricular wall 27 in a subannular-to-apical direction compresses distal wire loop 88, creating a counter-radial force, and directing distal wire loop 88 to stabilize itself at the sub-leaflet ventricular hinge level (i.e., at the level of subannular surface 25).

For some applications, distal wire loop 88 is shaped so as to define three or more lobes 52, such as exactly three lobes 52, as shown in FIGS. 1A-C and 2. Lobes 52 may allow distal wire loop 88 to readily enter the wrinkled crevices defined by ventricular wall 27 at ventricular apical area 24. Typically, respective lengths of lobes 52 (measured in a generally superior-anterior direction) are greater than respective widths of lobes 52, e.g., greater than twice the respective widths of lobes 52.

For some applications, distal wire loop 88 has one or more of the following dimensions:

- an enclosed (surrounded) area of at least 2 cm2, no more than 60 cm2, and/or between 2 and 60 cm2,
- a perimeter of at least 4 cm, no more than 15 cm, and/or between 4 and 15 cm,
- a length of at least 2 cm, no more than 12 cm, and/or between 2 and 12 cm, and/or
- a width of at least 1 cm, no more than 12 cm, and/or between 1 and 12 cm.

Distal wire loop 88 may define a plane or a curved surface.

For some applications, when lobes 52 are unconstrained, lobes 52 are shaped so as to define respective best-fit planes, and at least two of the best-fit-planes are not coplanar with one another. This configuration may provide stability to distal wire loop 88, by making it more difficult for distal wire loop 88 to slide sideways, which might occur if lobes 52 were instead aligned along the same plane. This configuration may also accommodate the width of the ventricular apex area, to expand across that area and increase stabilization.

Reference is still made to FIGS. 1A-C and 2. For some applications, a continuous portion of the one or more wires 35 is shaped so as to define both distal anchor 58 and digitate anchor 56, and, optionally additional portions of proximal subannular anchor 54.

For some of these applications, the portion of the at least one of the one or more wires 35 that defines distal anchor 58 is shaped as a distal wire loop 88, which may have any of the characteristics of distal wire loop 88 described hereinabove.

Reference is still made to FIGS. 1A-C and 2. For some applications, proximal subannular anchor 54 is configured such that, when proximal subannular anchor 54 is positioned at least partially in target subannular space 68, digitate anchor 56 applies a force to ventricular surface 82 of target native leaflet 26, so as to help anchor ventricular anchor 30 to target native leaflet 26, and typically so as to support and/or stabilize neo-leaflet 32, and so as to orient neo-leaflet 32 with respect to native valve 22. For example, this additional anchoring may help prevent neo-leaflet 32 from tilting toward one of the native commissures, and/or may help orient neo-leaflet 32 at a desired angle with respect to the native valvular plane.

For some of these applications, coaptation-assist device 20 further comprises an atrial-surface support 41, which is configured to be disposed below an annulus of native atrioventricular valve 22 and against an atrial surface 47 of target native leaflet 26 when proximal subannular anchor 54 is positioned at least partially in target subannular space 68. Atrial-surface support 41 and digitate anchor 56 are configured to grasp and sandwich at least a portion of target native leaflet 26, in order to support neo-leaflet 32, and to orient neo-leaflet 32 with respect to native atrioventricular valve 22.

For some applications, atrial-surface support 41 comprises a frame 51 and an atrial-surface cover 44, which is coupled to frame 51. Frame 51 comprises one or more wires 43. Typically, frame 51 defines at least a portion of a border of atrial-surface cover 44.

For some applications, atrial-surface cover 44 comprises one or more biocompatible thin sheets of material (optionally, the same one or more sheets of material (e.g., the same exactly one sheet of material) define both neo-leaflet cover 38, described above, and atrial-surface cover 44; alternatively, separate sheets of material define neo-leaflet cover 38 and atrial-surface cover 44). For some applications, atrial-surface cover 44 pushes against atrial surface 47 of target native leaflet 26 to prevent blood flow between target native leaflet 26 and the coaptation-assist device. Typically, the one or more biocompatible thin sheets of material are soft and atraumatic. The one or more biocompatible thin sheets of material may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium).

For some applications, a continuous portion of the one or more wires 35 is shaped so as to define proximal subannular anchor 54 and at least partially define atrial-surface support 41.

For some applications, neo-leaflet 32 is coupled to ventricular anchor 30 via atrial-surface support 41, such as shown in FIGS. 1A-C and 2. For some of these applications, coaptation-assist device 20 comprises a wire loop that is shaped so as to at least partially define neo-leaflet 32 and atrial-surface support 41, such as shown.

For some applications, coaptation-assist device 20 is shaped so as to define a fold 49 between atrial-surface support 41 and ventricular anchor 30. Fold 49 is configured to extend around the free edge of target native leaflet 26 when atrial-surface support 41 and digitate anchor 56 grasp and sandwich the at least a portion of target native leaflet 26.

Coaptation-assist device 20 may optionally be configured to implement any of the features of coaptation-assist device 20 described in International Application PCT/IL2020/050057, filed Jan. 14, 2020, with reference to FIGS. 1A-E and 2 thereof; this international application is incorporated herein by reference.

Reference is still made to FIGS. 1A-C and 2. For some applications, neo-leaflet 32 is configured such that coaptation surface 34 is generally static throughout a cardiac cycle of the subject upon implantation of coaptation-assist device 20 in a heart of the subject. In these applications, coaptation is provided by motion of the one or more opposing native leaflets 28 against the generally static coaptation surface 34 provided by neo-leaflet 32. For example, to achieve this general stasis, neo-leaflet wire loop 36 and/or neo-leaflet cover 38 of neo-leaflet 32 may be relatively stiff, and/or neo-leaflet 32 may comprise one or more stiffening elements within neo-leaflet cover 38, as described above.

For other applications, neo-leaflet 32 is configured such that coaptation surface 34 moves toward and away from the one or more opposing native leaflets 28 during a cardiac cycle of the subject upon implantation of coaptation-assist device 20 in a heart of the subject. In other words, neo-leaflet 32 is configured such that coaptation surface 34 is dynamic throughout the cardiac cycle. In these applications, coaptation is provided by motion of coaptation surface 34 provided by neo-leaflet 32 and the one or more opposing native leaflets 28. For example, to allow this motion of coaptation surface 34, neo-leaflet wire loop 36 and/or neo-leaflet cover 38 of neo-leaflet 32 may be flexible enough to allow it to move during the cardiac cycle. Further alternatively, the neo-leaflet cover may have a surface area that is greater than an area defined and surrounded by the neo-leaflet wire loop, so as to create a flexible parachute-like coaptation surface that inflates and relaxes during the cardiac cycle. During systole surface of coaptation 34 increases, causing the neo-leaflet to be closer to the one or more opposing native leaflets 28, so as to better prevent regurgitation. The flexible parachute-like coaptation surface is configured to inflate and relax along the blood flow and pressure variation against the ventricular surface of coaptation during the cardiac cycle, so that both the blood flow and blood pressure increase and are directed against the ventricular surface of the neo-leaflet during the systolic phase of the cardiac cycle. As a result, the neo-leaflet inflates and dynamically increases the surface of coaptation for the one or more opposing native leaflets 28. The blood flow and blood pressure action against the neo-leaflet ventricular surface decrease during the diastolic phase, causing the neo-leaflet to relax and deflate, leaving the neo-leaflet structure in a resting shape during the diastolic phase, so as not to occlude the orifice area blood passage from the atrial to the ventricular chamber. In other words, during diastole, the neo-leaflet deflates and relaxes, allowing passage of blood from the atrium to ventricle 23.

For some applications, any of the distal wire loops 88 described herein, including with reference to FIGS. 1A-C, 3A-C, 4, 5A-E, 6A-B, 7A-B, 10A-B, and 11, may further comprise a wire-loop cover attached to distal wire loop 88. For some of these applications, the wire-loop cover comprises one or more biocompatible thin sheets of material that extend across and partially or entirely occupy a space at least partially surrounded by the distal wire loop. Typically, the one or more biocompatible thin sheets of material are soft and atraumatic. For some applications, the one or more biocompatible thin sheets of material are configured to promote endothelization. The one or more biocompatible thin sheets of material may comprise a synthetic material or a biological tissue material, such as, for example, a fabric comprising of a polymer or biomaterial (e.g., polyethylene terephthalate (PET), expanded polytetrafluoroethylene (ePTFE), silicone, urethane, or pericardium). For still other applications, the wire-loop cover comprises a coating on the distal wire loop, e.g., tissue, polyethylene terephthalate (PET), expanded polytetrafluoroethylene (ePTFE), or a foam. Alternatively or additionally, the distal wire loop surface may be mechanically or chemically treated, e.g., by electropolishing or sandblasting, or provided with barbs, in order to create friction to help maintain the loop in place.

Similarly, for some applications, distal wire loop 590, described hereinbelow with reference to FIGS. 9A-B and 10A-B, may further comprise a cover attached to distal wire loop 590. This cover may have any of the characteristics of the wire-loop cover described immediately above.

Reference is again made to FIG. 2. In an application of the present invention, a method is provided for implanting coaptation-assist device 20 in a heart of a subject. For some applications, the method is performed partially using techniques described with reference to FIGS. 9A-H of above-mentioned International Application PCT/IL2020/050057, mutatis mutandis.

Coaptation-assist device 20 is percutaneously (endovascularly) delivered to a heart of the subject while coaptation-assist device 20 is removably disposed in a delivery tube of a delivery system in a compressed configuration. For some applications, coaptation-assist device 20 is loaded in the compressed configuration into the delivery tube by extending and flattening coaptation-assist device 20 into an elongate flattened configuration, and then further radially compressing (e.g., crimping) the device. For example, for applications in which coaptation-assist device 20 is used to treat tricuspid valve 19, such as shown in FIG. 2, the delivery tube may be advanced into a right atrium 17 via the inferior or superior vena cava. For applications in which coaptation-assist device 20 is used to treat a mitral valve, the delivery tube may be advanced transseptally into a left ventricle, using transseptal advancement techniques known in the art. Alternatively, coaptation-assist device 20 is delivered in a minimally-invasive procedure.

The delivery system typically comprises the delivery tube and optionally one or more additional tubes. One or more of the tubes is steerable (e.g., two are steerable, one for trajectory, and the other for positioning). Optionally, coaptation-assist device 20 is partially disposed in the delivery tube and partially disposed in another of the tubes, to allow sequential deployment of the elements of coaptation-assist device 20. For configurations in which coaptation-assist device 20 is entirely disposed within the delivery tube, typically distal anchor 58 is disposed more distally within the tube than neo-leaflet 32 (i.e., closer to the distal end of the tube), to allow distal anchor 58 to be deployed from the tube before neo-leaflet 32 is deployed. Alternatively, the arrangement is reversed, to allow neo-leaflet 32 to be deployed from the tube before distal anchor 58 is deployed.

Thereafter, distal anchor 58 is deployed from the delivery tube and positioned in ventricle 23. Typically, distal anchor 58 is deployed by proximally withdrawing the delivery tube and/or pushing the loop-shaped ventricular anchor from the delivery tube.

Thereafter, neo-leaflet 32 is deployed from the delivery tube and positioned such that neo-leaflet 32 at least partially replaces function of target native leaflet 26 by providing coaptation surface 34 for one or more opposing native leaflets 28 that oppose target native leaflet 26. Typically, distal anchor 58 is deployed by proximally withdrawing the delivery tube.

Although distal anchor 58 is shown and described as being deployed before neo-leaflet 32, in some configurations the order of deployment is reversed.

For some applications, ventricular anchor 30 is configured to be atraumatic, and positioning ventricular anchor 30 does not comprise penetrating tissue of the surrounding anatomy with ventricular anchor 30. For some applications, the deployment method does not comprise penetrating tissue with any elements of coaptation-assist device 20.

For some applications, as shown in FIG. 2, neo-leaflet 32 is positioned such that coaptation surface 34 of neo-leaflet 32 crosses from an atrial side to a ventricular side of a native valvular plane, when anchored in place, so that the native leaflet 28 coapts with neo-leaflet 32 during the cardiac cycle, with the atrial surface of native leaflet 28 coming into contact with an atrial surface 29 of neo-leaflet 32, thereby stopping blood passage from ventricle 23 to the atrium during the systolic cardiac cycle phase.

For some applications, neo-leaflet cover 38 has a surface area that is greater than an area defined by and surrounded on approximately three sides by neo-leaflet open wire loop 36, such as shown in and described with reference to FIGS. 6A-C of above-mentioned International Application PCT/IL2020/050057, mutatis mutandis. As a result, when a ventricular surface of neo-leaflet cover 38 is exposed to increased blood pressure during the cardiac cycle, neo-leaflet cover 38 tents away from neo-leaflet open wire loop 36, providing a flexible parachute-like coaptation surface 34 that expand (inflates) and relaxes during the cardiac cycle. Neo-leaflet cover 38 is shown relaxed in FIG. 6A of the '057 application, and expanded (inflated) by blood flow in FIGS. 6B and 6C of the '057 application. Optionally, neo-leaflet cover 38 comprises an elastic material.

Figure 3A:
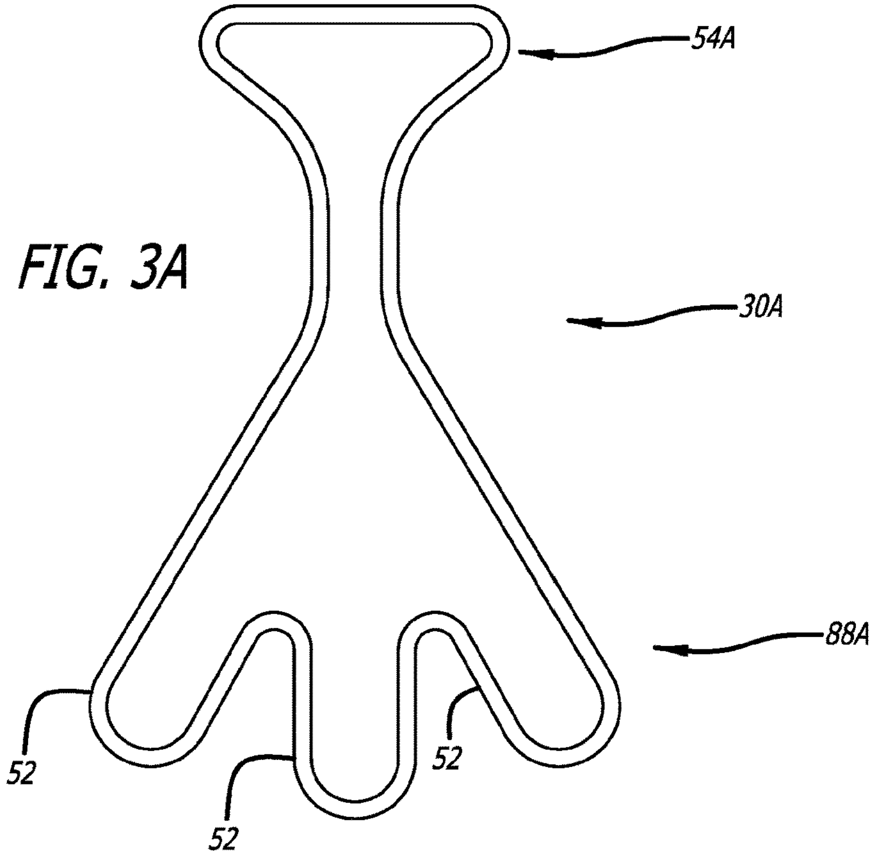
FIGS. 3A-C are schematic illustrations of distal wire loops, in accordance with respective applications of the present invention.
Figure 3B:
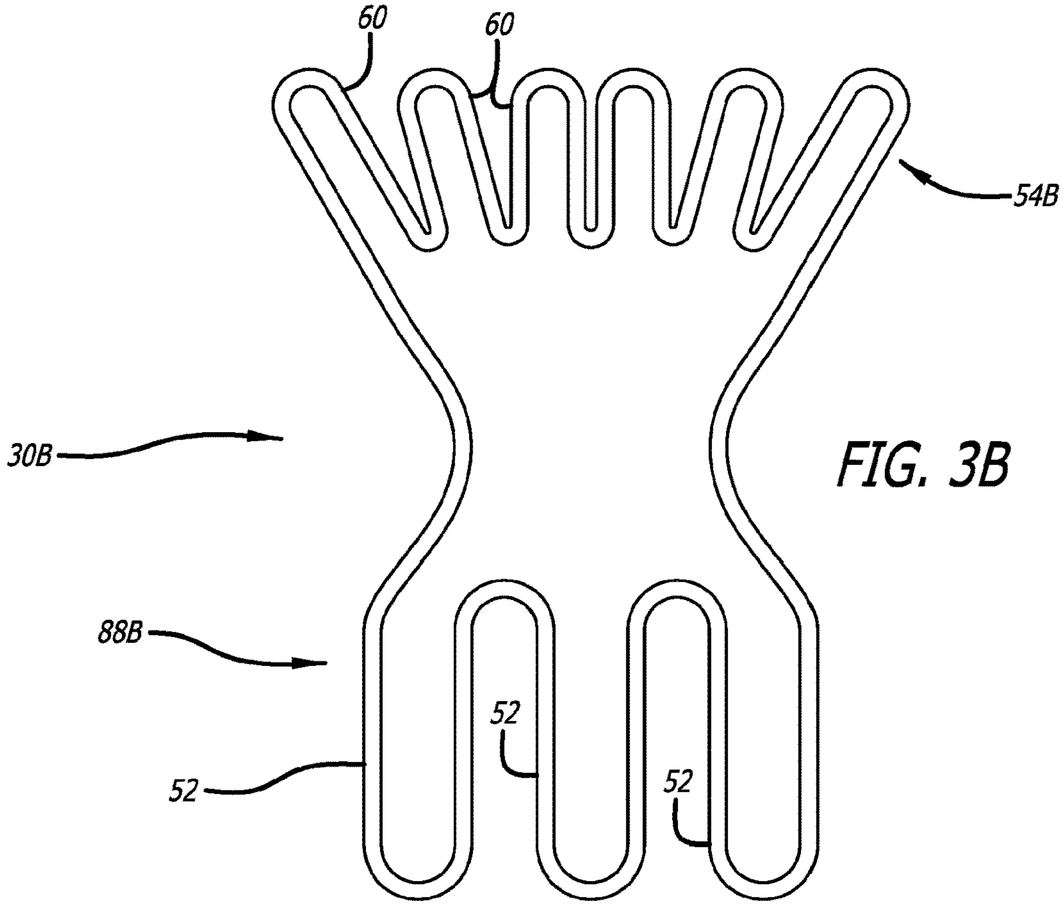
Figure 3C:
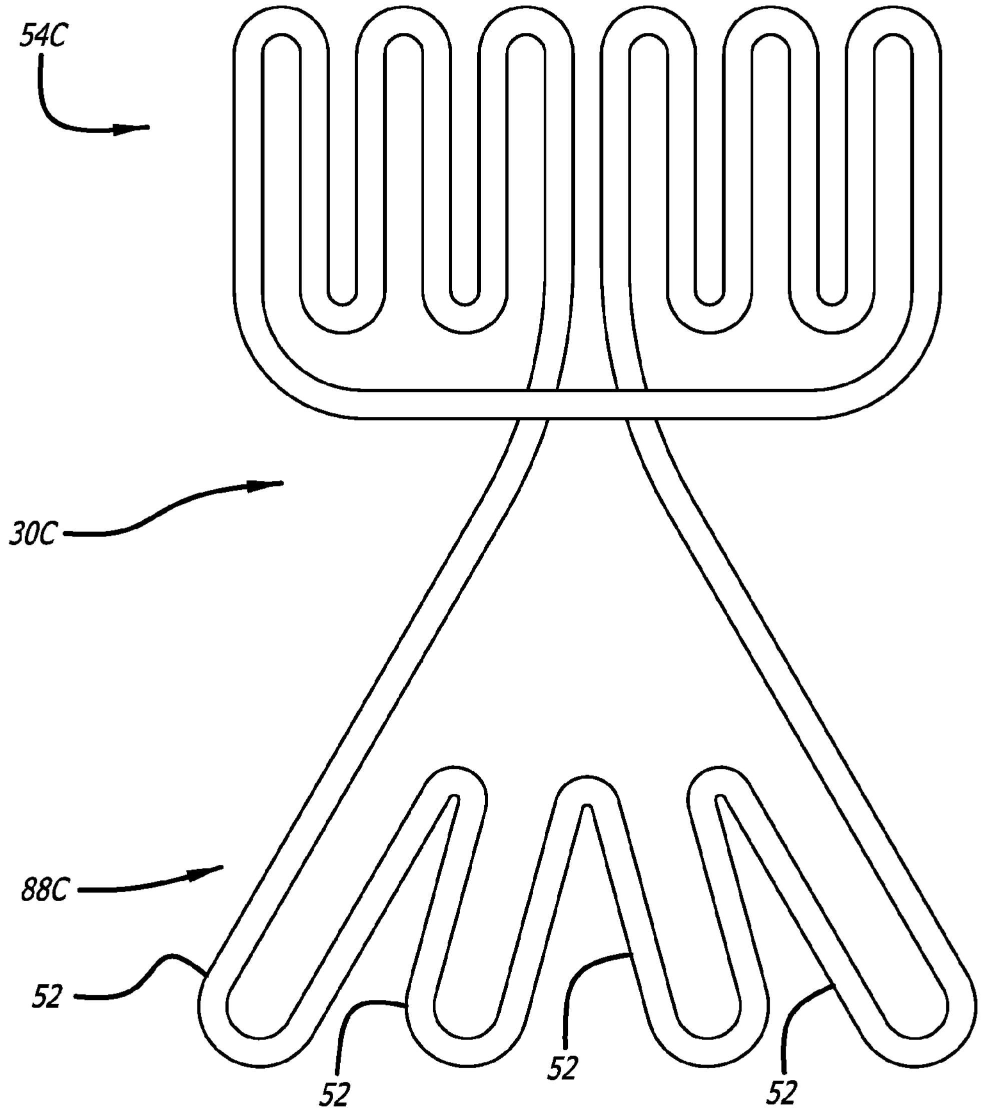

Reference is now made to FIGS. 3A-C, which are schematic illustrations of ventricular anchors 30A, 30B, and 30C, respectively, in accordance with respective applications of the present invention. Ventricular anchors 30A, 30B, and 30C comprise proximal subannular anchors 54A, 54B, and 54C, respectively, and distal wire loops 88A, 88B, and 88C, respectively. In these figures, the proximal ends of distal wire loops 88 are shown above the distal ends on the sheet (the proximal ends are the ends closer to the neo-leaflet).

Distal wire loop 88A of FIG. 3A is shaped so as to define three lobes 52 that extend in three different inferior directions. Proximal subannular anchor 54A is shaped so as to define a single subventricular loop.

Distal wire loop 88B of FIG. 3B is shaped so as to define three lobes 52 that all extend in an inferior direction parallel to one another.

Distal wire loop 88C of FIG. 3C is shaped so as to define four lobes 52 that extend in four different inferior directions, covering the entire width of the ventricular target area and stabilizing the anchoring even in case of complex ventricular trabeculation. The four lobes may provide flexibility for the lobes to find their space among the ventricular trabeculation of the ventricular space. For example, each of the lobes may be flexible enough to find a space between two trabeculae, without reducing the stability of the implant.

Figure 4:
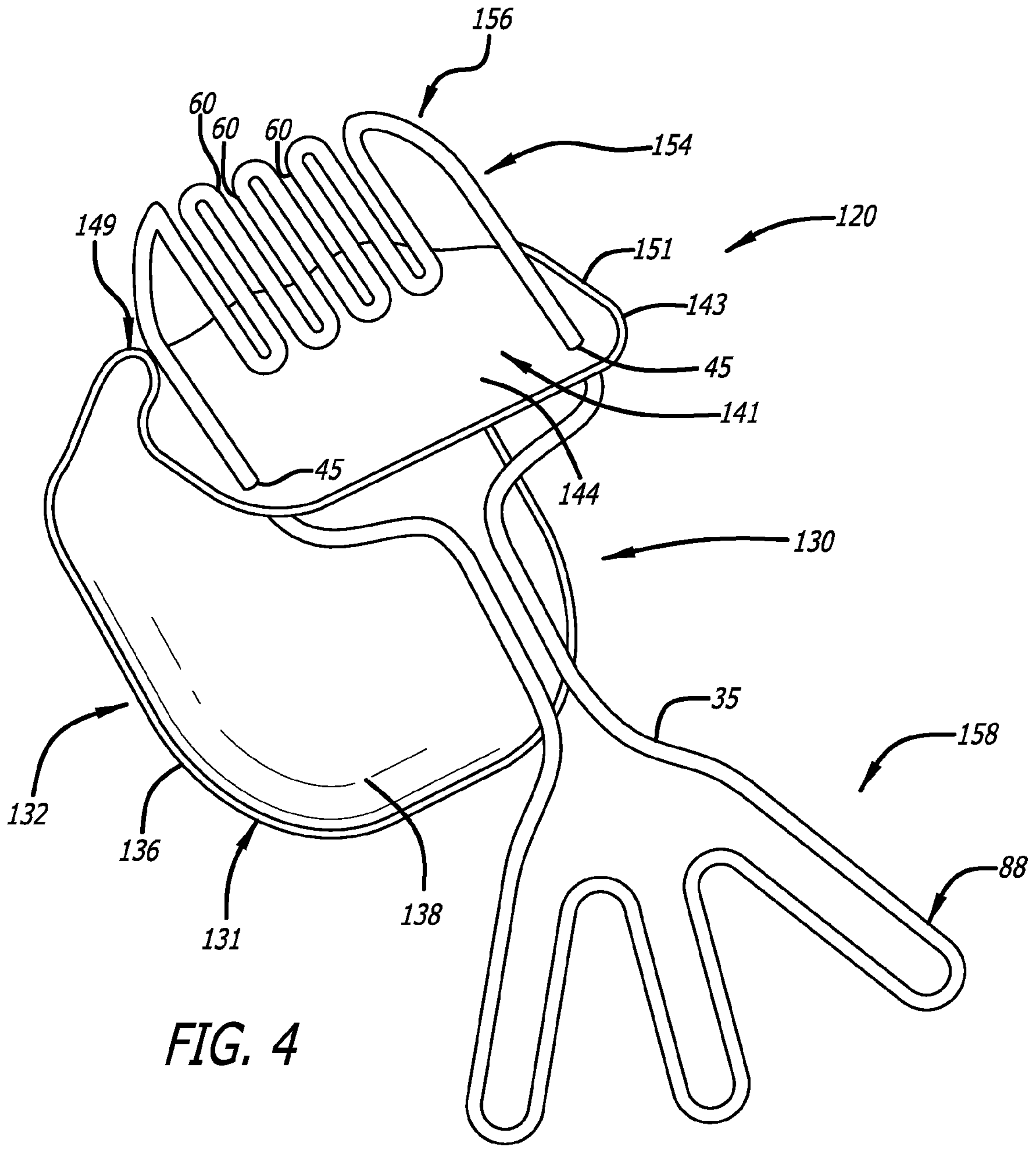
FIG. 4 is a schematic illustration of another coaptation-assist device, in accordance with an application of the present invention.
Figure 5A:
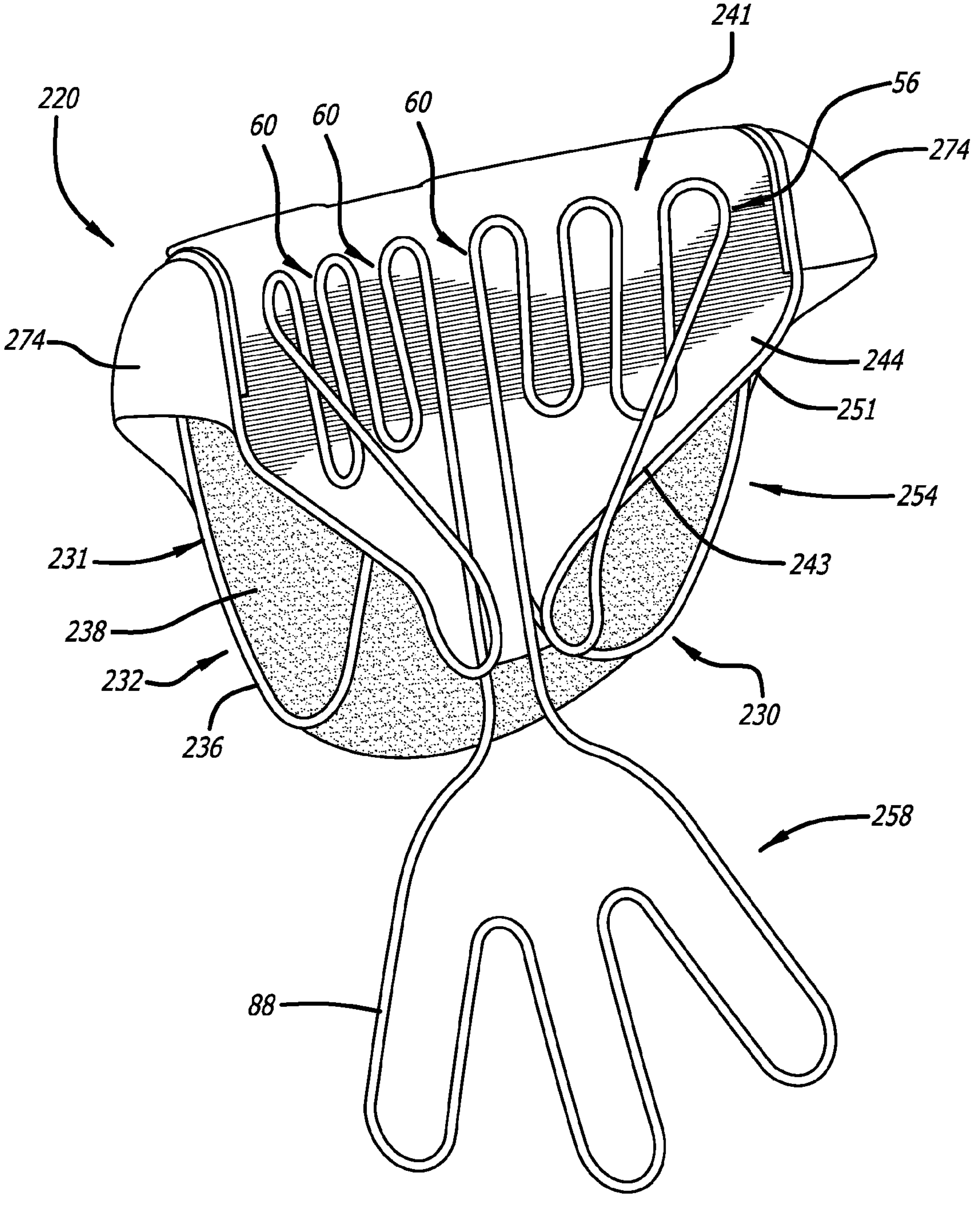
FIGS. 5A-E are schematic illustrations of yet another coaptation-assist device, in accordance with an application of the present invention.
Figure 5B:
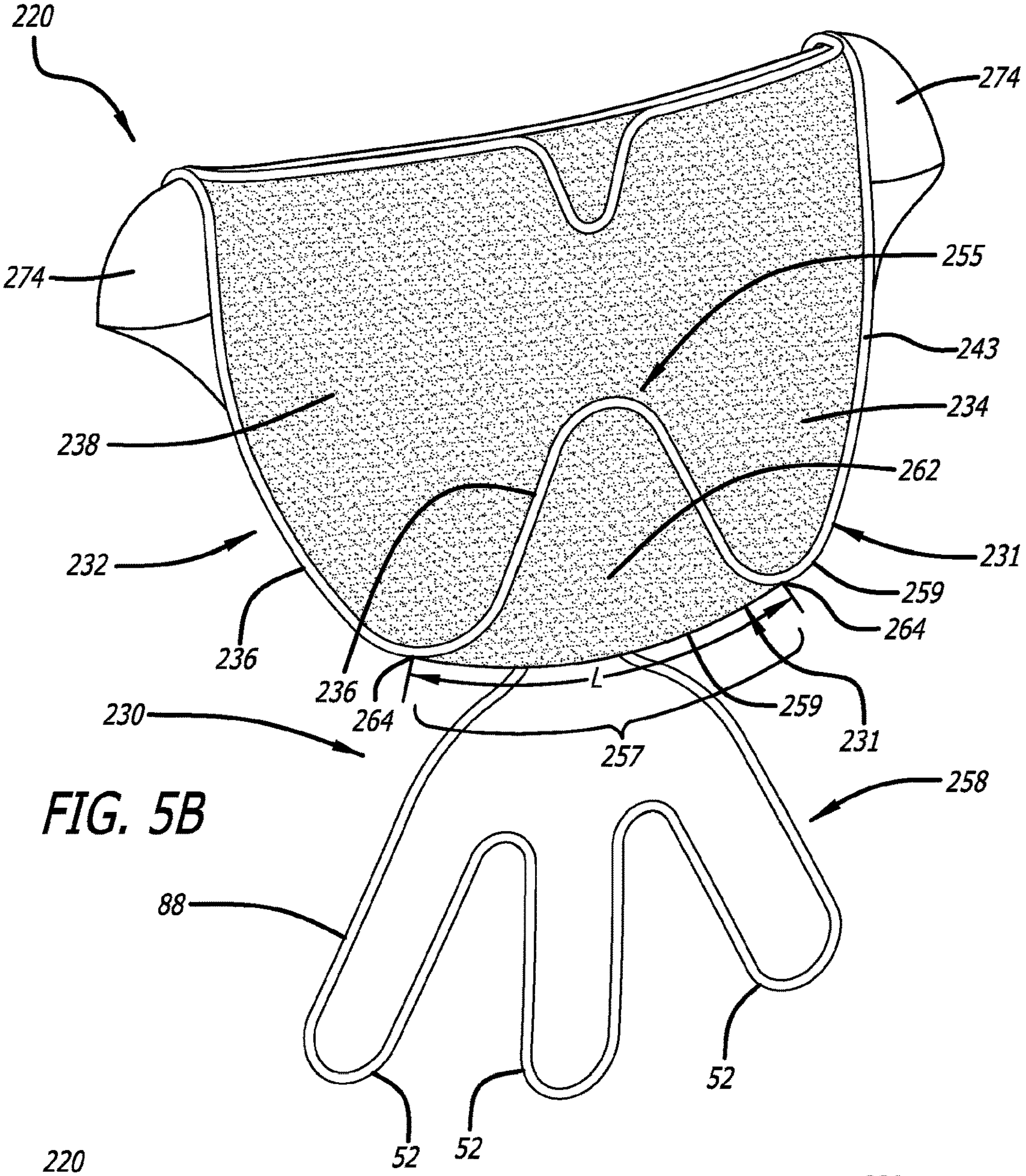
Figure 5C:
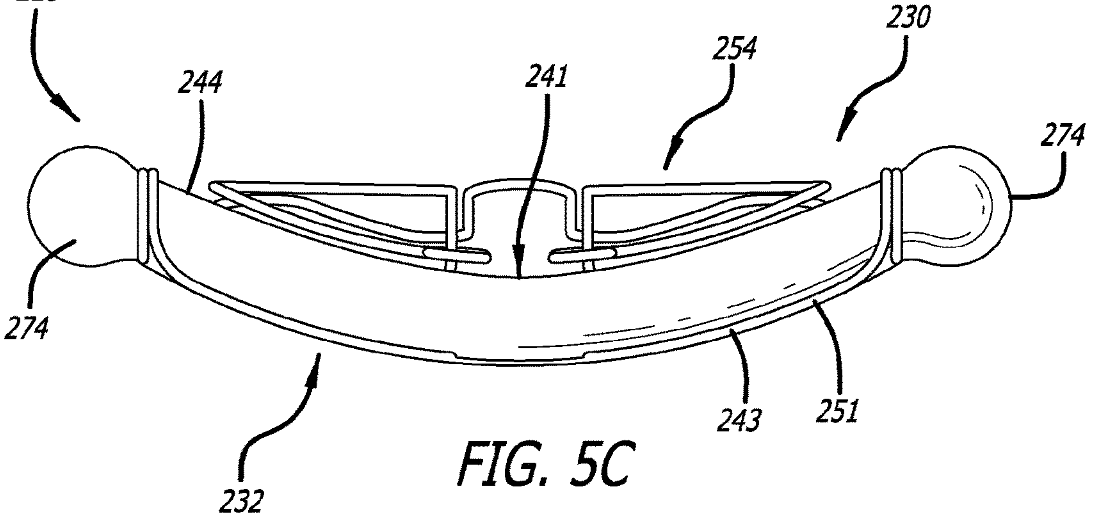
Figure 5D:
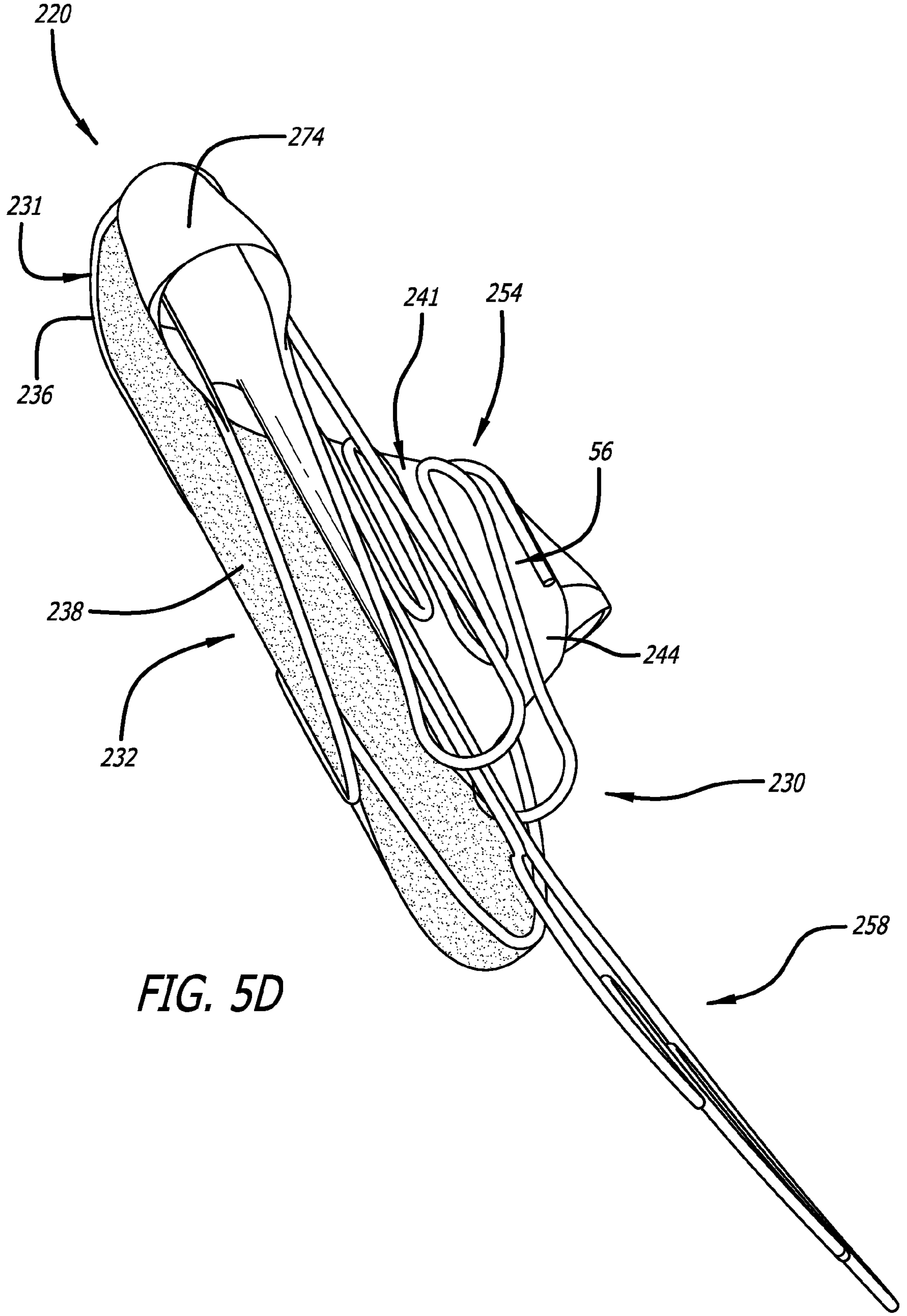
Figure 5E:
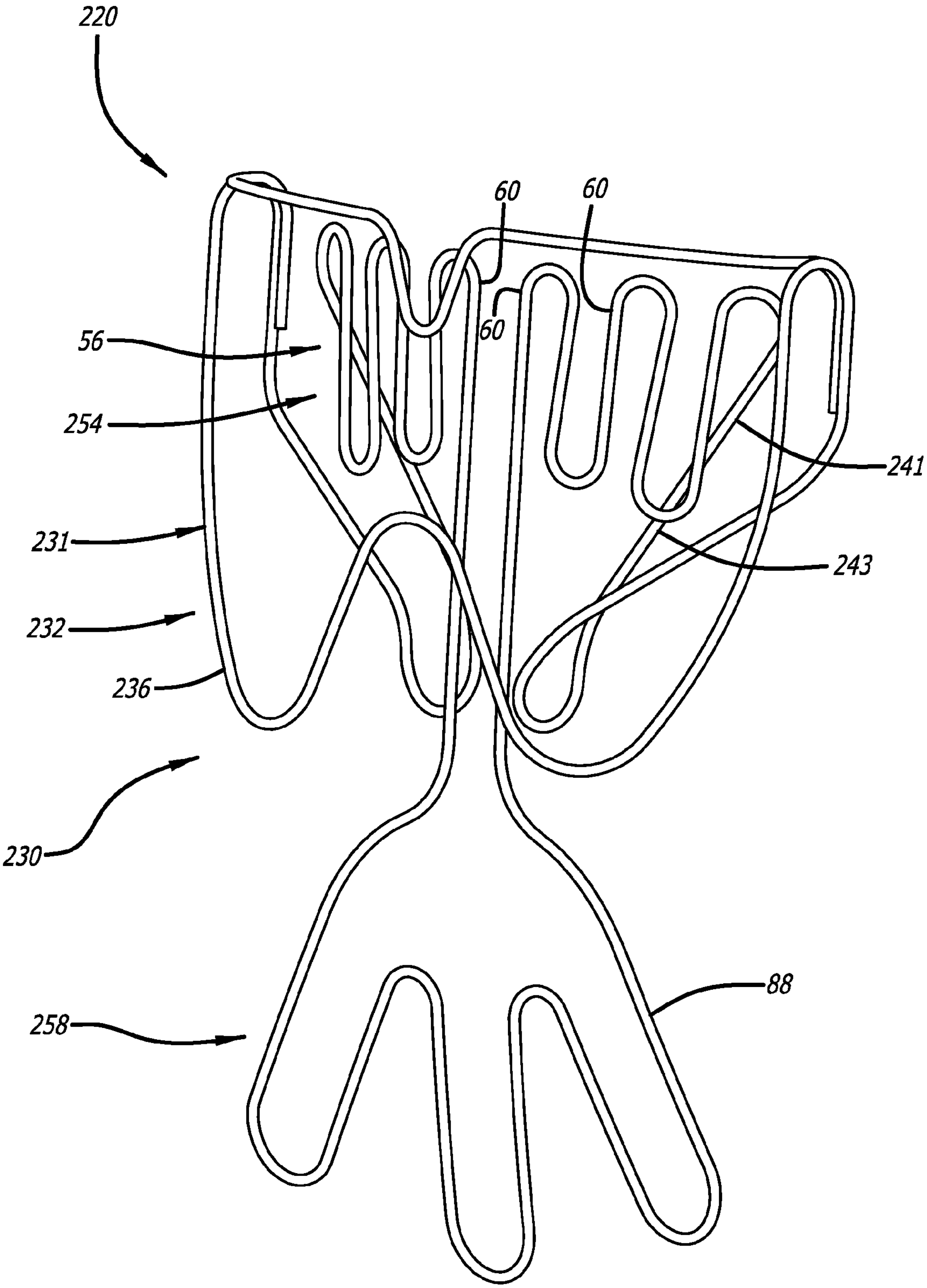

Reference is now made to FIG. 4, which is a schematic illustration of a coaptation-assist device 120, in accordance with an application of the present invention. Other than as described hereinbelow, coaptation-assist device 120 is generally similar to coaptation-assist device 20, described hereinabove with reference to FIGS. 1A-C and 2, and like reference numerals refer to like parts. Coaptation-assist device 120 may implement any of the features of coaptation-assist device 20, mutatis mutandis, including the features described hereinabove with reference to FIGS. 3A-C, mutatis mutandis.

Coaptation-assist device 120 comprises a neo-leaflet 132, which is supported by a ventricular anchor 130. Ventricular anchor 130 comprises a proximal subannular anchor 154 and a distal anchor 158. Proximal subannular anchor 154 comprises a digitate anchor 156. Ventricular anchor 130, proximal subannular anchor 154, digitate anchor 156, and distal anchor 158 may implement any of the features of ventricular anchor 30, proximal subannular anchor 54, digitate anchor 56, and/or distal anchor 58, respectively, described hereinabove with reference to FIGS. 1A-C, 2, and/or 3A-C, mutatis mutandis. For some applications, such as shown in FIG. 4, distal anchor 158 is defined at least in part by at least one of the one or more wires 35. For some these applications, the at least one of the one or more wires 35 that defines distal anchor 158 is shaped as distal wire loop 88, which provides distal anchor 158 with a loop-shaped border. Distal wire loop 88 may implement any of the configurations of distal wire loop 88 described hereinabove with reference to FIGS. 1A-C, 2, and/or 3A-C, mutatis mutandis.

For some applications, neo-leaflet 132 comprises a neo-leaflet wire loop 136, which defines a portion of a border 131 of the neo-leaflet, and a neo-leaflet cover 138, attached to neo-leaflet wire loop 136. Typically, neo-leaflet cover 138 provides the above-mentioned coaptation surface 34. Neo-leaflet cover 138 may implement any of the features of neo-leaflet cover 38, described hereinabove with reference to FIGS. 1A-C and 2, mutatis mutandis. In the illustrated configurations, neo-leaflet wire loop 136 is shaped as an open loop, which is open on a proximal side in the direction of loop-shaped ventricular anchor 130 and an atrial-surface support 141, described below. (The loop is considered open even though it is defined by a wire that also defines a portion of atrial-surface support 141, because the portion of the wire that defines the loop is open.) Alternatively, neo-leaflet wire loop is shaped as a closed loop, such as shown in FIGS. 1A-C (configuration not shown for coaptation-assist device 120). Neo-leaflet wire loop 136 may implement any of the features of neo-leaflet wire loop 36, described hereinabove with reference to FIGS. 1A-C and 2, mutatis mutandis.

As mentioned above, coaptation-assist device 120 further comprises atrial-surface support 141. Atrial-surface support 141 and digitate anchor 156 are configured to grasp and sandwich at least a portion of target native leaflet 26, in order to support neo-leaflet 132, and to orient neo-leaflet 132 with respect to native atrioventricular valve 22.

For some applications, atrial-surface support 141 comprises a frame 151 and an atrial-surface cover 144, which is coupled to frame 151. Frame 151 comprises one or more wires 143. Typically, frame 151 defines at least a portion of a border of atrial-surface cover 144. Atrial-surface cover 144 comprises one or more biocompatible thin sheets of material (optionally, the same one or more sheets of material (e.g., the same exactly one sheet of material) define both neo-leaflet cover 138, described above, and atrial-surface cover 144; alternatively, separate sheets of material define neo-leaflet cover 138 and atrial-surface cover 144. Typically, atrial-surface cover 144 pushes against atrial surface 47 of target native leaflet 26 to prevent blood flow between target native leaflet 26 and the coaptation-assist device. Atrial-surface cover 144 may implement any of the features of atrial-surface cover 44, described hereinabove with reference to FIGS. 1A-C and 2, mutatis mutandis.

For some applications, neo-leaflet 132 is coupled to ventricular anchor 130 via atrial-surface support 41, such as shown in FIG. 4.

For some of these applications, such as shown in FIG. 4, portions of the one or more wires 35 that define proximal subannular anchor 154 are coupled to atrial-surface cover 44 by passing through openings 45 defined by atrial-surface cover 44. This configuration allows pivoting and sliding of proximal subannular anchor 154 (and thus proximal subannular anchor 54 and distal anchor 158) with respect to atrial-surface support 141, and thus with respect to neo-leaflet 132.

For others of these applications, portions of the one or more wires 35 that define proximal subannular anchor 154 are coupled to frame 151 of atrial-surface support 141. The one or more wires 35 are fixed (e.g., welded) to frame 151 of atrial-surface support 141, or may not be fixed to frame 151 of atrial-surface support 141, so as to allow pivoting and sliding of proximal subannular anchor 154 with respect to atrial-surface support 141, and thus with respect to neo-leaflet 132. These configurations are now shown in the figures, but are similar to the configurations shown in FIGS. 11A-D of above-mentioned International Application PCT/IL2020/050057, mutatis mutandis.

For some applications, such as shown in FIG. 4, neo-leaflet wire loop 136 narrows at a border 149 between neo-leaflet 132 and atrial-surface support 141. This narrowing may reduce interaction between the coaptation-assist device and the surrounding anatomy. Alternatively, neo-leaflet wire loop 136 does not narrow at border 149 between neo-leaflet 132 and atrial-surface support 141 (configuration not shown, but similar to the configurations shown in FIGS. 10D-F and 11A-D of above-mentioned International Application PCT/IL2020/050057, mutatis mutandis.

Reference is now made to FIGS. 5A-E, which are schematic illustrations of a coaptation-assist device 220, in accordance with an application of the present invention. Other than as described hereinbelow, coaptation-assist device 220 is generally similar to coaptation-assist device 20, described hereinabove with reference to FIGS. 1A-C and 2, mutatis mutandis. Coaptation-assist device 220, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 220 comprises a ventricular anchor 230, which comprises a proximal subannular anchor 254 and, typically, a distal anchor 258. Ventricular anchor 230, proximal subannular anchor 254, and distal anchor 258 may implement any of the features of the ventricular anchors, proximal subannular anchors, and distal anchors described herein, mutatis mutandis.

Coaptation-assist device 220 further comprises a neo-leaflet 232, which may implement any of the features of the neo-leaflets described herein, mutatis mutandis. For some applications, neo-leaflet 232 comprises a neo-leaflet wire loop 236, which defines at least a portion of a border 231 of the neo-leaflet, and a neo-leaflet cover 238 attached to neo-leaflet wire loop 236. (For clarity of illustration, in FIG. 5E coaptation-assist device 220 is shown without neo-leaflet cover 238, as well as without atrial-surface cover 244, described hereinbelow.) Neo-leaflet wire loop 236 may implement any of the features of the neo-leaflet wire loops described herein, mutatis mutandis, and neo-leaflet cover 238 may implement any of the features of the neo-leaflet covers described herein, respectively mutatis mutandis.

For some applications, neo-leaflet 232 is curved in a shield-shape to accommodate better the annular area at target native leaflet 26 level. This shield shape may also provide a coaptation surface 234 that is easy to reach for one or more opposing native leaflets 28.

Coaptation-assist device 220 further comprises an atrial-surface support 241. Atrial-surface support 241 and digitate anchor 256 are configured to grasp and sandwich at least a portion of target native leaflet 26, in order to support neo-leaflet 232, and to orient neo-leaflet 232 with respect to native atrioventricular valve 22.

For some applications, atrial-surface support 241 comprises a frame 251 and an atrial-surface cover 244, which is coupled to frame 251. Frame 251 comprises one or more wires 243. Typically, frame 251 defines at least a portion of a border of atrial-surface cover 244. Atrial-surface cover 244 comprises one or more biocompatible thin sheets of material (optionally, the same one or more sheets of material (e.g., the same exactly one sheet of material) define both neo-leaflet cover 238, described above, and atrial-surface cover 244; alternatively, separate sheets of material define neo-leaflet cover 238 and atrial-surface cover 244. Typically, atrial-surface cover 244 pushes against atrial surface 47 of target native leaflet 26 to prevent blood flow between target native leaflet 26 and the coaptation-assist device. Atrial-surface cover 244 may implement any of the features of the atrial-surface covers described hereinabove, mutatis mutandis. (The shading of atrial-surface cover 244 in FIGS. 5A-D is for clarity of illustration, and does not imply that atrial-surface cover 244 comprises a separate piece of material from neo-leaflet cover 238 or a different type of material from that of neo-leaflet cover 238, although it could.)

For some applications, coaptation-assist device 220 (e.g., neo-leaflet cover 238) comprises one or more (e.g., two) commissural pouches or parachutes 274, which are configured to inflate by blood flow and relax along the blood flow and pressure variation of the cardiac cycle, so as to push coaptation-assist device 220 against the ventricular surface of target native leaflet 26, the annulus of native valve 22, and/or the commissural space of native valve 22, thereby stabilizing coaptation-assist device 220 with respect to native valve 22 and preventing possible commissural regurgitation.

Reference is still made to FIGS. 5A-E. For some applications, as labeled in FIG. 5B, a portion 255 of neo-leaflet wire loop 236 is recessed away from border 231 of neo-leaflet 232 along a central portion 257 of an inferior edge 259 of neo-leaflet cover 238, such that neo-leaflet cover 238 defines a flap 262 bordered by recessed portion 255 of neo-leaflet wire loop 236 and central portion 257 of inferior edge 259 of neo-leaflet cover 238 when neo-leaflet 232 is not constrained. Flap 262 may serve as a miniature safety valve in case neo-leaflet 232 flips up into the atrium, rather than remaining in its intended location for coapting with the opposing native leaflet; in this position, flap 262 is typically slack to allow motion of the flap, to open and close during the cardiac cycle. Alternatively, for some applications coaptation-assist device 220 is configured such that neo-leaflet 232 is intended to be positioned at the level of the annulus above the opposing native leaflet(s); for these applications, flap 262 is configured to open and close with the cardiac cycle.

For some applications, recessed portion 255 of neo-leaflet wire loop 236 is curved when neo-leaflet 232 is not constrained, such as shown.

For some applications, central portion 257 of inferior edge 259 of neo-leaflet cover 238 extends at least as inferiorly as a most-inferior portion 264 of neo-leaflet wire loop 236 when neo-leaflet 232 is not constrained. For some of these applications, when neo-leaflet 232 is not constrained, central portion 257 of inferior edge 259 of neo-leaflet cover 238 is curved and convex, and extends more inferiorly than most-inferior portion 264 of neo-leaflet wire loop 236.

For example, when neo-leaflet 232 is not constrained, flap 262 may have an area of at least 10 mm2, no more than 40 mm2, and/or between 10 and 40 mm2 Alternatively or additionally, for example, when neo-leaflet 232 is not constrained, an area of flap 262 may equal at least 15% of an area of neo-leaflet cover 238, no more than 75% of the area, and/or between 15% and 75% of the area.

For some applications, central portion 257 of inferior edge 259 of neo-leaflet cover 238 has a length L, measured along inferior edge 259 (i.e., not necessarily in a straight line), of at least 5 mm, no more than 40 mm, and/or between 5 and 40 mm when neo-leaflet 232 is not constrained.

For some applications, neo-leaflet cover 238 does not define flap 262, such as described hereinbelow with reference to FIG. 6A regarding neo-leaflet 332 of coaptation-assist device 320.

For some applications in which neo-leaflet cover 238 defines flap 262, ventricular anchor 230 does not comprise proximal subannular anchor 254 and/or does not comprise distal anchor 258.

For some applications in which neo-leaflet cover 238 defines flap 262, ventricular anchor 230 comprises proximal subannular anchor 254, proximal subannular anchor 254 does not comprise digitate anchor 56.

Reference is still made to FIGS. 5A-E. For some applications, as labeled in FIG. 5B, a superior central portion of neo-leaflet wire loop 236 is recessed slightly away from border 231 of neo-leaflet 232. This recessing may allow for more effective crimping of the device into a delivery tube.

Figure 6A:
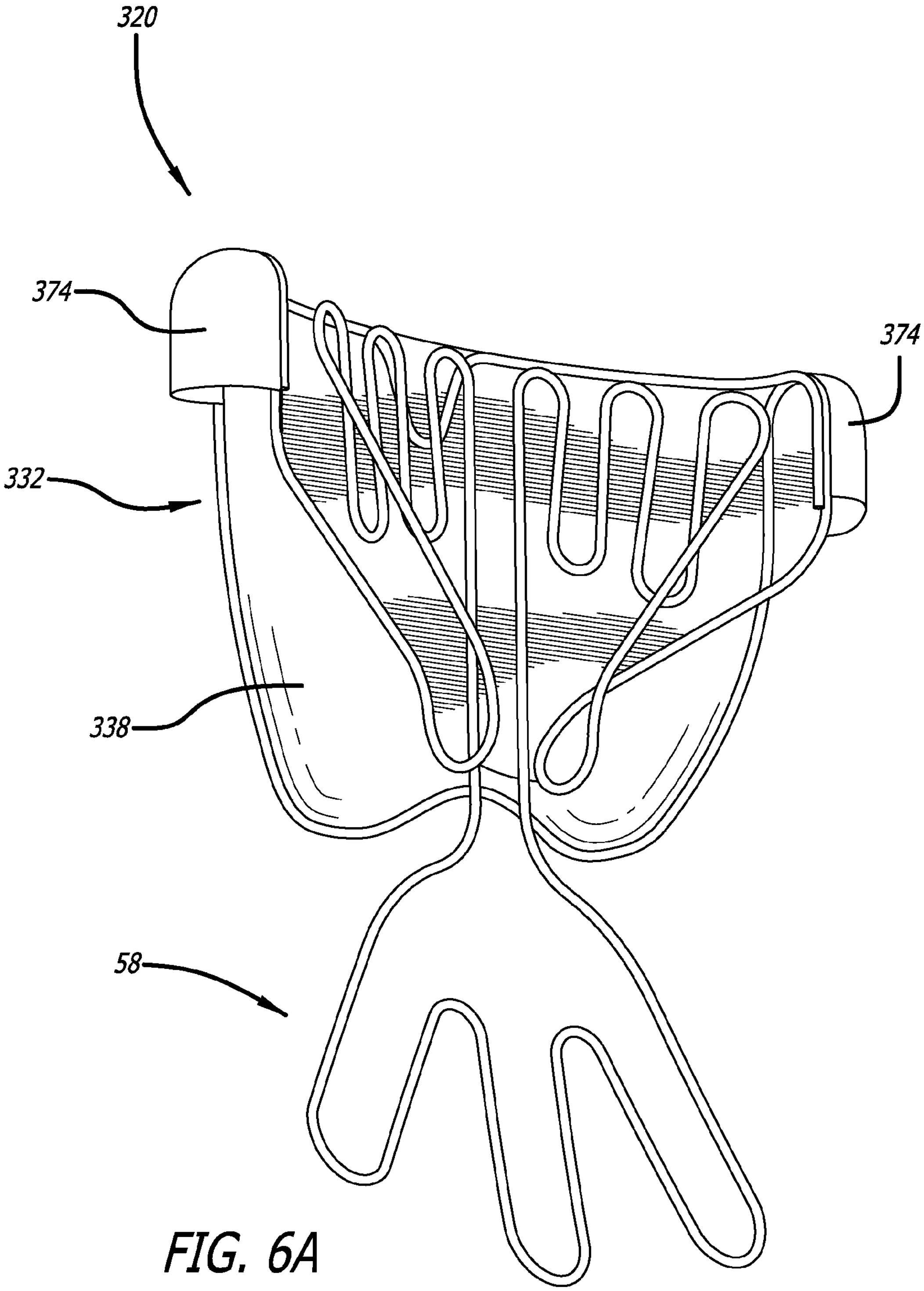
FIGS. 6A-B are schematic illustrations of additional coaptation-assist devices, in accordance with respective applications of the present invention.

Reference is now made to FIG. 6A, which is a schematic illustration of a coaptation-assist device 320, in accordance with an application of the present invention. Other than as described hereinbelow, coaptation-assist device 320 is generally similar to coaptation-assist device 220, described hereinabove with reference to FIGS. 4A-E and hereinbelow with reference to FIGS. 8A-D, mutatis mutandis, and like reference numerals refer to like parts. Coaptation-assist device 320, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

For some applications, coaptation-assist device 320 (e.g., a neo-leaflet cover 338 of a neo-leaflet 332 thereof) comprises one or more (e.g., two) commissural pouches or parachutes 374, which are configured to inflate and relax along the blood flow and pressure variation, in a similar manner to pouches or parachutes 274, described hereinabove with reference to FIGS. 5A-D. Pouches 374 in FIG. 6A originate at the same level on a neo-leaflet wire loop 336 of neo-leaflet 332, so as to have an even free edge of each pouch 374. Pouches 274 in FIGS. 5A-D originate lower (closer to the neo-leaflet tip) on neo-leaflet wire loop 236, so as to create an uneven free edge of each pouch 274. This difference in attachment points results in a higher surface of pouch 374 in FIG. 6A than in FIGS. 5A-D, such that the pouch is able to inflate more and cover a higher tridimensional surface when inflated. A higher surface can lead to better commissural area filling, with a consequent reduction in blood regurgitation in that area.

For some applications, as shown, neo-leaflet 332 of coaptation-assist device 320 does not comprise flap 262, described hereinabove with reference to FIGS. 5A-D. In these applications, a free edge of neo-leaflet 332 may be shaped so as to define a curved indentation. For other applications, coaptation-assist device 320 comprises flap 262 (configuration not shown).

Figure 6B:
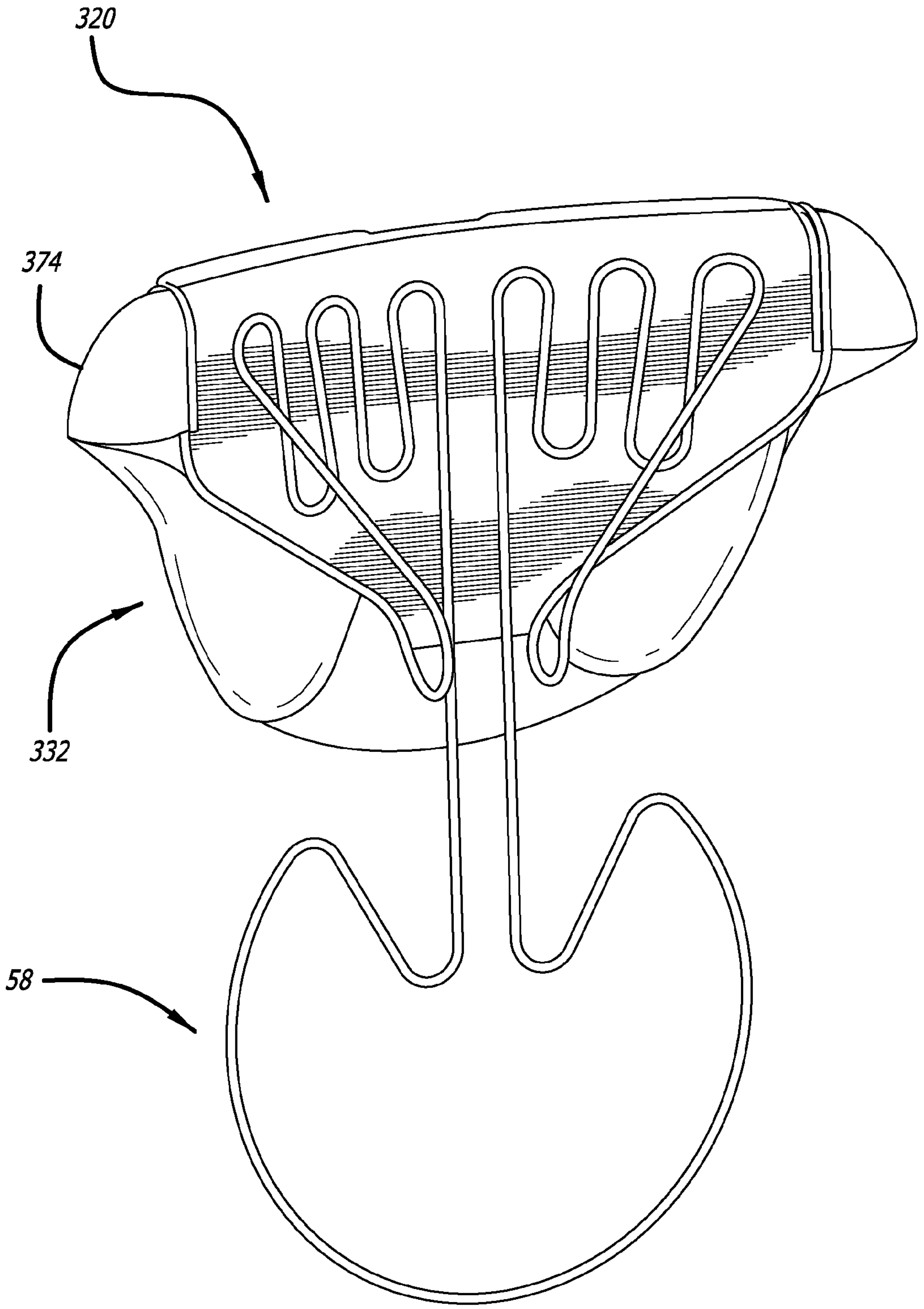

Reference is now made to FIG. 6B, which is a schematic illustration of a coaptation-assist device 321, in accordance with an application of the present invention. Other than as described hereinbelow, coaptation-assist device 321 is generally similar to coaptation-assist device 320, described hereinabove with reference to FIG. 6A and, mutatis mutandis, and like reference numerals refer to like parts. Coaptation-assist device 321, including its neo-leaflet and loop-shaped ventricular anchor, may implement (a) any of the features of coaptation-assist device 20, mutatis mutandis, including the features described hereinabove with reference to FIGS. 6A, mutatis mutandis, and/or (b) any of the features of the other coaptation-assist devices described herein, mutatis mutandis.

For some applications, coaptation-assist device 321 comprises one spring shaped ventricular anchor 380, which is configured to adapt its shape based on the constraining forces of the ventricle on its loop-shaped boundary, to elongate in larger ventricle and to compress in smaller chambers. This ventricular anchor features a spring-like component in the portion connecting the end-apical component of the loop, and the sub-annular components. The ability to compress and release the tension of the system with the spring component allows the ventricular anchoring to adjust to the specific dimensions of the subject's ventricular chamber where it is implanted, with safety, stabilization and atraumatic benefits.

Figure 7A:
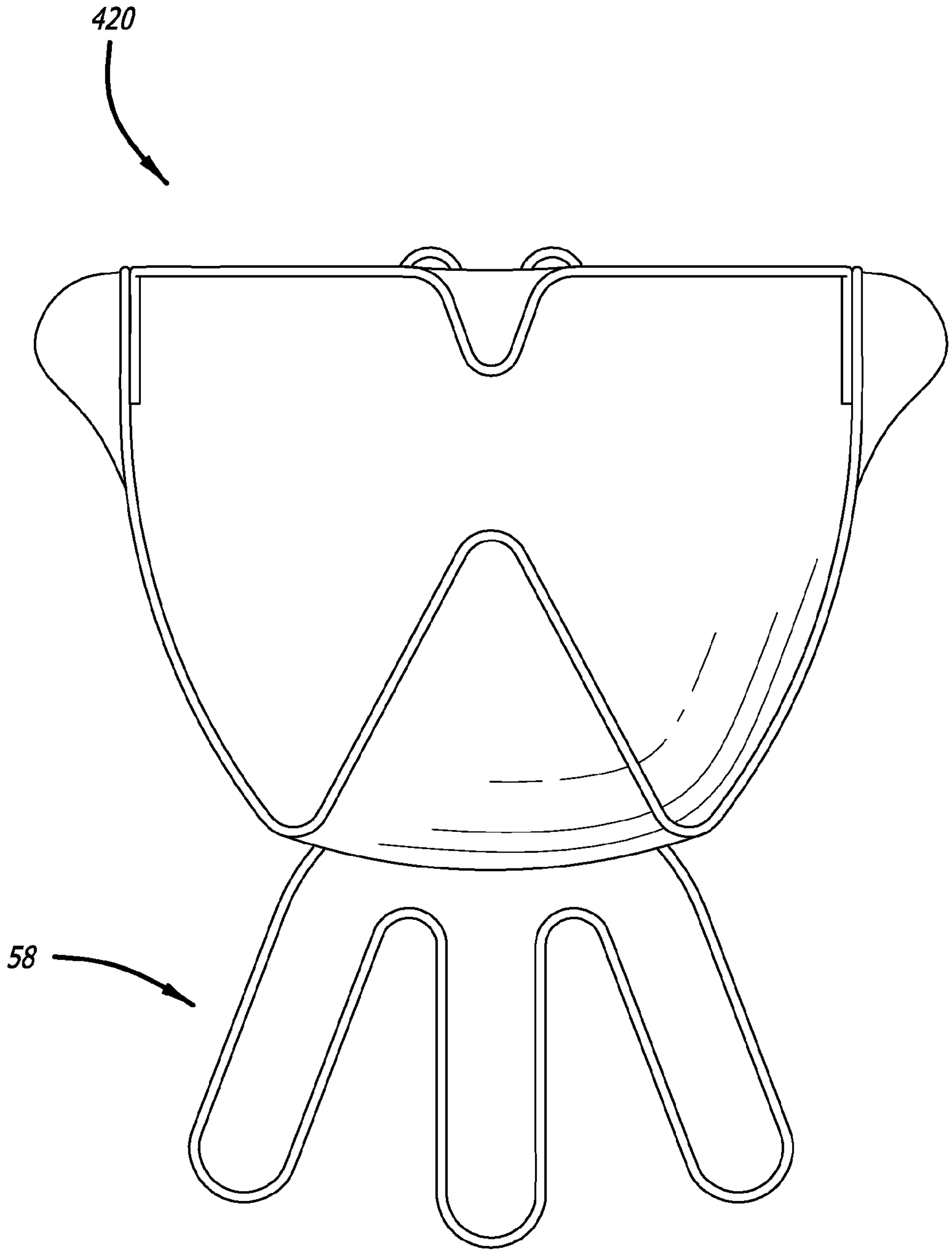
FIGS. 7A-B are schematic illustrations of yet another coaptation-assist device, in accordance with an application of the present invention.
Figure 7B:
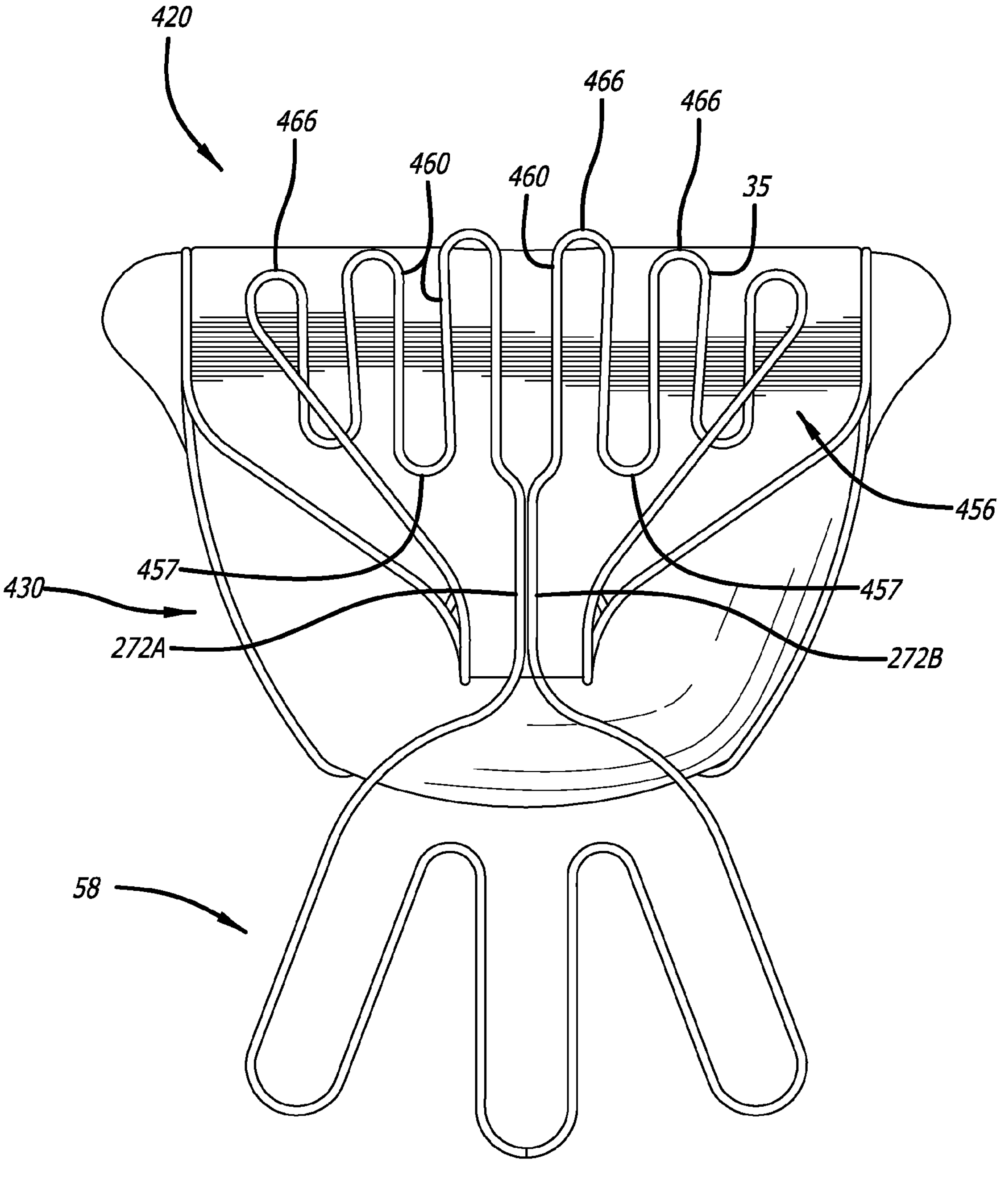

Reference is now made to FIGS. 7A-B, which are schematic illustrations of a coaptation-assist device 420, in accordance with an application of the present invention. Other than as described hereinbelow, coaptation-assist device 420 is generally similar to coaptation-assist device 220, described hereinabove with reference to FIGS. 4A-E and hereinbelow with reference to FIGS. 8A-D, mutatis mutandis, and like reference numerals refer to like parts. Coaptation-assist device 420, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

A ventricular anchor 430 of coaptation-assist device 420 comprises a proximal subannular anchor 454 and, typically, distal anchor 58. Proximal subannular anchor 454 comprises a digitate anchor 456 that is defined at least in part by at least one of the one or more wires 35. Digitate anchor 456 is shaped so as to define a plurality of fingers 460 having a plurality of curved superior peaks 466 and, for applications in which digitate anchor 456 is serpentine, a plurality of inferior troughs 467, which are typically curved. Digitate anchor 456 may optionally implement any of the features of the digitate anchors described herein, mutatis mutandis.

In some of the other digitate anchors described herein, such as digitate anchor 256, described hereinabove with reference to FIGS. 5A-E, all of curved superior peaks 66 may terminate at a same superior height. By contrast, two or more curved superior peaks 466 of digitate anchor 456 terminate at respective different superior heights. For example, one or more more-central curved superior peaks 466 may terminate at more superior heights than one or more more-lateral curved superior peaks 466, such as shown in FIGS. 7A-B. Alternatively, the opposite relative arrangement is provided (configuration not shown).

For some applications, two longitudinal superior portions 272A and 272B of a distal wire loop 488 of coaptation-assist device 420 are fixed to each other. This configuration may optionally be implemented in any of the other distal wire loops described herein.

Figure 8A:
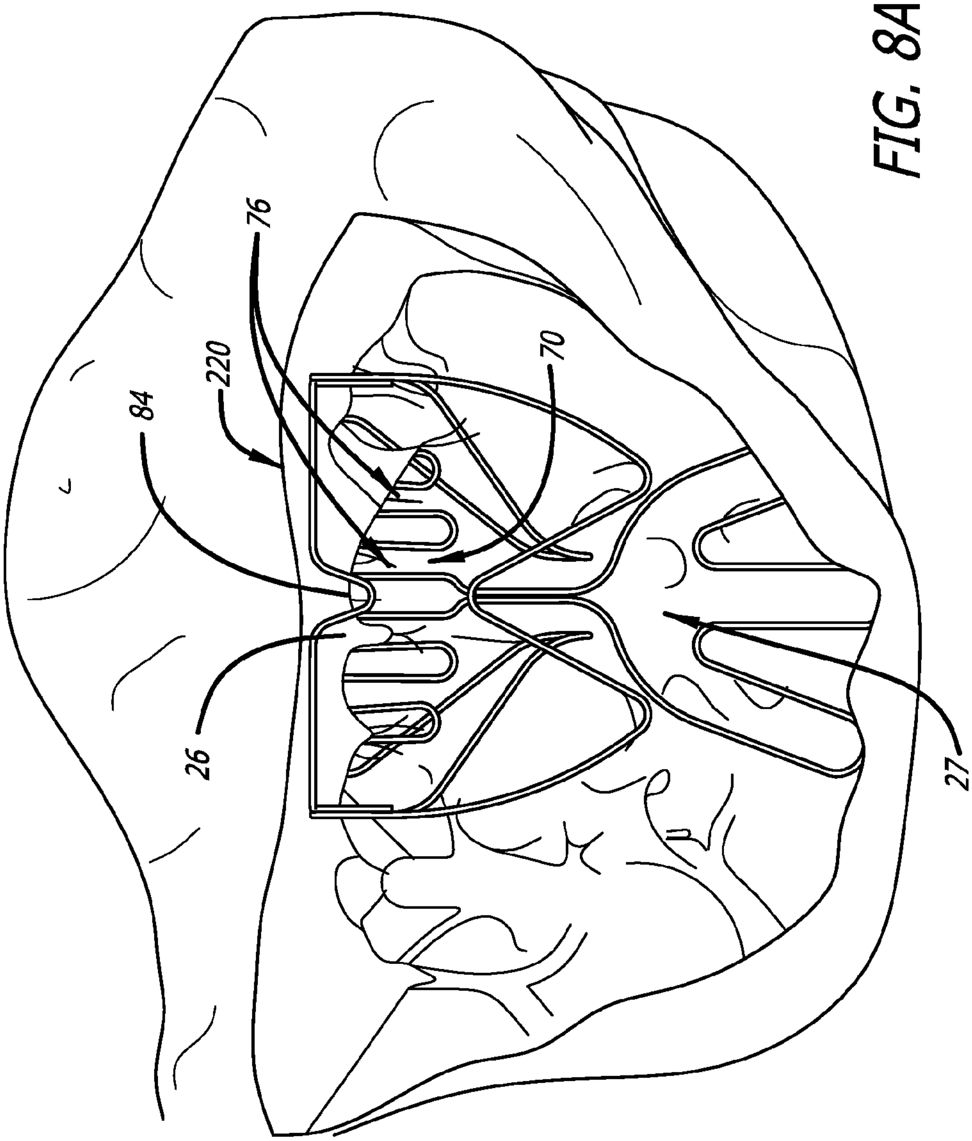
Figure 8B:
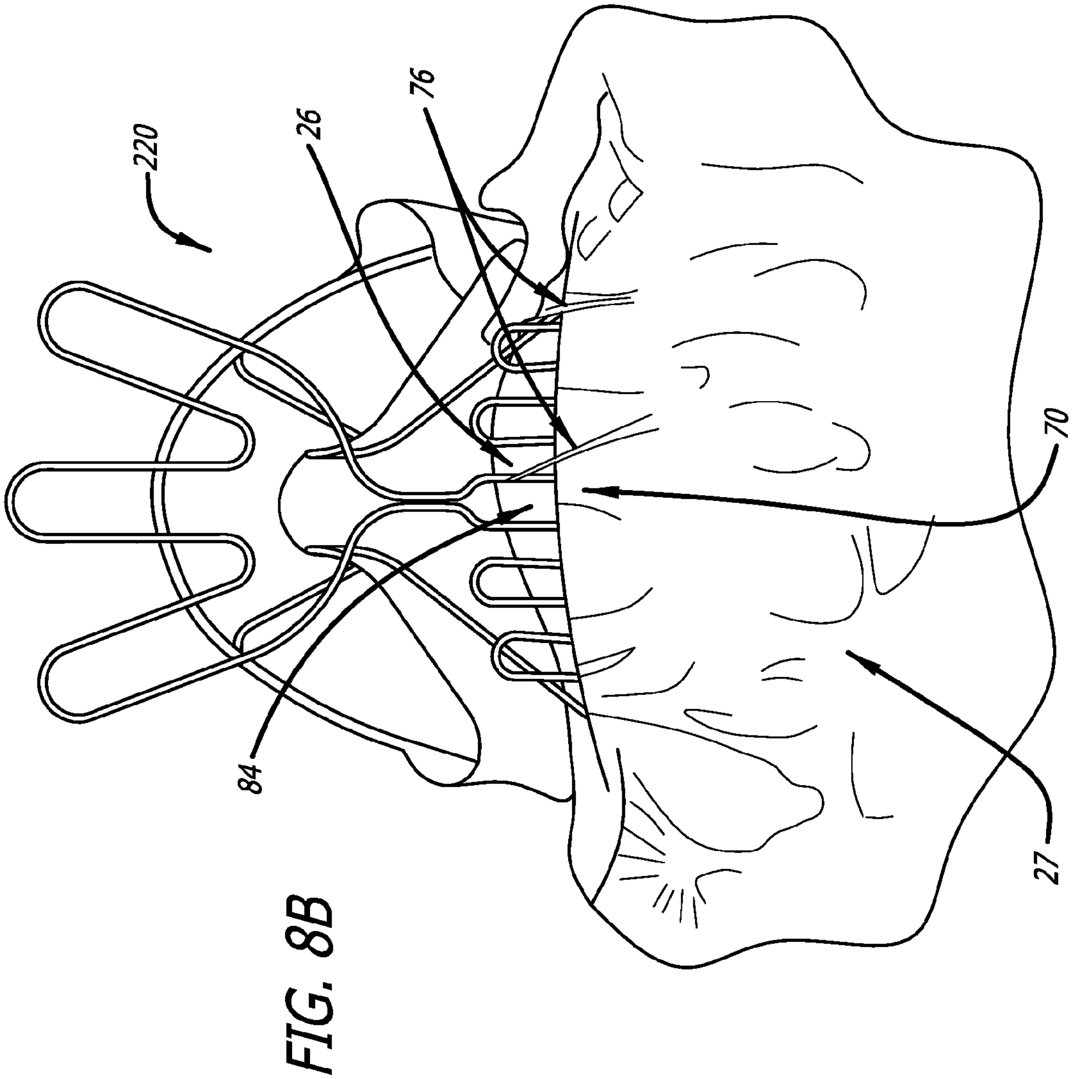

Reference is now made to FIGS. 8A-D, which are schematic illustrations of implantations of coaptation-assist device 220 in a heart, in accordance with an application of the present invention. For clarity of illustration, in FIG. 8A coaptation-assist device 220 is shown without neo-leaflet cover 238 and atrial-surface cover 244. The coaptation-assist device is shown in its deployed and implanted configuration in FIG. 8A-C, with the ventricular anchor engaging the ventricular apical area, stabilizing the implant and connecting to the subannular device's components, which are placed among the native valvular chordae tendineae, arriving through them to the base of the native leaflet. The passage through the native chordae tendineae as shown in FIG. 8D provides further stabilization of the device, as well a proper orientation of the neo-leaflet with regards to the target native leaflet. The device then allows crossing the native leaflet along its free edge, positioning and stabilizing the neo-leaflet portion for proper coaptation enhancement. The shape and dimension of the subannular anchoring elements allow the passage of the subannular structure behind the septal leaflet, avoiding the complexity of the native chordae tendineae mesh below the native leaflet.

Figure 9A:
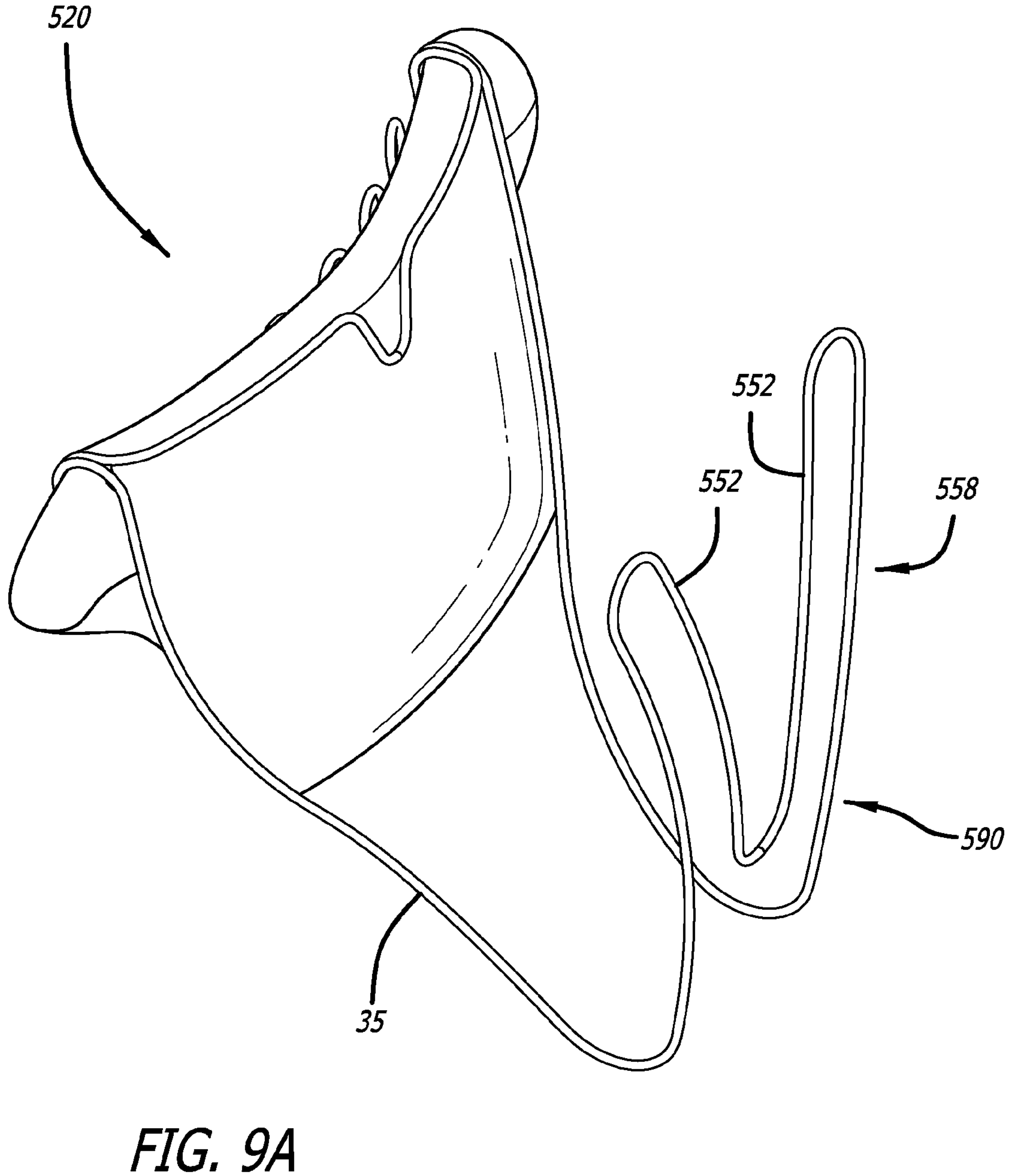
FIGS. 9A-B are schematic illustrations of another coaptation-assist device, in accordance with an application of the present invention.
Figure 9B:
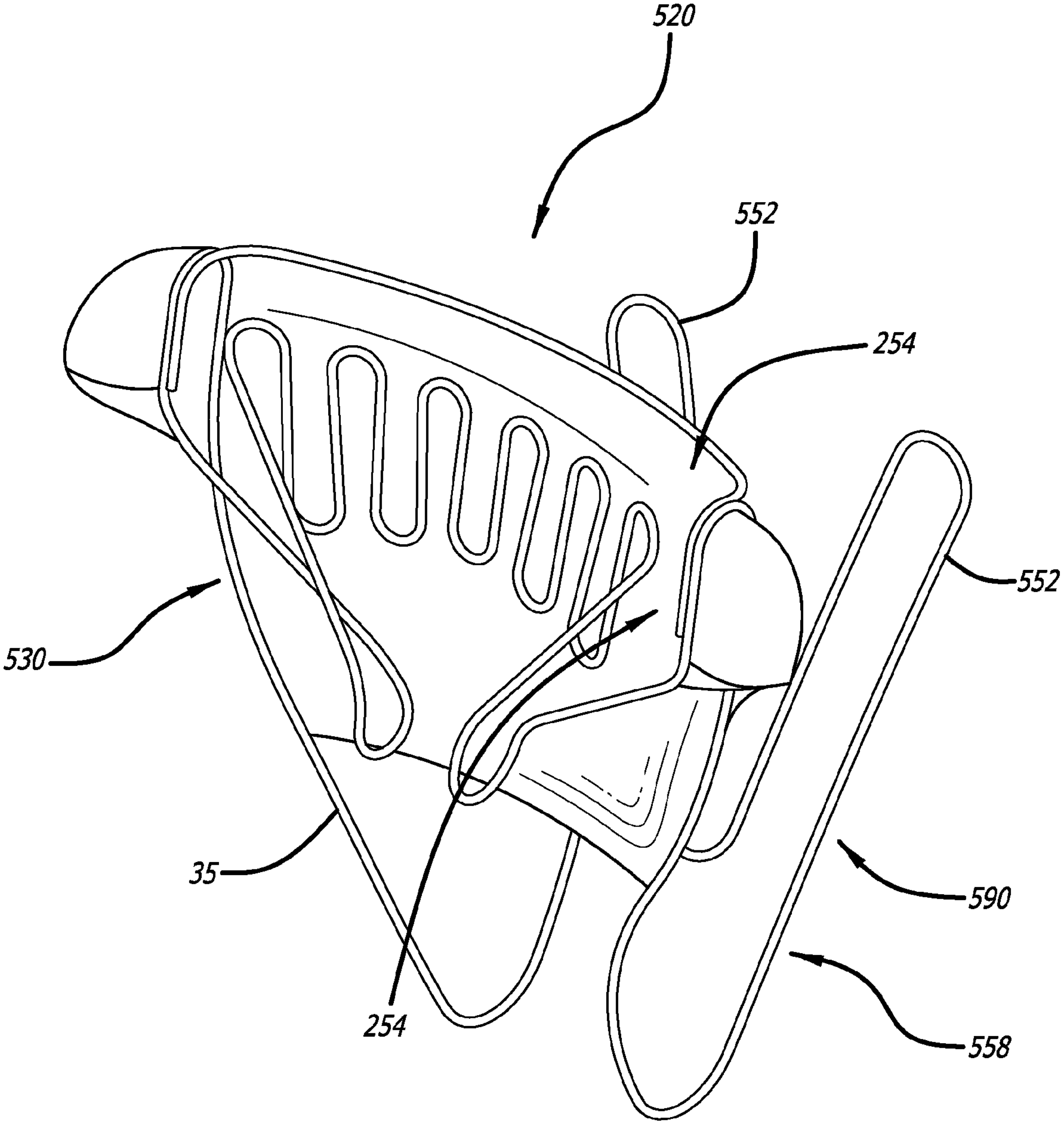

Reference is now made to FIGS. 9A-B, which are schematic illustrations of a coaptation-assist device 520, in accordance with an application of the present invention. Other than as described hereinbelow, coaptation-assist device 520 is generally similar to coaptation-assist device 220, described hereinabove with reference to FIGS. 5A-E, mutatis mutandis, and like reference numerals refer to like parts. Coaptation-assist device 520, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 520 comprises a ventricular anchor 530, which comprises proximal subannular anchor 254 and a distal anchor 558. Ventricular anchor 230 and proximal subannular anchor 254 may implement any of the features of the ventricular anchors and proximal subannular anchors described herein, mutatis mutandis.

Distal anchor 558 is defined at least in part by at least one of the one or more wires 35. The at least one of the one or more wires 35 that defines distal anchor 558 is shaped as a distal wire loop 590, which provides distal anchor 558 with a loop-shaped border. Distal wire loop 590 is configured to be positioned partially in at least one opposing-leaflet subannular space defined by at least one of the one or more opposing native leaflets, when distal anchor 558 is positioned partially against ventricular wall 27 outside target subannular space 68.

In this configuration, distal wire loop 590 may be positioned against ventricular wall 27 only within the at least one opposing-leaflet subannular space, in which case distal anchor 558 applies a generally radially-outward force on proximal subannular anchor 254, which helps push proximal subannular anchor 254 against ventricular wall 27 within target subannular space 68, in order to help hold proximal subannular anchor 554 anchored in place and/or to help prevent tilting of proximal subannular anchor 554 and thus neo-leaflet 232.

Alternatively, in this configuration, distal wire loop 590 may be positioned against ventricular wall 27 both within the at least one opposing-leaflet subannular space and at one or more locations outside the at least one opposing-leaflet subannular space, in which case distal anchor 558 typically applies a generally superiorly-directed force on proximal subannular anchor 254, which helps hold proximal subannular anchor 254 anchored in place and/or to helps prevent tilting of proximal subannular anchor 254 and thus neo-leaflet 232.

For some applications, distal wire loop 590 extends directly from neo-leaflet 232, such as shown.

For some applications, distal wire loop 590 is shaped so as to define at least two lobes 552, which are configured to be positioned partially in at two respective opposing-leaflet subannular spaces, respectively defined by two of the one or more opposing native leaflets, when distal anchor 558 is positioned partially against ventricular wall 27 outside target subannular space 68.

Figure 10A:
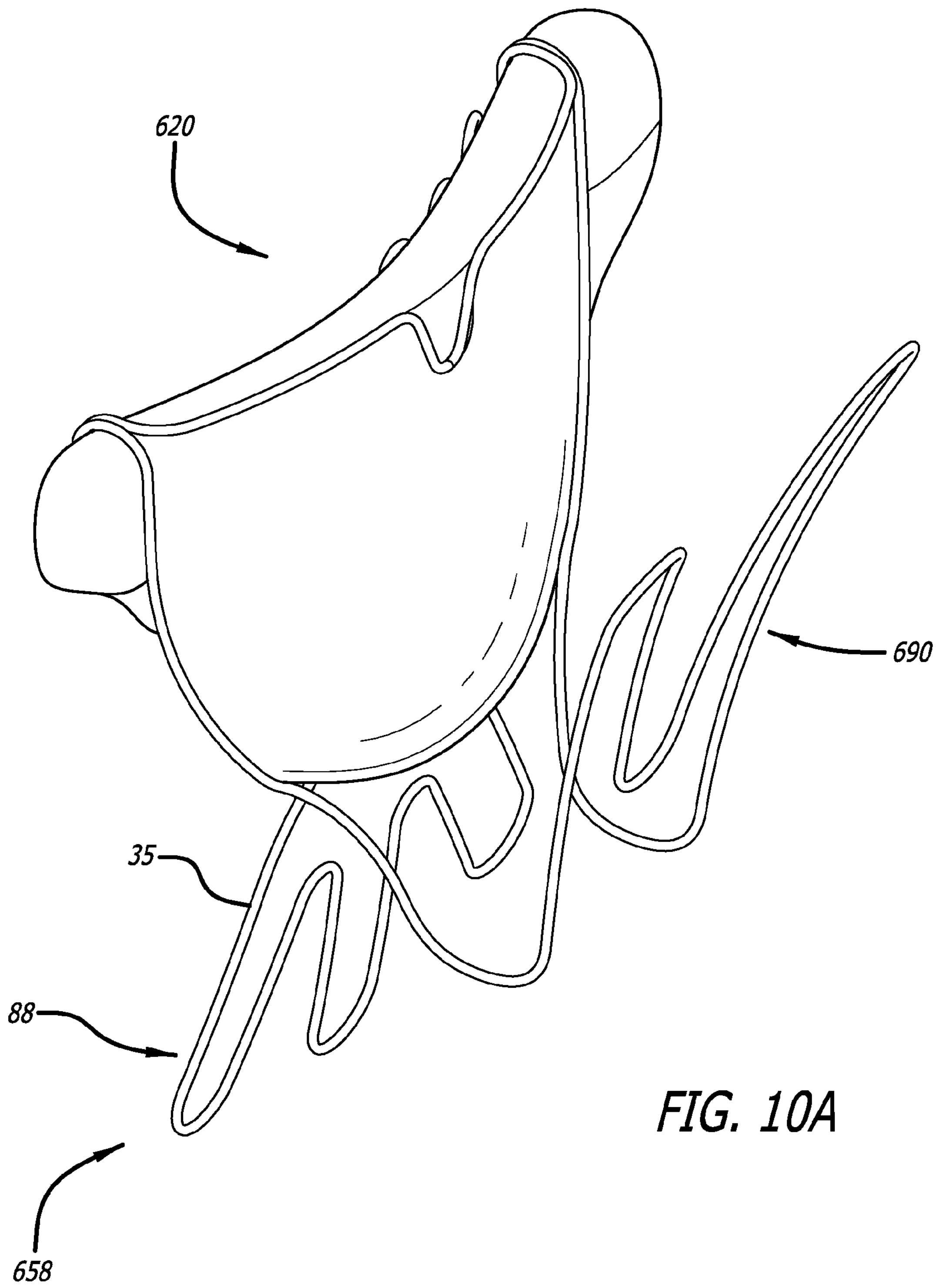
FIGS. 10A-B are schematic illustrations of yet another coaptation-assist device, in accordance with an application of the present invention.
Figure 10B:
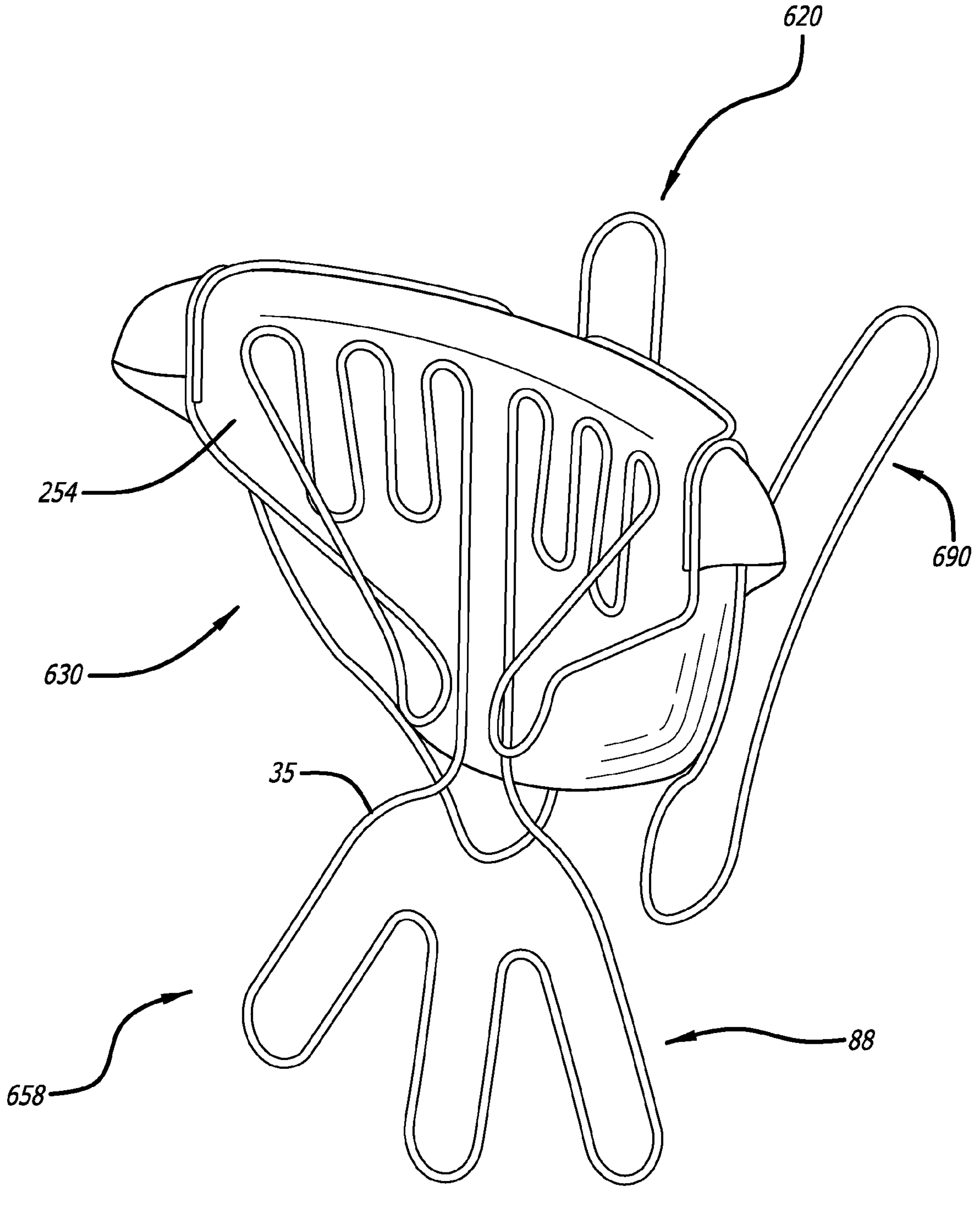

Reference is now made to FIGS. 10A-B, which are schematic illustrations of a coaptation-assist device 620, in accordance with an application of the present invention. Coaptation-assist device 620 is generally similar to coaptation-assist devices 220 and 520, described hereinabove with reference to FIGS. 5A-E and 9A-B, respectively, mutatis mutandis, and like reference numerals refer to like parts. Coaptation-assist device 620, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 620 comprises a ventricular anchor 630, which comprises proximal subannular anchor 254 and a distal anchor 658. Ventricular anchor 630 and proximal subannular anchor 254 may implement any of the features of the ventricular anchors and proximal subannular anchors described herein, mutatis mutandis.

Distal anchor 658 is defined at least in part by at least one of the one or more wires 35. The at least one of the one or more wires 35 that defines distal anchor 658 is shaped as a first distal wire loop 88, which provides distal anchor 658 with a loop-shaped border. Distal wire loop 88 may implement any of the configurations of distal wire loop 88 described hereinabove with reference to FIGS. 1A-C, 2, and/or 3A-C, mutatis mutandis.

The at least one of the one or more wires 35 that defines distal anchor 658 are shaped so as to define a second distal wire loop 690 that is configured to be positioned partially in at least one opposing-leaflet subannular space defined by at least one of the one or more opposing native leaflets, when distal anchor 658 is positioned partially against ventricular wall 27 outside target subannular space 68. Second distal wire loop 690 may implement any of the features of distal wire loop 590, described hereinabove with reference to FIGS. 9A-B.

Figure 11:
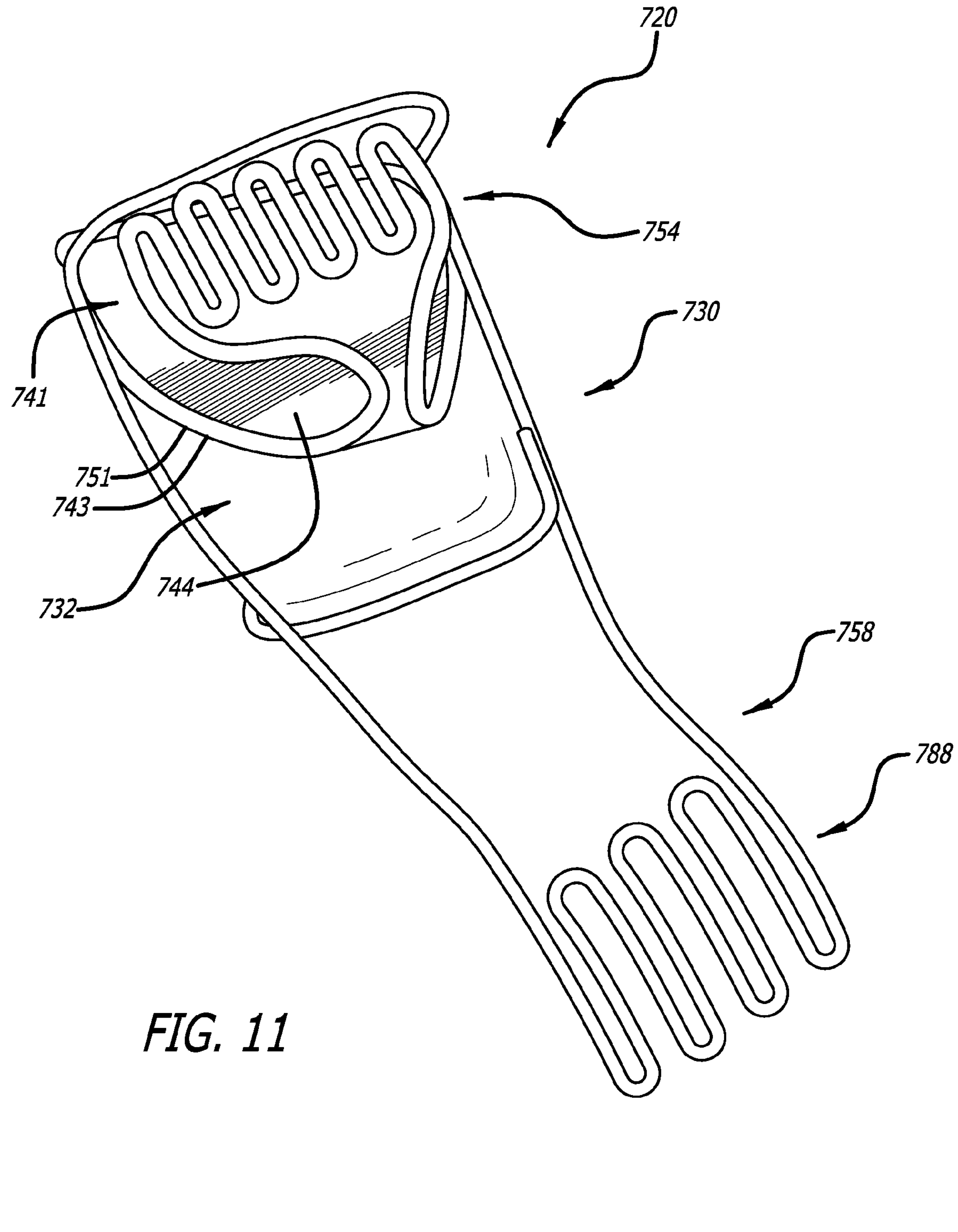
FIG. 11 is a schematic illustration of still another coaptation-assist device, in accordance with an application of the present invention.

Reference is now made to FIG. 11, which is a schematic illustration of a coaptation-assist device 720, in accordance with an application of the present invention. Coaptation-assist device 720, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 720 comprises a ventricular anchor 730 and a neo-leaflet 732. Ventricular anchor 730 comprises a proximal subannular anchor 754 and a distal anchor 758. Neo-leaflet 732 extends directly from and is supported by distal anchor 758. Distal anchor 758 is disposed distally to neo-leaflet 732.

For some applications, as shown, distal anchor 758 comprises distal wire loop 788, which may implement any of the features of distal wire loop 88 described hereinabove with reference to FIGS. 1A-C and 2, mutatis mutandis. For other applications, distal anchor 758 comprises distal wire loop 590, described hereinabove with reference to FIGS. 9A-B. For still other applications, distal anchor 758 comprises both first distal wire loop 88 and second distal wire loop 590, such as described hereinabove with reference to FIGS. 10A-B.

For some applications, coaptation-assist device 720 further comprises an atrial-surface support 741, which is configured to be disposed below an annulus of native atrioventricular valve 22 and against an atrial surface 47 of target native leaflet 26 when proximal subannular anchor 54 is positioned at least partially in target subannular space 68. Atrial-surface support 741 and digitate anchor 56 are configured to grasp and sandwich at least a portion of target native leaflet 26, in order to support neo-leaflet 732, and to orient neo-leaflet 732 with respect to native atrioventricular valve 22. For some applications, atrial-surface support 741 comprises a frame 751 and an atrial-surface cover 744, which is coupled to frame 751. Frame 751 comprises one or more wires 743. Typically, frame 751 defines at least a portion of a border of atrial-surface cover 744. Atrial-surface support 741 and atrial-surface cover 744 may implement any of the features of the atrial-surface supports and atrial-surface covers, respectively, described herein, mutatis mutandis.

Although the coaptation-assist devices described hereinabove have been described as configured to treat a native atrioventricular valve or an aortic valve, they may alternatively be configured to treat other native valves, such a pulmonary valve, such as described hereinbelow. For some such applications, the loop-shaped ventricular anchor is placed upside-down, with the anchor-loop wire loop placed in the outflow artery, i.e., in the aortic root and in the pulmonary artery, respectively, with the grasper grasping one of the cusps of the native valve.

Figure 12A:
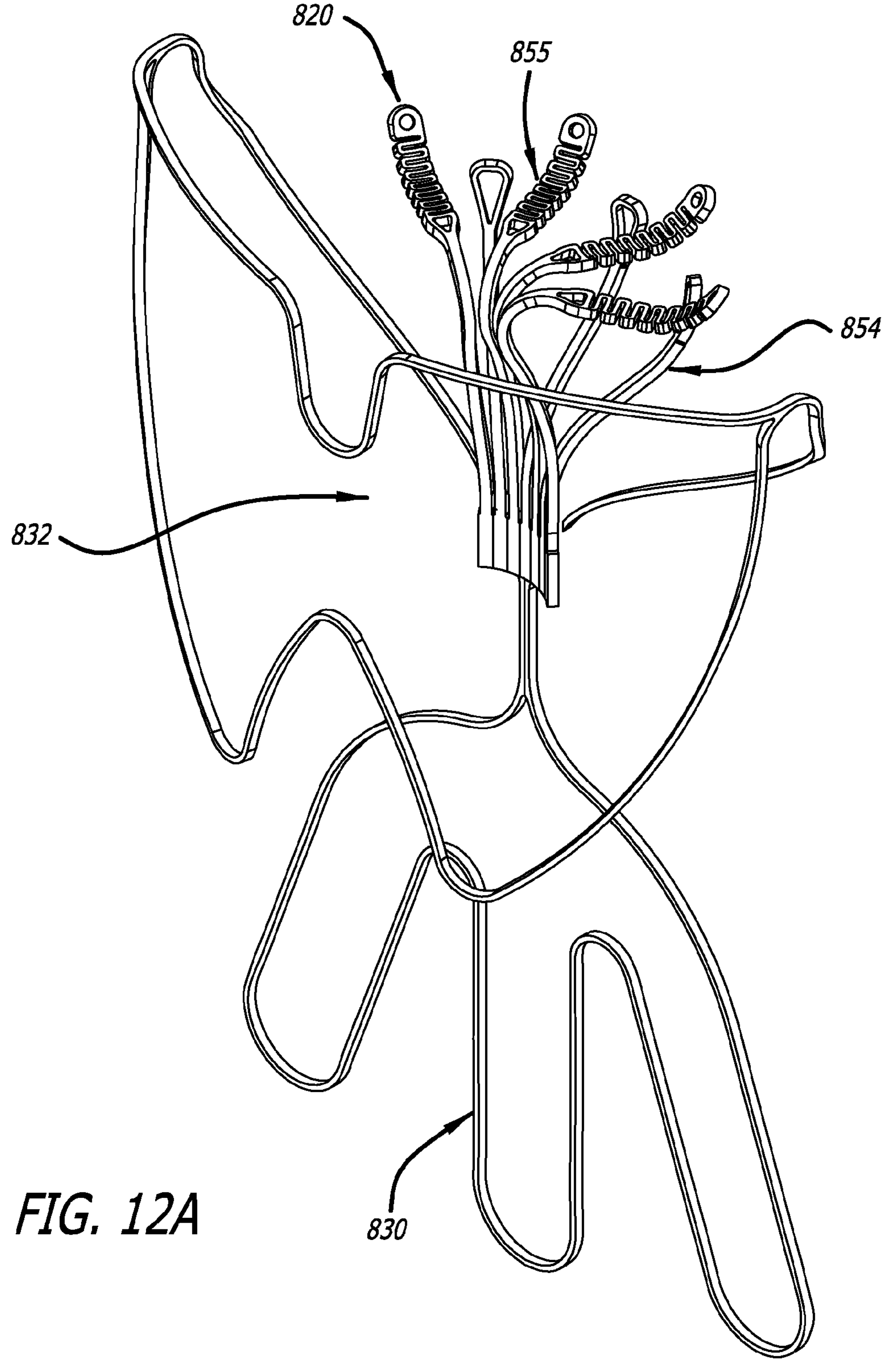
FIGS. 12A-B are schematic illustrations of another coaptation-assist device, in accordance with an application of the present invention.
Figure 12B:

Reference is now made to FIG. 12A-B, which are schematic illustrations of a coaptation-assist device 820, in accordance with an application of the present invention. Coaptation-assist device 820, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 820 comprises a proximal subannular anchor 854 and proximal supra-leaflet atrial support 855. A ventricular anchor 830 and a neo-leaflet 832 extend directly from and are supported by the anchor assembly 854 and 855.

For some applications, as shown, proximal anchor 854 comprises one or more wires—three are shown in the figure—that define the proximal anchoring support, to be placed below the native leaflet, among the chordae tendineae, to arrive to the base of the native leaflet, and supra-leaflet atrial support 855, to tension and support the neo-leaflet component present between 854 and 855 against the atrial surface of the native leaflet once implanted. Supra-leaflet atrial support 855 comprises one or more wires or laser cut elements—four are shown in the figure—shaped as to create a tensioning and compressing structure directed towards the atrial surface of the native leaflet to arrive to the basal annular part of the native leaflet.

Figure 13A:
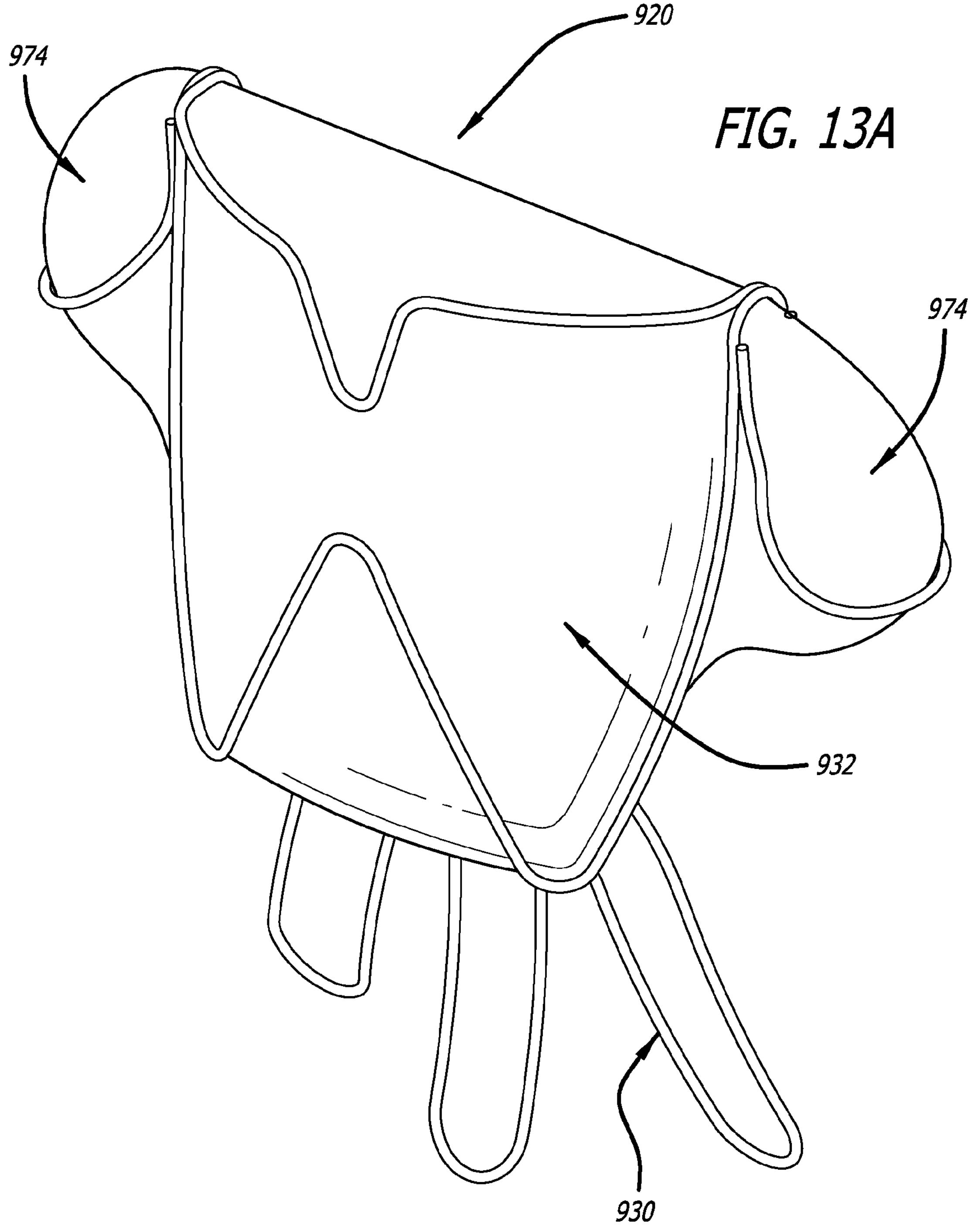
FIGS. 13A-B are schematic illustrations of another coaptation-assist device, in accordance with an application of the present invention.
Figure 13B:
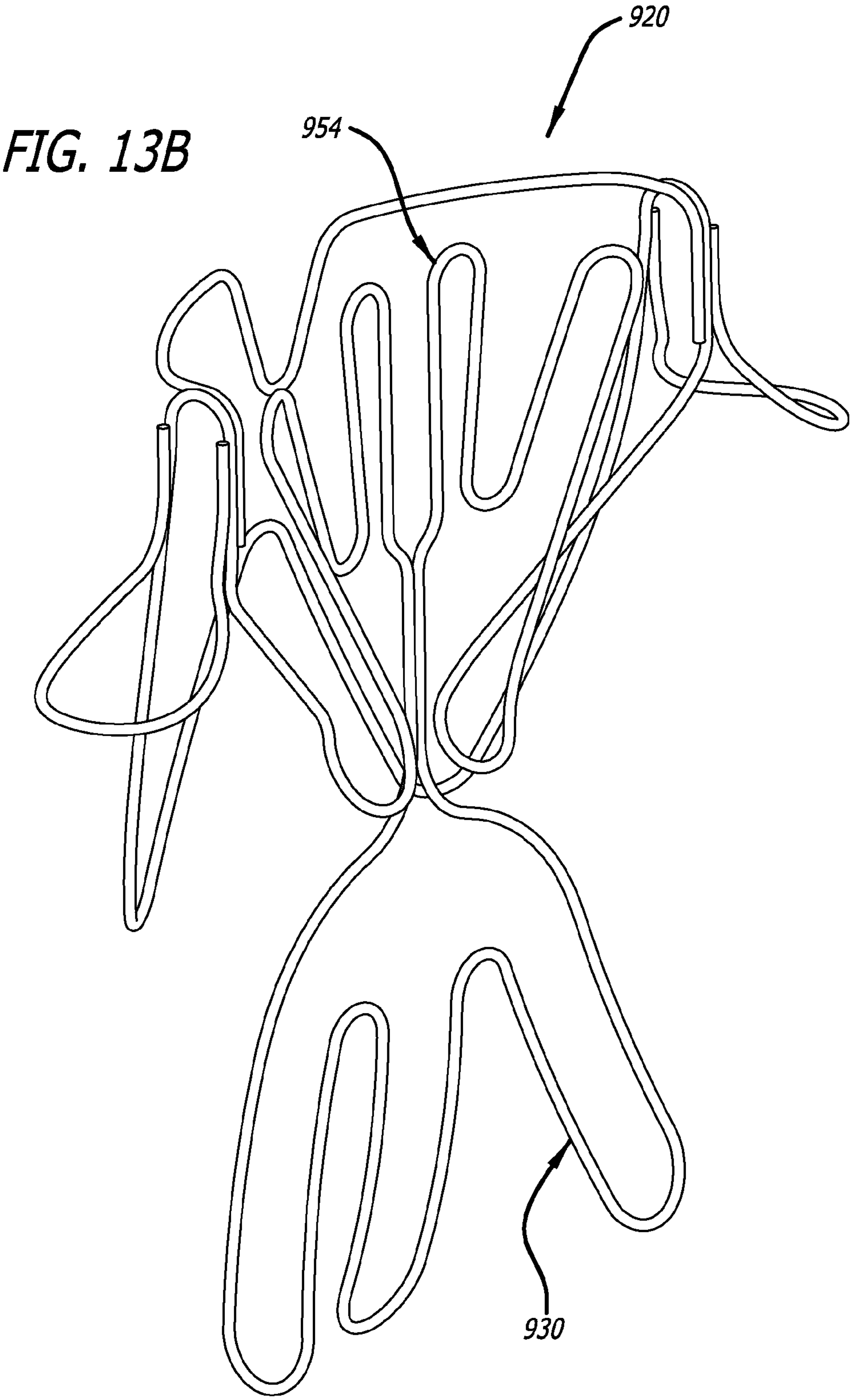

Reference is made to FIG. 13A-B, which are schematic illustrations of a coaptation-assist device 920, In accordance with an application of the present invention. Coaptation-assist device 920, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

For some applications, as shown, a proximal subannular anchor 954 and the body of a neo-leaflet frame 932 are shaped so to engage and cover partially the target native leaflet, typically centrally, leaving the side commissural native leaflet not touched by these components. Two large parachute neo-leaflet components 974 are connected to the neo-leaflet frame, to inflate and deflate during the cardiac cycle, intended to covering the remaining portion of the native leaflet, from the end of the neo-leaflet component to proximal to each of the native valve commissures, surrounding and covering the regurgitation area around the commissures. For some applications, a ventricular loop 930 is shaped so as to define one or more lobes—three lobes shown in the figures—which are shaped not to be aligned in the same plane, but to have a spatial distribution to approximate the ventricular area in three different points not aligned in the same plane.

Figure 14A:
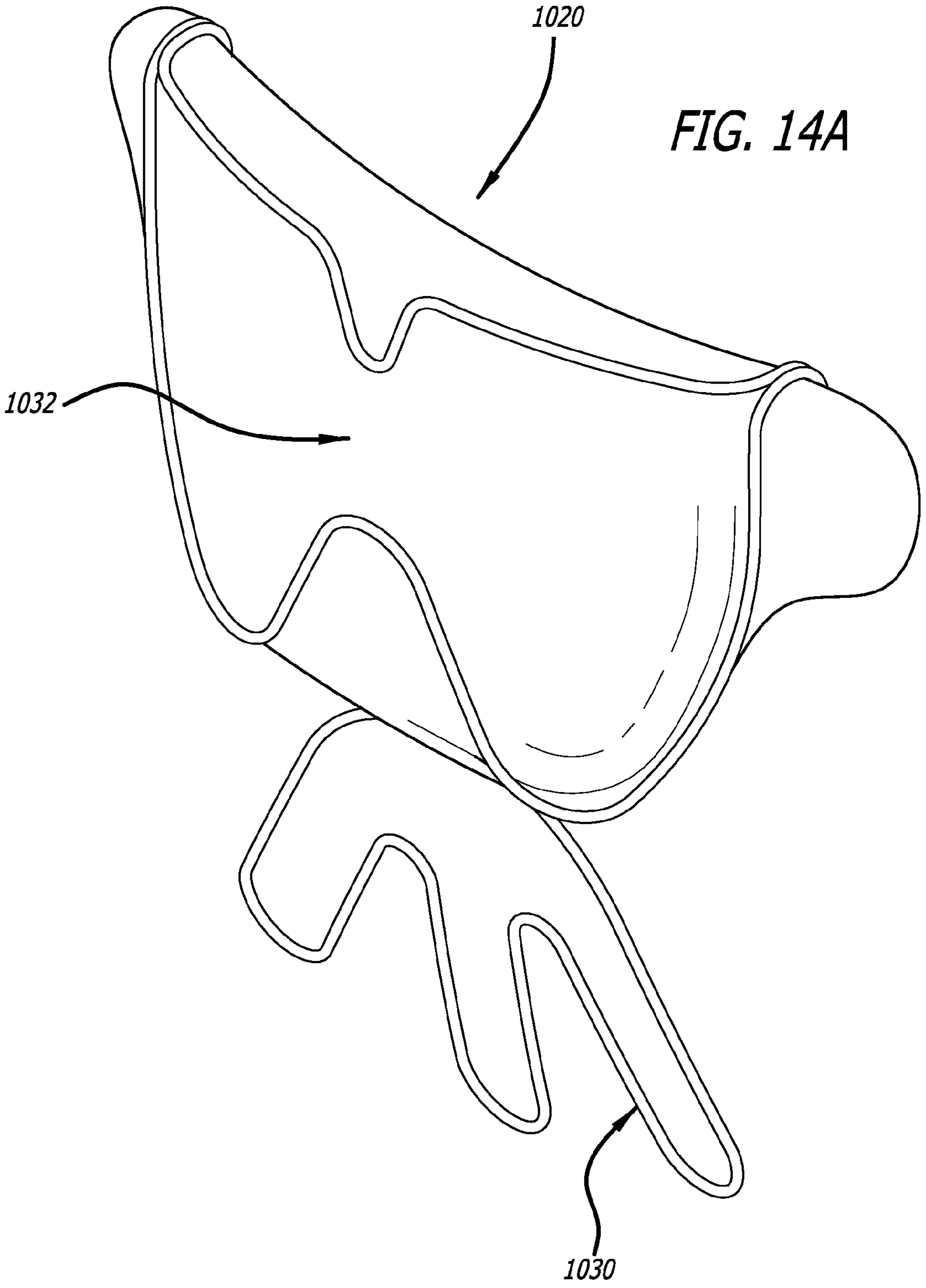
FIGS. 14A-B are schematic illustrations of yet another coaptation-assist device, in accordance with an application of the present invention.
Figure 14B:
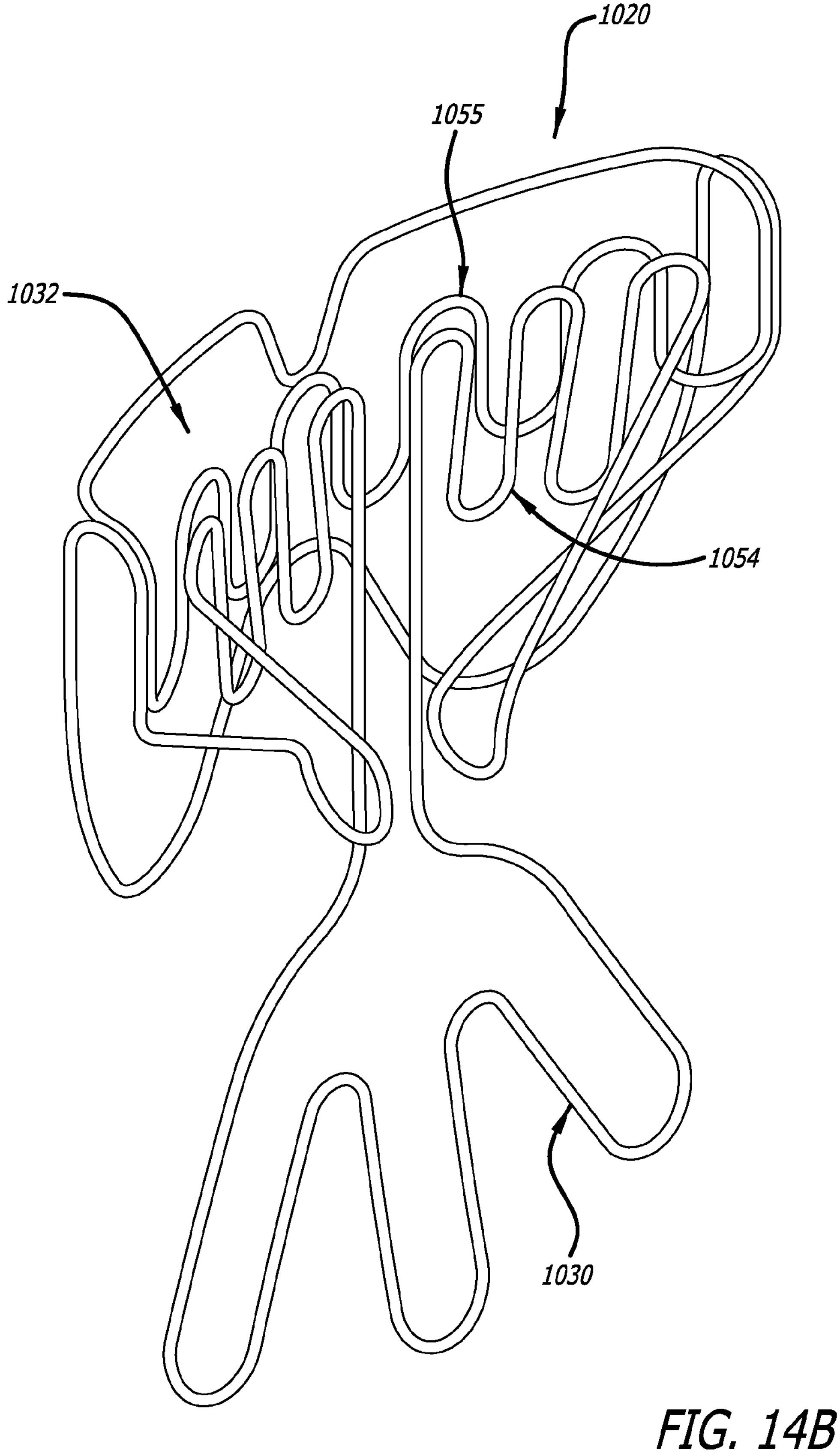

Reference is now made to FIG. 14A-B, which are schematic illustrations of a coaptation-assist device 1020, in accordance with an application of the present invention. Coaptation-assist device 1020, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 1020 comprises a proximal subannular anchor 1054 and a proximal supra-leaflet support 1055. A ventricular anchor 1030 and a neo-leaflet 1032 extend directly from and are supported by the anchor assembly 1054 and 1055.

For some applications, as shown, proximal subannular anchor 1054 comprises one or more wires that define the proximal anchoring support, to be placed below the native leaflet, among the chordae tendineae, to arrive to the base of the native leaflet, and supra-leaflet support 1055, to support the neo-leaflet component present between proximal subannular anchor 1054 and proximal supra-leaflet support 1055 and to compress it against the atrial surface of the native leaflet once implanted. Supra-leaflet support 1055 comprises one or more wires shaped as to create a compressing structure directed towards the atrial surface of the native leaflet to provide a counter element which can compress against proximal subannular anchor 1054.

Figure 15A:
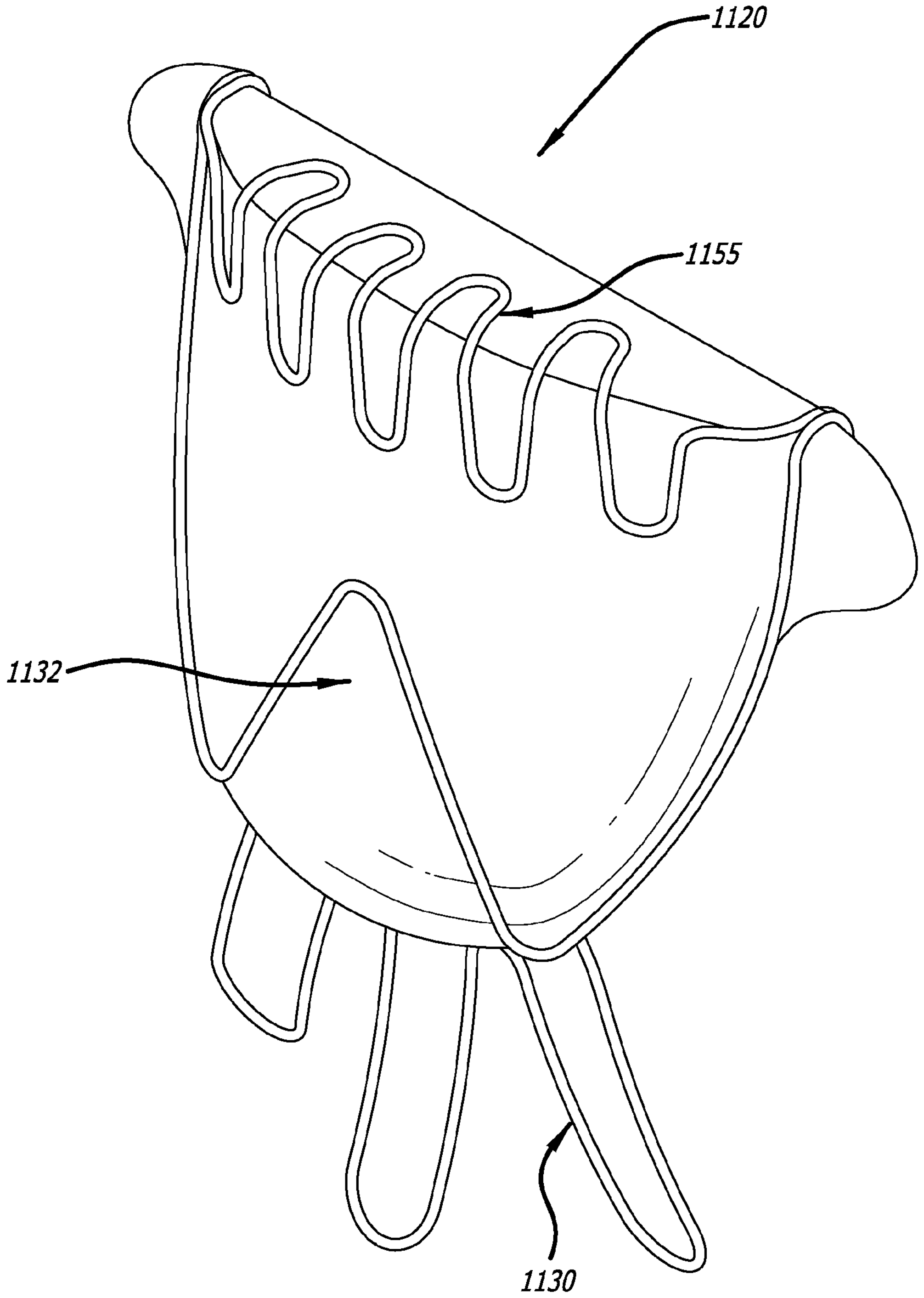
FIGS. 15A-B are schematic illustrations of still another coaptation-assist device, in accordance with an application of the present invention.
Figure 15B:
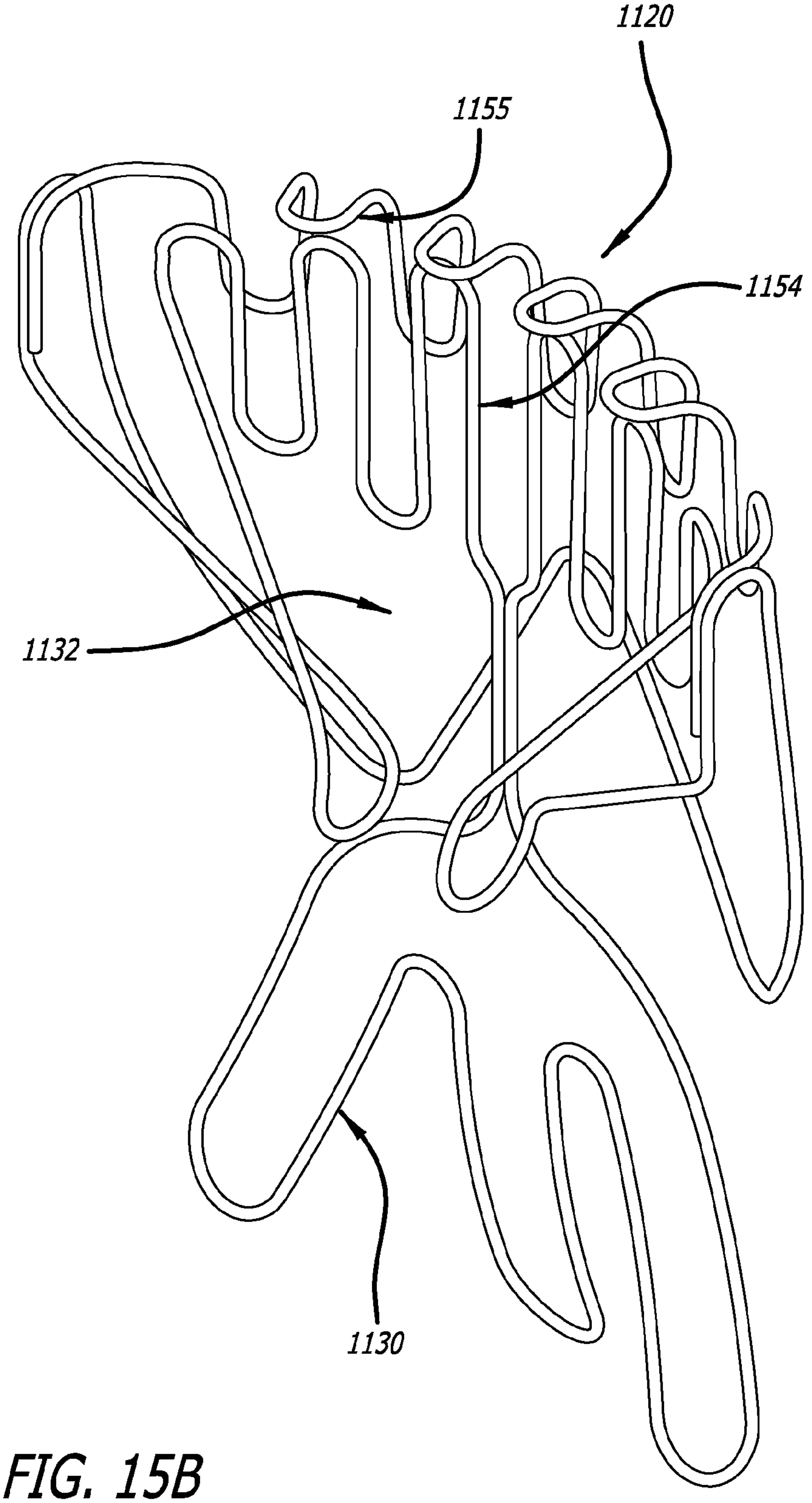

Reference is now made to FIG. 15A-B, which are schematic illustrations of a coaptation-assist device 1120, in accordance with an application of the present invention. Coaptation-assist device 1120, including its neo-leaflet and loop-shaped ventricular anchor, may implement (a) any of the features of coaptation-assist device 20, mutatis mutandis, including the features described hereinabove with reference to FIGS. 3A-C, mutatis mutandis, and/or (b) any of the features of the other coaptation-assist devices described herein, mutatis mutandis.

Coaptation-assist device 1120 comprises a proximal subannular anchor 1154 and a proximal supra-leaflet support 1155. A proximal ventricular anchor 1130 and a neo-leaflet 1132 extend directly from and are supported by the anchor assembly 1154 and 1155.

For some applications, as shown, proximal subannular anchor 1154 comprises one or more wires that define the proximal anchoring support, to be placed below the native leaflet, among the chordae tendineae, to arrive to the base of the native leaflet, and supra-leaflet support 1155, to support the neo-leaflet component present between 1154 and 1155, arriving to provide compression force up to the annular base of the native leaflet and to compress it against the atrial surface of the native leaflet once implanted. Supra-leaflet support 1055 comprises one or more wires shaped as to create a compressing structure directed towards the atrial surface of the native leaflet up to the originating annulus, to provide a counter element which can compress against subannular anchor 1054.

Figure 16A:
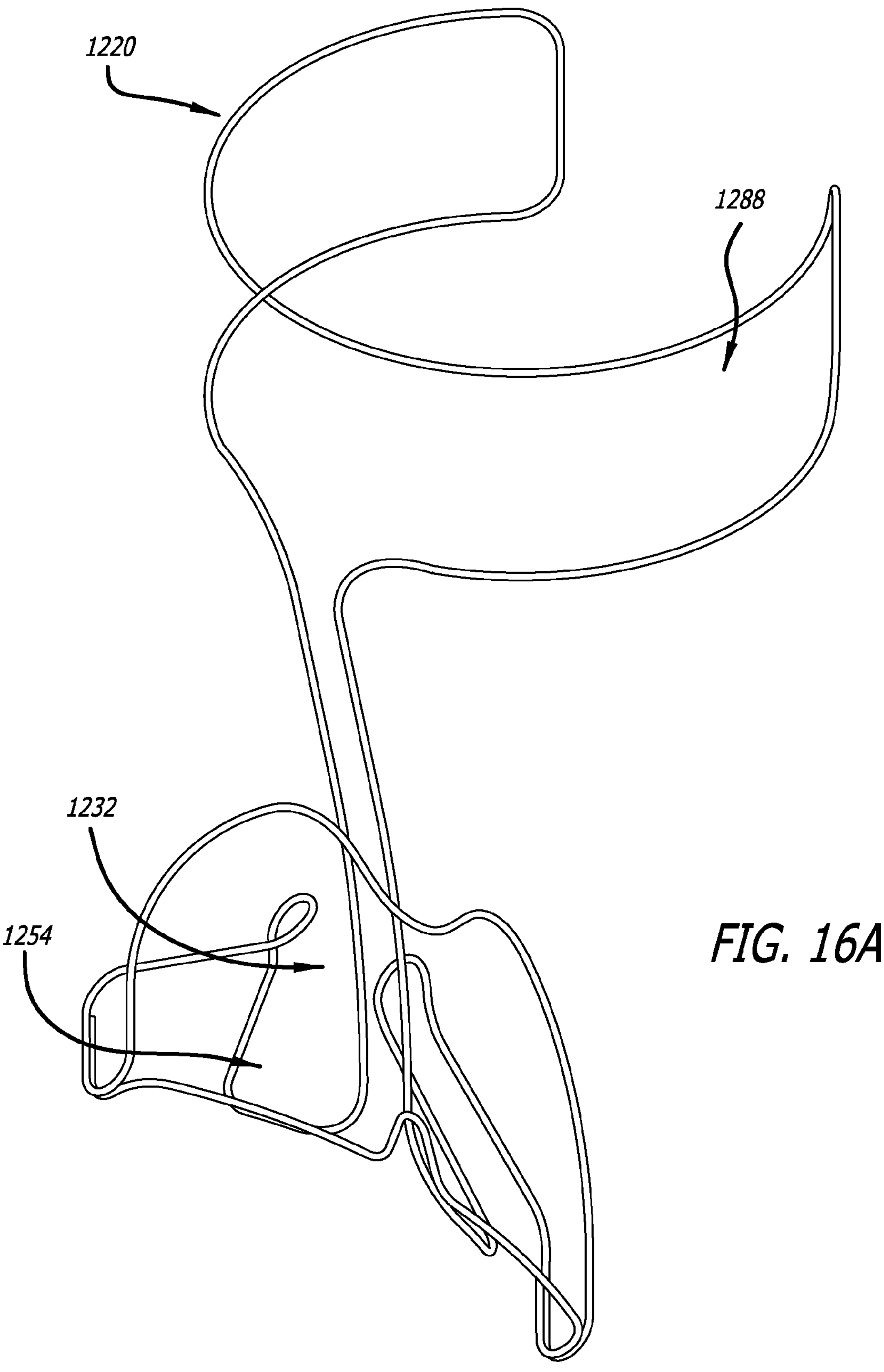
FIGS. 16A-B are schematic illustrations of coaptation-assist devices for treating a native aortic or pulmonary valve of a subject, in accordance with respective applications of the present invention.

Reference is now made to FIG. 16A, which is a schematic illustration of a coaptation-assist device 1220 to treat an aortic valve, in accordance with an application of the present invention. Other than as described hereinbelow, components of the coaptation-assist device 1220 are generally similar to coaptation-assist device 20, described hereinabove with reference to FIGS. 1A-C and 2, and like reference numerals refer to like parts. Coaptation-assist device 1220 may implement any of the features of coaptation-assist device 20, mutatis mutandis, including the features described hereinabove with reference to FIGS. 3A-C, mutatis mutandis. The targeted implantation anatomy and the interaction between each component and the native valvular anatomy will be different, to adapt it to the treatment of an aortic or pulmonary valve.

Coaptation-assist device 1220 comprises a neo-leaflet 1232, which is supported by an aortic anchor 1230. Aortic anchor 1230 comprises a proximal aortic-sinus anchor 1254 and a loop-shaped aortic anchor 1258, which comprises an anchor-loop wire loop, which (i) defines at least a portion of a border of the loop-shaped aortic anchor, and (ii) is configured (a) to be positioned in an aorta (the ascending aorta and/or the aortic arch) and (b) to remain anchored in position against an aortic wall. Aortic-sinus anchor 1254 is configured to be positioned at least partially in an aortic sinus of a target native aortic leaflet (which is also known in the art as a cusp). For some applications, aortic-sinus anchor 1254 comprises a digitate anchor 1256, including two or more wire loops. Aortic anchor 1230, aortic-sinus anchor 1254, digitate anchor 1256, and loop-shaped aortic anchor 1258 may implement any of the features of ventricular anchor 30, proximal subannular anchor 54, digitate anchor 56, and/or distal anchor 58, respectively, described hereinabove with reference to FIGS. 1A-C, 2, and/or 3A-C, mutatis mutandis. For some applications, such as shown in FIG. 4, loop-shaped aortic anchor 1258 is defined at least in part by at least one of the one or more wires 35.

For some these applications, the at least one of the one or more wires that defines loop-shaped aortic anchor 1258 is shaped as distal wire loop 1288, which provides loop-shaped aortic anchor 1258 with a loop-shaped border, shaped to cover and expand radially along a section of the aorta, such as including the aortic arch.

For some these applications, the at least one of the one or more wires that defines loop-shaped aortic anchor 1258 is shaped as multiple distal wire loops 1288, which provide loop-shaped aortic anchor 1258 with a loop-shaped border which overall and cover a longer section of the aorta, such as including the aortic arch, where they expand to keep in position and stabilize the device.

For some application, aortic-sinus anchor 1254 is shaped as a digitate wire, to expand along the subannular space of the native targeted cusp.

For some applications, aortic-sinus anchor 1254 is configured such that, when the aortic-sinus anchor is positioned at least partially in the aortic sinus, the aortic-sinus anchor applies a force to sinus-facing surface of the target native aortic leaflet, so as to help anchor the aortic-sinus anchor to the target native aortic leaflet. For some of these applications, the aortic-sinus anchor comprises a digitate anchor that is shaped so as to define a plurality of fingers having a plurality of curved inferior peaks that point in an inferior direction and engage one or more sinus surfaces selected from the group consisting of: an aortic wall, a sinus-facing surface of the target native aortic leaflet, and a floor of the aortic sinus.

For some applications, coaptation-assist device 1220 further comprises a leaflet-surface support, which is configured to be disposed centrally to the target native aortic valve and against a coapting surface of the target native aortic leaflet when the aortic-sinus anchor is positioned at least partially in the aortic sinus. The leaflet-surface support and the aortic-sinus anchor are configured to grasp and sandwich at least a portion of the target native aortic leaflet, in order to support the neo-leaflet. Typically, the leaflet-surface support comprises a frame and a cover, which is coupled to the frame.

Figure 16B:
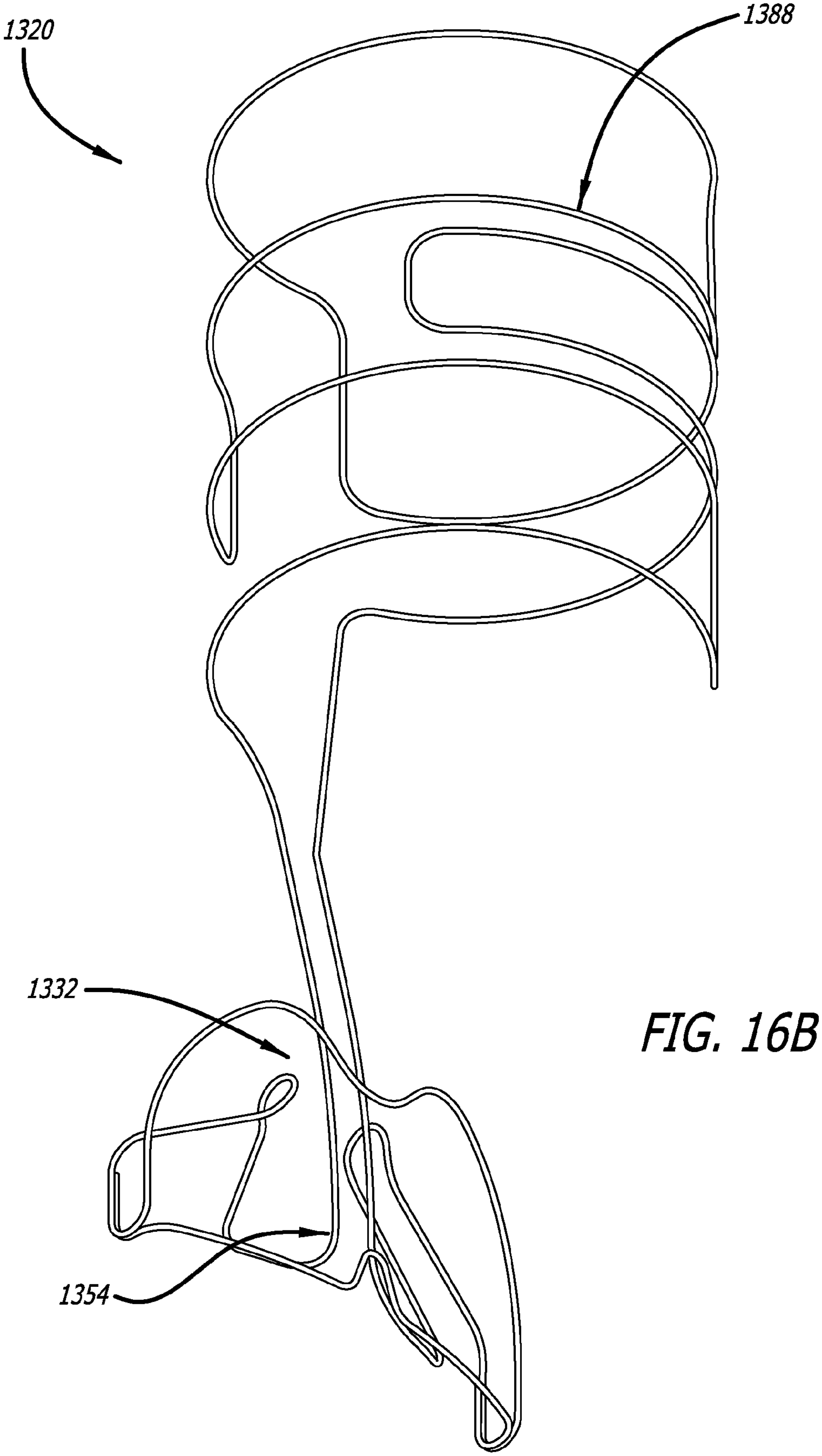

Reference is now made to FIG. 16B, which is a schematic illustration of a coaptation-assist device 1320 to treat an aortic valve, in accordance with an application of the present invention. Other than as described hereinbelow, components of the coaptation-assist device 1320 are generally similar to coaptation-assist device 20, described hereinabove with reference to FIGS. 1A-C and 2, and like reference numerals refer to like parts. Coaptation-assist device 1320 may implement any of the features of coaptation-assist device 20, mutatis mutandis, including the features described hereinabove with reference to FIGS. 3A-C, mutatis mutandis. The targeted implantation anatomy and the interaction between each component and the native valvular anatomy will be different, to adapt it to the treatment of an aortic or pulmonary valve.

Coaptation-assist device 1320 comprises a neo-leaflet 1332, which is supported by an aortic anchor 1330. Aortic anchor 1330 comprises a proximal aortic-sinus anchor 1354 and a loop-shaped aortic anchor 1358, which comprises an anchor-loop wire loop, which (i) defines at least a portion of a border of the loop-shaped aortic anchor, and (ii) is configured (a) to be positioned in an aorta (the ascending aorta and/or the aortic arch) and (b) to remain anchored in position against an aortic wall. Aortic-sinus anchor 1254 is configured to be positioned at least partially in an aortic sinus of a target native aortic leaflet (which is also known in the art as a cusp). For some applications, aortic-sinus anchor 1354 comprises a digitate anchor 1356, including two or more wire loops. Aortic anchor 1330, aortic-sinus anchor 1354, digitate anchor 1356, and loop-shaped aortic anchor 1358 may implement any of the features of ventricular anchor 30, proximal subannular anchor 54, digitate anchor 56, and/or distal anchor 58, respectively, described hereinabove with reference to FIGS. 1A-C, 2, and/or 3A-C, mutatis mutandis. For some applications, such as shown in FIG. 4, distal anchor 158 is defined at least in part by at least one of the one or more wires 35.

For some these applications, the at least one of the one or more wires that defines loop-shaped aortic anchor 1358 is shaped as multiple distal wire loop 1388, which provides loop-shaped aortic anchor 1358 with a loop-shaped border, to cover and expand radially along a wide section of the aorta, such as including the aortic arch, for device stabilization For some application, aortic-sinus anchor 1354 is shaped as a digitate wire, to expand along the sub-annular space of the native targeted cusp.

For some applications, aortic-sinus anchor 1354 is configured such that, when the aortic-sinus anchor is positioned at least partially in the aortic sinus, the aortic-sinus anchor applies a force to sinus-facing surface of the target native aortic leaflet, so as to help anchor the aortic-sinus anchor to the target native aortic leaflet. For some of these applications, the aortic-sinus anchor comprises a digitate anchor that is shaped so as to define a plurality of fingers having a plurality of curved inferior peaks that point in an inferior direction and engage one or more sinus surfaces selected from the group consisting of: an aortic wall, a sinus-facing surface of the target native aortic leaflet, and a floor of the aortic sinus.

For some applications, coaptation-assist device 1320 further comprises a leaflet-surface support, which is configured to be disposed centrally to the target native aortic valve and against a coapting surface of the target native aortic leaflet when the aortic-sinus anchor is positioned at least partially in the aortic sinus. The leaflet-surface support and the aortic-sinus anchor are configured to grasp and sandwich at least a portion of the target native aortic leaflet, in order to support the neo-leaflet. Typically, the leaflet-surface support comprises a frame and a cover, which is coupled to the frame.

Figure 16C:
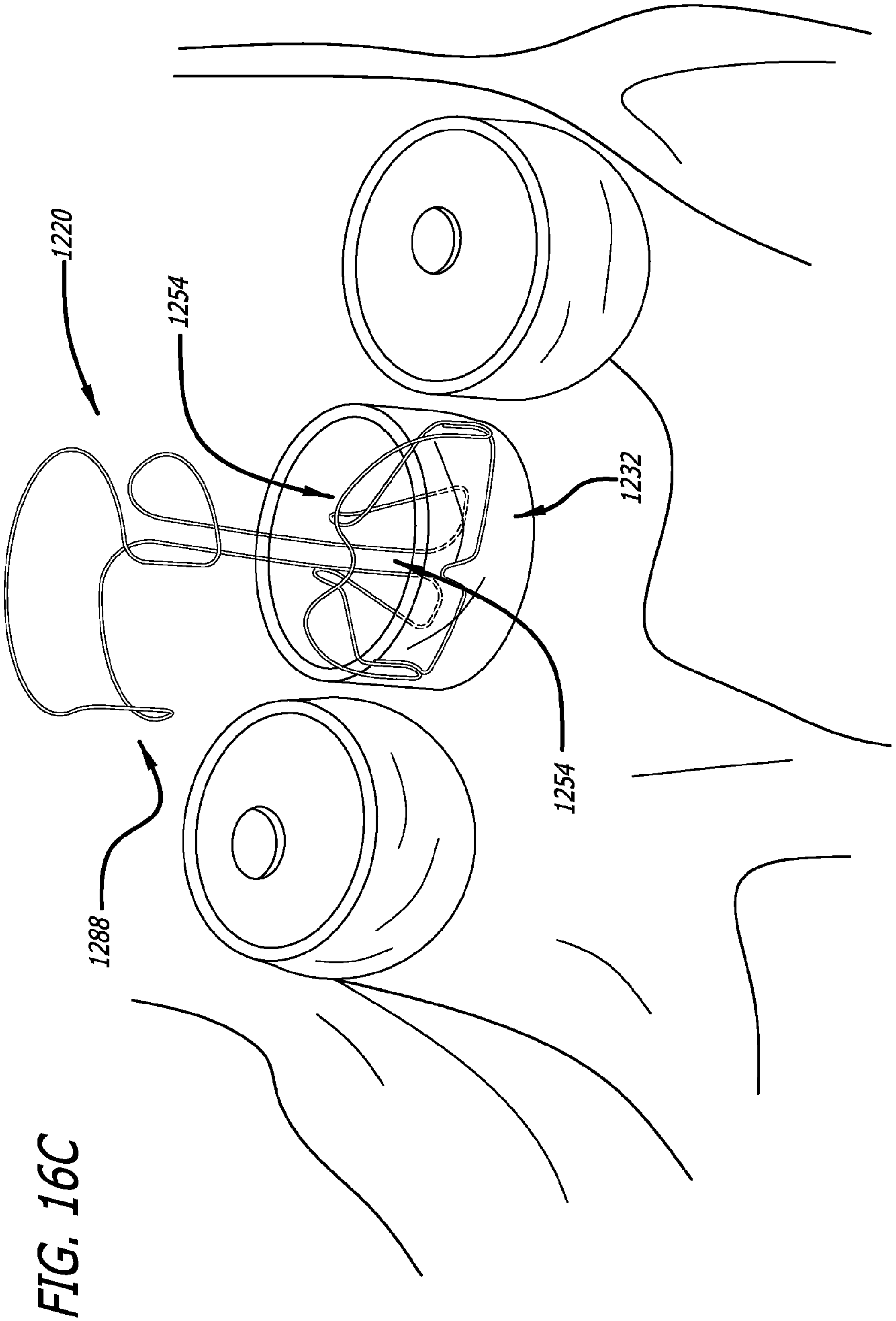
FIG. 16C is a schematic illustration of the coaptation-assist device of FIG. 16A implanted in a native aortic valve, in accordance with an application of the present invention.

Reference is now made to FIG. 16C, which is a schematic illustration of coaptation-assist device 1220, described hereinabove with reference to FIG. 16A, implanted in a native aortic valve, in accordance with an application of the present invention. Coaptation-assist device 1320, described hereinabove with reference to FIG. 16B, may be implanted in a similar matter, mutatis mutandis.

Figure 17:
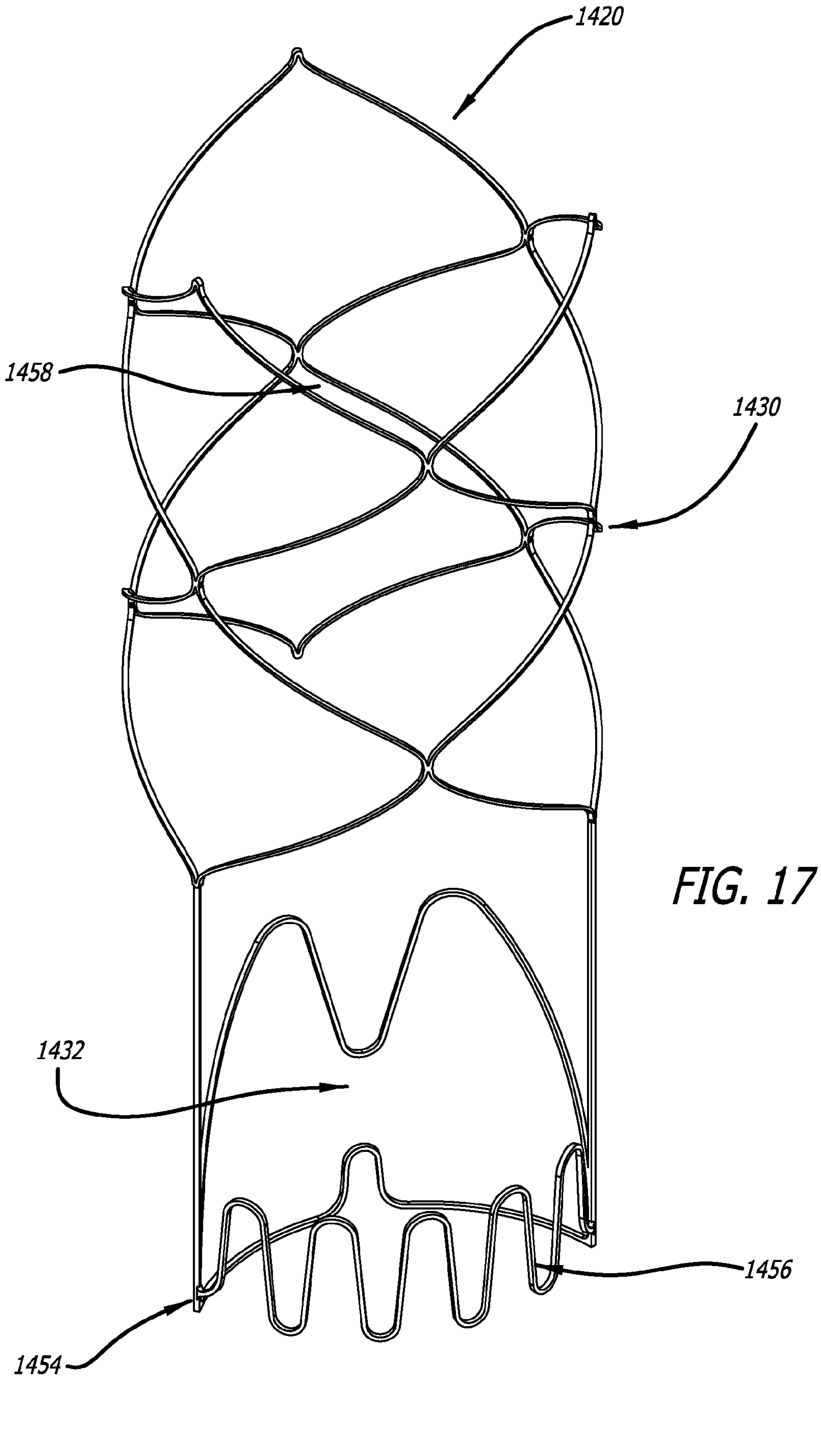
FIG. 17 is a schematic illustration of yet another aortic-pulmonary valve coaptation-assist device, in accordance with an application of the present invention.

Reference is now made to FIG. 17, which is a schematic illustration of a coaptation-assist device 1420 to treat an aortic valve, in accordance with an application of the present invention. Other than as described hereinbelow, components of coaptation-assist device 1420 are generally similar to coaptation-assist devices 1220 and 1320, described hereinabove with reference to FIGS. 16A-B, respectively. Coaptation-assist device 1420 may implement any of the features of coaptation-assist device 1220 and 1320, mutatis mutandis, Coaptation-assist device 1420 comprises a neo-leaflet 1432, which is supported by an aortic stent-like anchor 1430. Aortic anchor 1430 comprises an aortic-sinus anchor 1454 and a closed-loop anchor 1458 distally positioned in the aorta, such as including the aortic arch. For some applications, aortic-sinus anchor 1454 comprises a digitate anchor 1456, including two or more wire loops. The stent-like structure of aortic anchor 1430 is configured to provide radial force against a section of the landing in the aorta, such as in the aortic arch, in order to stabilize the device.

For some applications, coaptation-assist devices 1220, 1320, and/or 1420, shown in FIGS. 16A, 16B, and 17, respectively, are configured to treat a native pulmonary valve.

For some applications, a method is provided that comprises:

positioning a loop-shaped pulmonary-artery anchor of a coaptation-assist device in an pulmonary artery, such that an anchor-loop wire loop of the loop-shaped pulmonary-artery remains anchored in position against a pulmonary wall, wherein the anchor-loop wire loop defines at least a portion of a border of the loop-shaped pulmonary-artery anchor;

positioning a pulmonary-sinus anchor of the coaptation-assist device at least partially in a pulmonary sinus of a target native pulmonary leaflet; and positioning a neo-leaflet of the coaptation-assist device such that the neo-leaflet at least partially replaces function of the target native leaflet by providing a surface of coaptation opposing one or more native pulmonary leaflets that oppose the target native pulmonary leaflet, when anchored in place by the loop-shaped pulmonary-artery anchor and the pulmonary-sinus anchor.

The scope of the present invention includes embodiments described in the following applications, which are incorporated herein by reference. In an embodiment, techniques and apparatus described in one or more of the following applications are combined with techniques and apparatus described herein:

US Patent Application Publication 2016/0302917

US Patent Application Publication 2019/0350705

U.S. Provisional Application 62/792,092, filed Jan. 14, 2019

U.S. Provisional Application 62/884,404, filed Aug. 8, 2019

International Application PCT/IL2020/050057, filed Jan. 14, 2020

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A coaptation-assist device for treating a native atrioventricular valve of a heart, the coaptation-assist device comprising:

a ventricular anchor, which comprises one or more wires, and which is configured to be positioned in a ventricle of the heart; and a neo-leaflet, which is supported by the ventricular anchor and is configured to at least partially replace function of a target native leaflet of the native atrioventricular valve by providing a surface of coaptation for one or more opposing native leaflets that oppose the target native leaflet, when anchored in place by the ventricular anchor, wherein the ventricular anchor comprises:

a proximal subannular anchor, which (a) comprises a digitate anchor that (i) is defined at least in part by at least one of the one or more wires, and (ii) is shaped so as to define a plurality of fingers having a plurality of curved superior peaks, and (b) is configured to be positioned at least partially in a target subannular space defined by the target native leaflet and a superior portion of a ventricular wall of the ventricle, such that (i) the curved superior peaks point in a superior direction and engage a subannular surface of the target native leaflet, and (ii) one or more of the fingers engage chordae tendineae that extend between the target native leaflet and the superior portion of the ventricular wall, so as to stabilize the coaptation-assist device, and a distal anchor, which is configured to be positioned partially against the ventricular wall outside the target subannular space, so as to push on the proximal subannular anchor to help anchor the proximal subannular anchor in place within the target subannular space.

2. The coaptation-assist device according to claim 1, wherein the plurality of curved superior peaks comprises between four and twelve curved superior peaks.

3. The coaptation-assist device according to claim 1, wherein when the fingers are unconstrained:

the fingers have respective greatest widths and respective heights, the greatest widths measured laterally, the respective heights measured in a superior-inferior direction, the fingers have respective ratios of the heights to the greatest widths, and an average of the respective ratios is between 2 and 5.

4. The coaptation-assist device according to claim 1, wherein the distal anchor is configured to contact the ventricular wall inferior to the target subannular space.

5. The coaptation-assist device according to claim 1, wherein the coaptation-assist device does not comprise any elements that are configured to penetrate tissue.

6. The coaptation-assist device according to claim 1, wherein at least half of the fingers terminate superiorly to an inferior edge of the surface of coaptation of the neo-leaflet.

7. The coaptation-assist device according to claim 1, wherein the digitate anchor is serpentine, and is shaped so as to define a plurality of undulations having the plurality of curved superior peaks connected to a plurality of inferior troughs by respective segments.

8. The coaptation-assist device according to claim 7, wherein when the undulations are unconstrained:

the undulations have respective greatest widths and respective heights, the greatest widths measured between adjacent pairs of the segments connected by respective curved peaks, the respective heights measured in a superior-inferior direction, the undulations have respective ratios of the heights to the greatest widths, and an average of the respective ratios is between 2 and 5.

9. The coaptation-assist device according to claim 7, wherein at least half of the inferior troughs terminate superiorly to an inferior edge of the surface of coaptation of the neo-leaflet.

10. The coaptation-assist device according to claim 1, wherein the at least one of the one or more wires that defines the distal anchor is shaped as a distal wire loop.

11. The coaptation-assist device according to claim 10, wherein the distal wire loop is configured to be positioned in the ventricle, extending to a ventricular apical area.

12. The coaptation-assist device according to claim 11, wherein the distal wire loop is shaped so as to define three or more lobes.

13. The coaptation-assist device according to claim 1, wherein a continuous portion of the one or more wires is shaped so as to define both the distal anchor and the proximal subannular anchor.

14. The coaptation-assist device according to claim 1, wherein the proximal subannular anchor is configured such that, when the proximal subannular anchor is positioned at least partially in the target subannular space, the digitate anchor applies a force to a ventricular surface of the target native leaflet, so as to help anchor the ventricular anchor to the target native leaflet.

15. The coaptation-assist device according to claim 14, further comprising an atrial-surface support, which is configured to be disposed below an annulus of the native atrioventricular valve and against an atrial surface of the target native leaflet when the proximal subannular anchor is positioned at least partially in the target subannular space, wherein the atrial-surface support and the digitate anchor are configured to grasp and sandwich at least a portion of the target native leaflet, in order to support the neo-leaflet, and to orient the neo-leaflet with respect to the native atrioventricular valve.

16. The coaptation-assist device according to claim 15, wherein the atrial-surface support comprises a frame and an atrial-surface cover, which is coupled to the frame.

17. The coaptation-assist device according to claim 1, wherein the coaptation-assist device is configured such that the coaptation surface of the neo-leaflet crosses from an atrial side to a ventricular side of a native valvular plane, when anchored in place by the ventricular anchor.

18. The coaptation-assist device according to claim 1, wherein the neo-leaflet comprises:

a neo-leaflet wire loop that defines at least a portion of a border of the neo-leaflet; and a neo-leaflet cover, which is attached to the neo-leaflet wire loop and provides the surface of coaptation.

19. The coaptation-assist device according to claim 1, further comprising a pouch, which is configured to inflate by blood flow during a cardiac cycle of the heart, so as to push the coaptation-assist device against one or more of: a ventricular surface of the target native leaflet and an annulus of the native atrioventricular valve, thereby stabilizing the coaptation-assist device with respect to the native atrioventricular valve.

20. A method for treating a native atrioventricular valve of a heart, the method comprising:

advancing, to within the heart, a coaptation-assist device that comprises a ventricular anchor, which comprises (a) one or more wires, (b) a proximal subannular anchor, which comprises a digitate anchor that (i) is defined at least in part by at least one of the one or more wires, and (ii) is shaped so as to define a plurality of fingers having a plurality of curved superior peaks, and (c) a distal anchor;

positioning the ventricular anchor in a ventricle of the heart such that:

the proximal subannular anchor is positioned at least partially in a target subannular space defined by a target native leaflet of the native atrioventricular valve and a superior portion of a ventricular wall of the ventricle, such that (i) the curved superior peaks point in a superior direction and engage a subannular surface of the target native leaflet, and (ii) one or more of the fingers engage chordae tendineae that extend between the target native leaflet and the superior portion of the ventricular wall, so as to stabilize the coaptation-assist device, the distal anchor is positioned partially against the ventricular wall outside the target subannular space, so as to push on the proximal subannular anchor to help anchor the proximal subannular anchor in place within the target subannular space; and positioning a neo-leaflet of the coaptation-assist device such that the neo-leaflet at least partially replaces function of the target native leaflet by providing a surface of coaptation for one or more opposing native leaflets that oppose the target native leaflet, when supported and anchored in place by the ventricular anchor.

* * * * *